US008227444B2

(12) United States Patent
Dejneka

(10) Patent No.: US 8,227,444 B2
(45) Date of Patent: Jul. 24, 2012

(54) COMPOSITIONS AND METHODS FOR INHIBITION OF VEGF

(75) Inventor: Nadine Dejneka, Wynnewood, PA (US)

(73) Assignee: Opko Ophthalmics, LLC, Miami, FL (US)

( * ) Notice: Subject to any disclaimer, the term of this patent is extended or adjusted under 35 U.S.C. 154(b) by 0 days.

(21) Appl. No.: 12/960,933

(22) Filed: Dec. 6, 2010

(65) Prior Publication Data

US 2011/0142915 A1 Jun. 16, 2011

Related U.S. Application Data

(60) Provisional application No. 61/266,645, filed on Dec. 4, 2009.

(51) Int. Cl.
| | |
|---|---|
| A61K 48/00 | (2006.01) |
| A61K 43/00 | (2006.01) |
| C07H 21/02 | (2006.01) |
| C07H 21/04 | (2006.01) |
| C12N 15/63 | (2006.01) |

(52) U.S. Cl. ..... 514/44; 536/23.1; 536/24.5; 435/320.1; 425/450

(58) Field of Classification Search ......... None
See application file for complete search history.

(56) References Cited

U.S. PATENT DOCUMENTS

| | | | |
|---|---|---|---|
| 4,235,871 | A | 11/1980 | Papahadjopoulos et al. |
| 4,501,728 | A | 2/1985 | Geho et al. |
| 4,837,028 | A | 6/1989 | Allen |
| 4,920,016 | A | 4/1990 | Allen et al. |
| 5,019,369 | A | 5/1991 | Presant et al. |
| 5,139,941 | A | 8/1992 | Muzyczka et al. |
| 5,252,479 | A | 10/1993 | Srivastava |
| 5,902,598 | A | 5/1999 | Chen et al. |
| 6,331,313 | B1 | 12/2001 | Wong et al. |
| 6,355,271 | B1 | 3/2002 | Bell et al. |
| 6,375,972 | B1 | 4/2002 | Guo et al. |
| 7,148,342 | B2 | 12/2006 | Tolentino et al. |
| 2002/0086356 | A1 | 7/2002 | Tuschl et al. |
| 2005/0281861 | A1 | 12/2005 | Hughes et al. |
| 2009/0226531 | A1 | 9/2009 | Lyons et al. |

FOREIGN PATENT DOCUMENTS

| | | |
|---|---|---|
| WO | WO 93/24641 A2 | 12/1993 |
| WO | WO 94/13788 A1 | 6/1994 |
| WO | WO 2004/009769 A2 * | 1/2004 |

OTHER PUBLICATIONS

Scherer et al., Approaches for the sequence-specific knockdown of mRNA, 2003, Nat. Biotechnol., 21(12), pp. 1457-1465.*
Zhang et al., Targeted Gene Silencing by Small Interfering RNA-Based Knock-Down Technology, 2004, Current Pharmaceutical Biotechnology, vol. 5, p. 1-7.*
Acheampong, et al., Distribution of brimonidine into anterior and posterior tissues of monkey rabbit, and rat eyes, *Drug Metabo. Dispos.* (Apr. 2002). 30(4):421-429.
Altschul, et al., Basic Local Alignment Search Tool, *J. Mol Biol.* (Oct. 5, 1990), 215(3):403-410.
Altschul, et al., Gapped BLAST and PSI-BLAST: a new generation of protein database search programs, *Nucleic Acids Res.* (Sep. 1, 1997), 25(17):3389-3402.
Ambati, et al., Transscleral drug delivery to the retina and choroid, *Prog Retin Eye Res.* (Mar. 2002). 21(2):145-151.
Anderson, Human gene therapy, *Nature* (Apr. 30, 1998). 392(6679 Suppl):25-30.
Bates, et al., $VEGF_{165}b$, an Inhibitory Splice Variant of Vascular Endothelial Growth Factor, Is Down-Regulated in Renal Cell Carcinoma, *Cancer Res.* (Jul. 15, 2002). 62(14):4123-4131.
Bennett, et al., Humoral response after administration of E1-deleted adenoviruses: immune privilege of the subretinal space. *Hum Gene Ther* (Sep. 10, 1996), 7(14):1763-1769 (Abstract).
Brummelkamp, et al., A System for Stable Expression of Short Interfering RNAs in Mammalian Cells, *Science* (Apr. 19, 2002), 296(5567):550-553.
Bustin, Absolute Quantification of mRNA Using Real-time Reverse Transcription Polymerase Chain Reaction Assays, *J. Mol. Endocrinol.* (Oct. 2000). 25(2):169-193.
Dornburg, Reticuloendotheliosis Viruses and derived vectors, *Gene Ther.* (Jul. 1995), 2(5):301-310.
Eglitis, et al., Retroviral Vectors for Introduction of Genes into Mammalian Cells, *Biotechniques* (Jul.-Aug. 1988), 6(7):608-614.
Fisher, et al., Transduction with Recombinant Adeno-Associated Virus for Gene Therapy is Limited by Leading-Strand Synthesis, *J. Virol.* (Jan. 1996), 70(1):520-532.
Gabizon, et al., Liposome formulations with prolonged circulation time in blood and enhanced uptake by tumors, *Proc Natl Acad Sci USA* (Sep. 1988), 85(18):6949-6953.
Genbank Accession No. AF 091352 (1998).
Genbank Accession No. AF 430806 (2001).
Genbank Accession No. AJ 010438 (1998).
Genbank Accession No. CS 245578 (2005).
Genbank Accession No. CS 245579 (2005).
Kleinman, et al., Sequence- and target-independent angiogenesis suppression by siRNA via TLR3, *Nature* (Apr. 3, 2008), 452(7187):591-597.
Lee, et al., Expression of small interfering RNAs targeted against HIV-1 rev transcripts in human cells, *Nat Biotechnol.* (May 2002), 20(5):500-505.
Miller, Retrovirus Packaging Cells, *Hum Gene Ther.* (Spring 1990), 1(1):5-14 (Abstract).
Miyagishi, et al., U6 promoter-driven siRNAs with four uridine 3' overhangs efficiently suppress targeted gene expression in mammalian cells, *Nat Biotechnol.* (May 2002), 20(5):497-500.
Paddison, et al., Short hairpin RNAs (shRNAs) induce sequence-specific silencing in mammalian cells, *Genes Dev.* (Apr. 15, 2002), 16(8):948-958.
Paul, et al., Effective expression of small interfering RNA in human cells, *Nat Biotechnol.* (May 2002), 20(5):505-508.

(Continued)

Primary Examiner — Amy Bowman
(74) Attorney, Agent, or Firm — Pepper Hamilton LLP

(57) ABSTRACT

Disclosed herein are siRNA compositions and methods useful for inhibiting expression of vascular endothelial growth factor (VEGF) isoforms. Diseases which involve angiogenesis stimulated by overexpression of VEGF, such as diabetic retinopathy, age related macular degeneration and many types of cancer, can be treated by administering small interfering RNAs as disclosed.

19 Claims, 41 Drawing Sheets

OTHER PUBLICATIONS

Remington's Pharmaceutical Sciences, 17th Ed., Mack Publishing Co., Easton, PA (1985) (TOC).

Samulski, et al., A Recombinant Plasmid from Which an Infectious Adeno-Associated Virus Genome Can Be Excised in Vitro and its use to Study Viral Replication, *J Virol.* (Oct. 1987), 61(10):3096-3101.

Samulski, et al., Helper-Free Stocks of Recombinant Adeno-Associated Viruses: Normal Integration Does Not Require Viral Gene Expression, *J Virol.* (Sep. 1989), 63(9):3822-3828.

Szoka, Jr., et al., Comparative Properties and Methods of Preparation of Lipid Vesicles (Liposomes), *Ann. Rev. Biophys. Bioeng.* (Jun. 1980). 9:467-508.

Tuschl, Expanding Small RNA Interference, *Nat. Biotechnol.* (May 2002). 20(5):446-448.

Tuschl, The siRNA user guide, http://www.mpidpc.gwdg.de/abteilungen/100/105/sirna.html. (Oct. 11, 2002).

Xia, et al., siRNA-mediated gene silencing *in vitro* and *in vivo*, *Nat Biotechnol.* (Oct. 2002), 20(10):1006-1010.

\* cited by examiner

```
                              Exon 7/8 boundry
nt.          518
VEGF 165     Aaggcgaggcagcttgagttaaacgaacgtacttgcagatgtgacaagccgaggcggtga
VEGF 165B    Aaggcgaggcagcttgagttaaacgaacgtacttgcag----------------------

VEGF 165     gccggggcaggaggaaggagcctccctcagggtttc-------gggaaccagatctctcaccaggaaa
VEGF 165B    ----------------------------------------------------atctctcaccaggaaa VEGF 165     gactgatatacagaacgatcgatacagaaaccac     SEQ ID NO: 3
VEGF 165B    gactgatatacagaacgatcgatacagaaaccac     SEQ ID NO: 127
```

Fig. 11

LANE 1: NO Rxn
LANE 2: NO Rxn
LANE 3: RIBOJUICE
LANE 4: 25 nM FAM-GAPDHsiRNA
LANE 5: 25 nM EGFP siRNA
LANE 6: 25 nM BEVASIRANIB
LANE 7: 25 nM OPX-HVB-004
LANE 8: 25 nM OPX-HVB-010
LANE 9: 25 nM OPX-HVB-011
LANE 10: 25 nM OPX-HVB-012
LANE 11: 5 µg/mL CYCLOHEXIMIDE

LANE 1: NO Rx
LANE 2: NO Rxn
LANE 3: RIBOJUICE
LANE 4: 25 nM FAM-GAPDH siRNA
LANE 5: 25 nM EGFP siRNA
LANE 6: 25 nM BEVASIRANIB
LANE 7: 25 nM OPX-HVB-004
LANE 8: 25 nM OPX-HVB-010
LANE 9: 25 nM OPX-HVB-011
LANE 10: 25 nM OPX-HVB-012
LANE 11: 5 μg/mL CYCLOHEXIMIDE

CYTOKINE PROFILE OF ARPE19 CELLS FOLLOWING TREATMENT WITH siRNAs

| CYTOKINE | POLY I:C | BEVASIRANIB | OPK-HVB-004 | OPK-HVB-010 | OPK-HVB-009 | OPK-HVB-012 |
|---|---|---|---|---|---|---|
| IFN-α | - | - | - | - | - | - |
| IFN-β | - | - | - | - | - | - |
| IFN-γ | - | - | - | - | - | - |
| IL-8 | + | - | + | - | - | + |
| IL-6 | + | + | + | - | - | + |
| TNFα | + | - | - | - | - | - |
| ICAM | + | - | - | - | - | - |
| IL-12 | - | - | - | - | - | - |
| MCP-1 | + | - | + | - | - | + |

FIG. 23

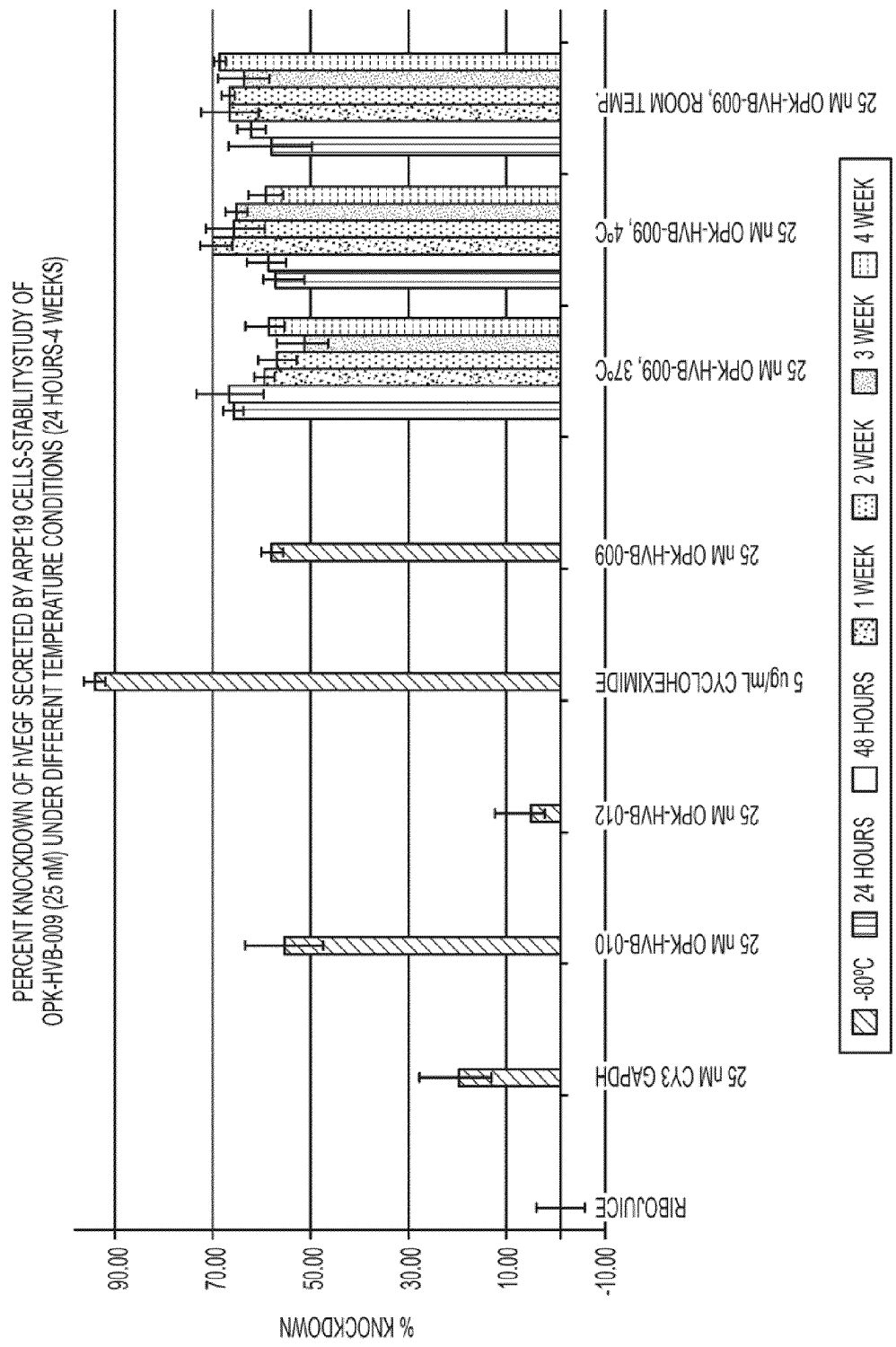

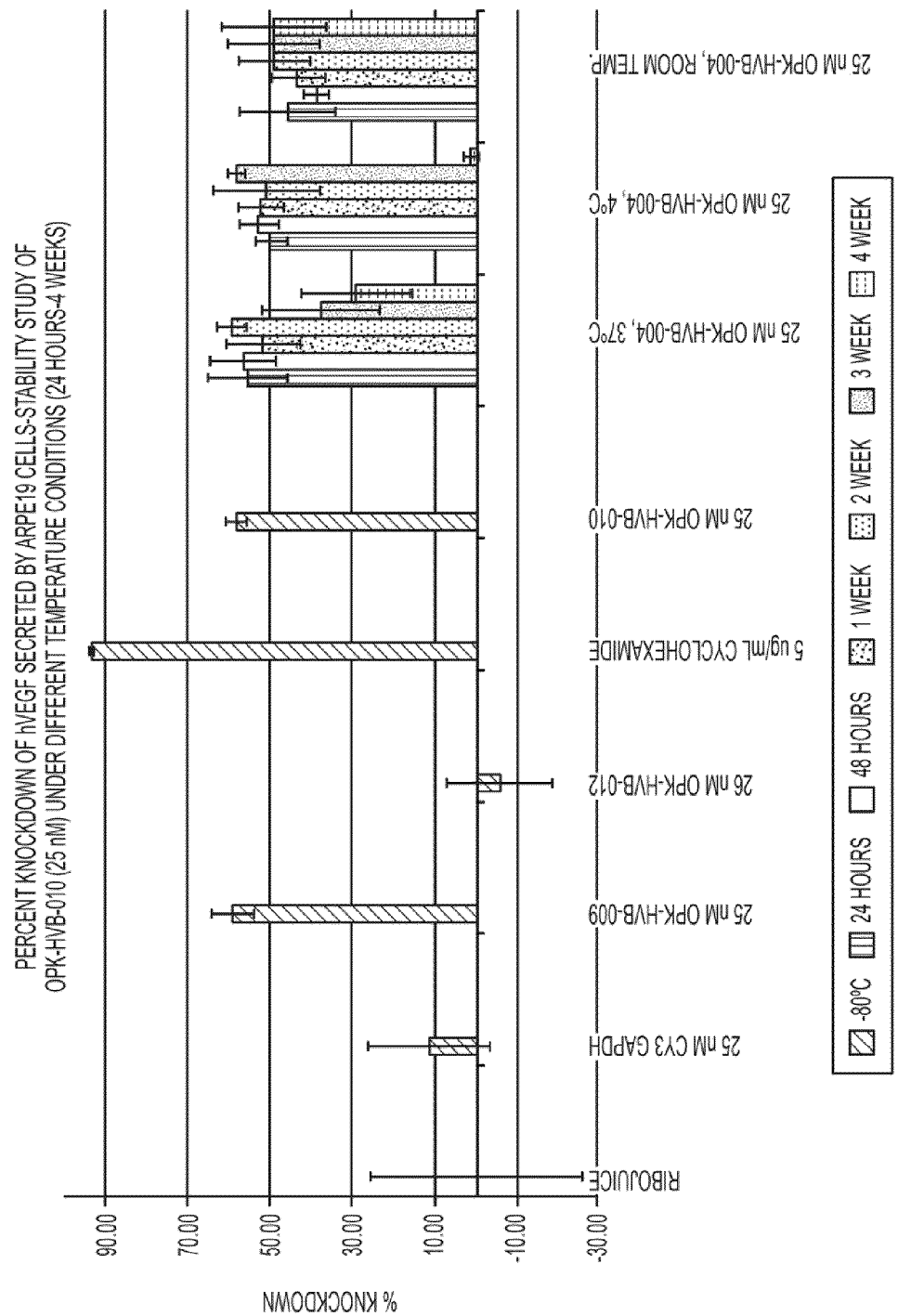

Human  nt 541
       gaacgtactt gcaga tgt gac aag ccg agg cgg tga    SEQ ID NO: 3
                        C   D   K   P   R   R
                        Cys Asp Lys Pro Arg Arg         SEQ ID NO: 130

Rat    gaacgtactt gcaga tgt gac aag cca agg cgg tga    SEQ ID NO: 128
                        C   D   K   P   R   R
                        Cys Asp Lys Pro Arg Arg         SEQ ID NO: 130

Mouse  gaacgtactt gcaga tgt gac aac cca agg cgg tga    SEQ ID NO: 129
                        C   D   K   P   R   R
                        Cys Asp Lys Pro Arg Arg         SEQ ID NO: 130

| siRNA | Target Sequence | |
|---|---|---|
| OPK-HVB-004 | GTACTTGCAGATGTGACAA | SEQ ID NO: 88 |
| OPK-HVB-009 | TGCAGATGTGACAAGCCGA | SEQ ID NO: 93 |
| OPK-HVB-010 | GCAGATGTGACAAGCCGAG | SEQ ID NO: 94 |
| OPK-HVB-012 | AGATGTGACAAGCCGAGGC | SEQ ID NO: 96 |

Fig. 33

COMPOSITIONS AND METHODS FOR INHIBITION OF VEGF

CROSS-REFERENCE TO RELATED APPLICATIONS

This application claims benefit of priority to U.S. Provisional Patent Application No. 61/266,645 filed on Dec. 4, 2009 entitled "COMPOSITIONS AND METHODS FOR INHIBITION OF VEGF," the entire contents of which are hereby incorporated by reference.

GOVERNMENT INTERESTS

Not applicable

PARTIES TO A JOINT RESEARCH AGREEMENT

Not applicable

INCORPORATION BY REFERENCE OF MATERIAL SUBMITTED ON A COMPACT DISC

Not applicable

BACKGROUND

1. Field of Invention
Not applicable
2. Description of Related Art
Not applicable

BRIEF SUMMARY OF THE INVENTION

Angiogenesis, defined as the growth of new capillary blood vessels or "neovascularization," plays a fundamental role in growth and development. In mature humans, the ability to initiate angiogenesis is present in all tissues, but is held under strict control. A key regulator of angiogenesis is vascular endothelial growth factor ("VEGF"), also called vascular permeability factor ("VPF"). Angiogenesis is initiated when secreted VEGF binds to the Flt-1 and Flk-1/KDR receptors (also called VEGF receptor 1 and VEGF receptor 2), which are expressed on the surface of endothelial cells. Flt-1 and Flk-1/KDR are transmembrane protein tyrosine kinases, and binding of VEGF initiates a cell signal cascade resulting in the ultimate neovascularization in the surrounding tissue.

There are three main different VEGF alternative splice forms (i.e., isoforms) in humans ($VEGF_{121}$, $VEGF_{165}$, and $VEGF_{189}$), while a number of other variants also exist ($VEGF_{206}$, $VEGF_{183}$, $VEGF_{148}$, $VEGF_{165b}$ and $VEGF_{145}$) Remarkably, not all of the isoforms are pro-angiogenic. It has been demonstrated that at least $VEGF_{165b}$ is capable of counteracting the effects of $VEGF_{165}$ induced angiogenesis. Without being bound by theory, it appears that $VEGF_{165b}$ is capable of preventing VEGF Receptor 2 signaling. As such, secretion of $VEGF_{165b}$ may be able to prevent or retard angiogenesis in pathological states.

Aberrant angiogenesis, or the pathogenic growth of new blood vessels, is implicated in a number of conditions. Among these conditions are diabetic retinopathy, psoriasis, exudative or "wet" age-related macular degeneration ("ARMD"), rheumatoid arthritis and other inflammatory diseases, and most cancers. The diseased tissues or tumors associated with these conditions express abnormally high levels of VEGF, and show a high degree of vascularization or vascular permeability.

ARMD in particular is a clinically important angiogenic disease. This condition is characterized by choroidal neovascularization in one or both eyes in aging individuals, and is the major cause of blindness in industrialized countries.

RNA interference (hereinafter "RNAi") is a method of post-transcriptional gene regulation that is conserved throughout many eukaryotic organisms. RNAi is induced by short (i.e., <30 nucleotide) double stranded RNA ("dsRNA") molecules which are present in the cell. These short dsRNA molecules, called "short interfering RNA" or "siRNA," cause the destruction of messenger RNAs ("mRNAs") which share sequence homology with the siRNA to within one nucleotide resolution. It is believed that the siRNA and the targeted mRNA bind to an "RNA-induced silencing complex" or "RISC", which cleaves the targeted mRNA. The siRNA is apparently recycled much like a multiple-turnover enzyme, with 1 siRNA molecule capable of inducing cleavage of approximately 1000 mRNA molecules. siRNA-mediated RNAi degradation of an mRNA is therefore more effective than currently available technologies for inhibiting expression of a target gene. However, such methods are not directly able to be translated into therapeutic agents for treatment of disease.

What is needed, therefore, are agents which selectively inhibit expression of pro-angiogenic VEGF in catalytic or sub-stoichiometric amounts in mammals, while inducing or maintaining the secretion of anti-angiogenic VEGF isoforms.

The present disclosure is directed to siRNAs which specifically target and cause RNAi-induced degradation of mRNA from VEGF and its isoforms. The siRNA compounds and compositions of the disclosure are used to inhibit angiogenesis, in particular for the treatment of cancerous tumors, age-related macular degeneration, and other angiogenic diseases.

Thus, the disclosure provides an isolated siRNA which targets human VEGF mRNA, or an alternative splice form, mutant or cognate thereof. For example, in one embodiment, the siRNA targets pro-angiogenic VEGF mRNA isoforms such as $VEGF_{121}$, $VEGF_{165}$, $VEGF_{189}$, $VEGF_{206}$, $VEGF_{183}$, $VEGF_{148}$, and/or $VEGF_{145}$. In certain embodiments, the siRNA comprises a sense RNA strand and an antisense RNA strand which form an RNA duplex. The sense RNA strand comprises a nucleotide sequence identical to a target sequence of about 19 to about 25 contiguous nucleotides in the target mRNA.

The disclosure also provides recombinant plasmids and viral vectors which express the siRNA disclosed herein, as well as pharmaceutical compositions comprising such an siRNA and a pharmaceutically acceptable carrier.

The disclosure further provides a method of inhibiting expression of human pro-angiogenic VEGF mRNA, or an alternative splice form, mutant or cognate thereof, while sparing anti-angiogenic VEGF mRNA, comprising administering to a subject an effective amount of siRNA such that the target mRNA is degraded.

The disclosure further provides a method of inhibiting angiogenesis in a subject, comprising administering to a subject an effective amount of an siRNA targeted to pro-angiogenic human VEGF mRNA or an alternative splice form, mutant or cognate thereof.

The disclosure further provides a method of treating an angiogenic disease, comprising administering to a subject in need of such treatment an effective amount of an siRNA targeted to human proangiogenic VEGF mRNA or an alternative splice form, mutant or cognate thereof, such that angiogenesis associated with the angiogenic disease is inhibited.

DESCRIPTION OF DRAWINGS

For a fuller understanding of the nature and advantages of the present invention, reference should be had to the following detailed description taken in connection with the accompanying drawings, in which:

FIG. 11 is a diagram comparing the homology of VEGF$_{165}$ and VEGF$_{165b}$ at the exon 7/8 junction.

FIG. 23 depicts the cytokine profile of ARPE19 cells following treatment with selected siRNAs.

FIG. 31 depicts the stability of OPK-HVB-009 under different temperature conditions over time.

FIG. 32 depicts the stability of OPK-HVB-010 under different temperature conditions over time FIG. 33 depicts the homology between human, rat and mouse VEGF sequences at the 3' terminal end.

DETAILED DESCRIPTION

Figure 1A:
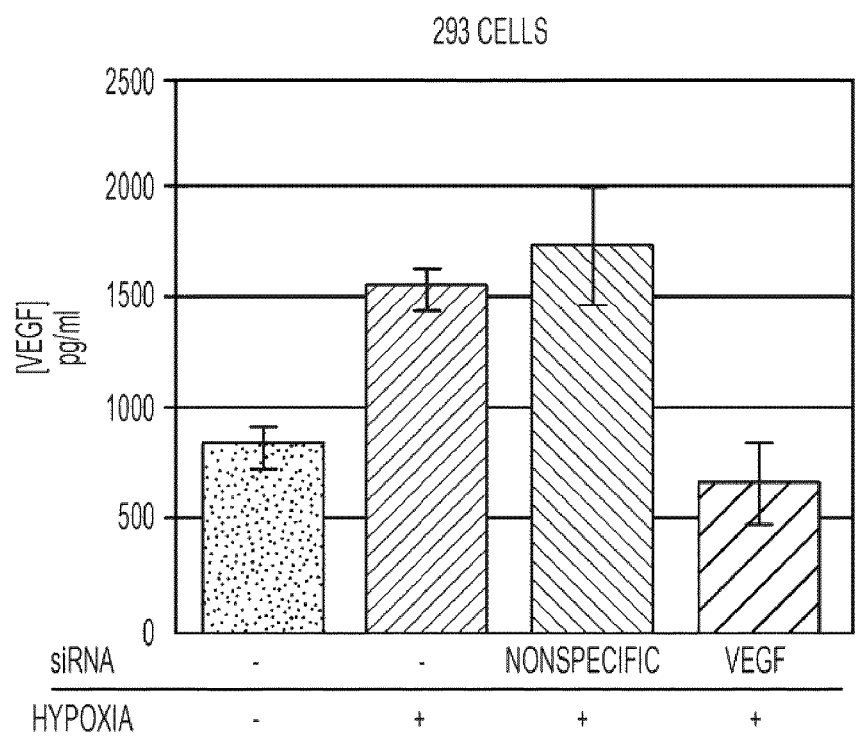
FIGS. 1A and 1B are a histograms of VEGF concentration (in pg/ml) in hypoxic 293 and HeLa cells treated with no siRNA ("−"); nonspecific siRNA ("nonspecific"); or siRNA targeting human VEGF mRNA ("VEGF"). VEGF concentration (in pg/ml) in non-hypoxic 293 and HeLa cells is also shown. Each bar represents the average of four experiments, and the error is the standard deviation of the mean.

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a", "an", and "the" include plural reference unless the context clearly dictates otherwise. Thus, for example, reference to a "molecule" is a reference to one or more molecules and equivalents thereof known to those skilled in the art, and so forth. As used herein, the term "about" means plus or minus 10% of the numerical value of the number with which it is being used. Therefore, about 50% means in the range of 45%-55%.

As used herein, a "subject" includes a human being or non-human animal. In certain embodiments, the subject is a human being.

As used herein, an "effective amount" of the siRNA is an amount sufficient to cause RNAi-mediated degradation of the target mRNA in cell. The term clinically effective amount is an amount that when administered to a subject, will inhibit the progression of angiogenesis in a subject by RNA silencing.

As used herein, "isolated" means altered or removed from the natural state through human intervention. For example, an siRNA naturally present in a living animal is not "isolated," but a synthetic siRNA, or an siRNA partially or completely separated from the coexisting materials of its natural state is "isolated." An isolated siRNA can exist in substantially purified form, or can exist in a non-native environment such as, for example, a cell into which the siRNA has been delivered.

As used herein, "target mRNA" means an mRNA comprising a complementary sense sequence to an siRNA antisense strand. Such a target mRNA need not be 100% homologous to the siRNA antisense strand, as long as the siRNA functions to silence or otherwise form a RISC complex with the target mRNA. Target mRNAs of particular use in the methods of the disclosure include, for example, pro-angiogenic VEGF mRNA isoforms such as $VEGF_{121}$, $VEGF_{165}$, and $VEGF_{189}$, $VEGF_{206}$, $VEGF_{183}$, $VEGF_{148}$, and $VEGF_{145}$ and combinations thereof. In certain other embodiments, the target mRNA does not comprise anti-angiogenic $VEGF_{165b}$ mRNA, but targets at least one other VEGF isoforms.

As used herein the term "partially non-complementary" is intended to mean an siRNA sequence which although, perhaps sharing some sequence homology to a non-target sequence still differs sufficiently such that RNA silencing does not occur for the non-target sequence. Partially non-complementary include sequences that are 90% homologous, 85%, homologous, 80% homologous, 75% homologous, 70% homologous, 65% homologous, 60%, homologous, 55% homologous, 50% homologous, 45% homologous, 40% homologous, 35%, homologous, 30% homologous, 25% homologous, 20% homologous, 15% homologous, 10%, homologous, 5% homologous, 2% homologous, and 1% homologous to a non-target sequence. A sequence that is entirely non-homologous to a non-target sequence is considered non-complementary to the sequence.

As used herein, a gene or mRNA which is "cognate" to human VEGF or mRNA from another mammalian species which is homologous to human VEGF. For example, the cognate VEGF mRNA from the mouse is given in SEQ ID NO: 1.

Unless otherwise indicated, all nucleic acid sequences herein are given in the 5' to 3' direction. Also, all deoxyribonucleotides in a nucleic acid sequence are represented by capital letters (e.g., deoxythymidine is "T"), and ribonucleotides in a nucleic acid sequence are represented by lower case letters (e.g., uridine is "u").

Compositions and methods comprising siRNA targeted to VEGF and its various isoforms can be used to inhibit angiogenesis, in particular for the treatment of angiogenic disease. The siRNA are believed to cause the RNAi-mediated degradation of these mRNAs, so that the protein product of the VEGF and its isoforms are not produced or is produced in reduced amounts. Because VEGF binding to the Flt-1 or Flk-1/KDR receptors is required for initiating and maintaining angiogenesis, the siRNA-mediated degradation of VEGF and its isoforms as well as Flt-1 or Flk-1/KDR mRNA may also be used to inhibit the angiogenic process.

One aspect of the present disclosure therefore provides isolated siRNA comprising short double-stranded RNA from about 17 nucleotides to about 29 nucleotides in length, and in certain embodiments from about 19 to about 25 nucleotides in length, that are targeted to the target mRNA. The siRNA comprise a sense RNA strand and a complementary antisense RNA strand annealed together by standard Watson-Crick base-pairing interactions (hereinafter "base-paired"). As is described in more detail below, the sense strand comprises a nucleic acid sequence which is identical or closely homologous to a target sequence contained within the target mRNA.

The sense and antisense strands of the siRNA can comprise two complementary, single-stranded RNA molecules or can comprise a single molecule in which two complementary portions are base-paired and are covalently linked by a single-stranded "hairpin" area. Without wishing to be bound by any theory, it is believed that the hairpin area of the latter type of siRNA molecule is cleaved intracellularly by the "Dicer" protein (or its equivalent) to form an siRNA of two individual base-paired RNA molecules.

Splice variants of human VEGF are known, including pro-angiogenic VEGF mRNA isoforms such as $VEGF_{121}$ (SEQ ID NO: 2), $VEGF_{165}$ (SEQ ID NO: 3), and $VEGF_{189}$ (SEQ ID NO: 4), $VEGF_{206}$ (SEQ ID NO: 5; GenBank Accession No. CS245579), $VEGF_{183}$ (GenBank Accession No. AJ010438), $VEGF_{148}$ (GenBank Accession No. AF091352), and $VEGF_{145}$ (GenBank Accession No. C5245578), as well as anti-angiogenic $VEGF_{165b}$ mRNA (GenBank Accession No.

AF430806). The mRNA transcribed from the human VEGF and its isoforms, as well as Flt-1 (SEQ ID NO: 6) or Flk-1/KDR (SEQ ID NO: 7) genes can be analyzed for further alternative splice forms using techniques well-known in the art. Such techniques include reverse transcription-polymerase chain reaction (RT-PCR), northern blotting and in-situ hybridization. Techniques for analyzing mRNA sequences are described, for example, in Busting S A (2000), *J. Mol. Endocrinol.* 25: 169-193, the entire disclosure of which is herein incorporated by reference. Representative techniques for identifying alternatively spliced mRNAs are also described below.

For example, databases that contain nucleotide sequences related to a given disease gene can be used to identify alternatively spliced mRNA. Such databases include GenBank, Embase, and the Cancer Genome Anatomy Project (CGAP) database. The CGAP database, for example, contains expressed sequence tags (ESTs) from various types of human cancers. An mRNA or gene sequence from the VEGF and its isoforms as well as Flt-1 or Flk-1/KDR genes can be used to query such a database to determine whether ESTs representing alternatively spliced mRNAs have been found for a these genes.

A technique called "RNAse protection" can also be used to identify alternatively spliced VEGF and its isoforms as well as Flt-1 or Flk-1/KDR mRNAs. RNAse protection involves translation of a gene sequence into synthetic RNA, which is hybridized to RNA derived from other cells; for example, cells from tissue at or near the site of neovascularization. The hybridized RNA is then incubated with enzymes that recognize RNA:RNA hybrid mismatches. Smaller than expected fragments indicate the presence of alternatively spliced mRNAs. The putative alternatively spliced mRNAs can be cloned and sequenced by methods well known to those skilled in the art.

RT-PCR can also be used to identify alternatively spliced VEGF and its isoforms as well as Flt-1 or Flk-1/KDR mRNAs. In RT-PCR, mRNA from tissue or cells is converted into cDNA by the enzyme reverse transcriptase, using methods well-known to those of ordinary skill in the art. The coding sequence of the cDNA is then amplified via PCR using a forward primer located in the 5' translated region, and a reverse primer located in the 3' translated region. In some embodiments, all the bases encoding the cDNA are amplified. The amplified products can be analyzed for alternative splice forms, for example by comparing the size of the amplified products with the size of the expected product from normally spliced mRNA, e.g., by agarose gel electrophoresis. Any change in the size of the amplified product can indicate alternative splicing.

mRNA produced from mutant VEGF and its isoforms as well as Flt-1 or Flk-1/KDR genes can also be readily identified through the techniques described above for identifying alternative splice forms. As used herein, "mutant" VEGF and its isoforms as well as Flt-1 or Flk-1/KDR genes or mRNA include human VEGF and its isoforms as well as Flt-1 or Flk-1/KDR genes or mRNA which differ in sequence from the VEGF and its isoforms as well as Flt-1 or Flk-1/KDR sequences set forth herein. Thus, allelic forms of these genes, and the mRNA produced from them, are considered "mutants" for purposes of this invention.

Figure 10:
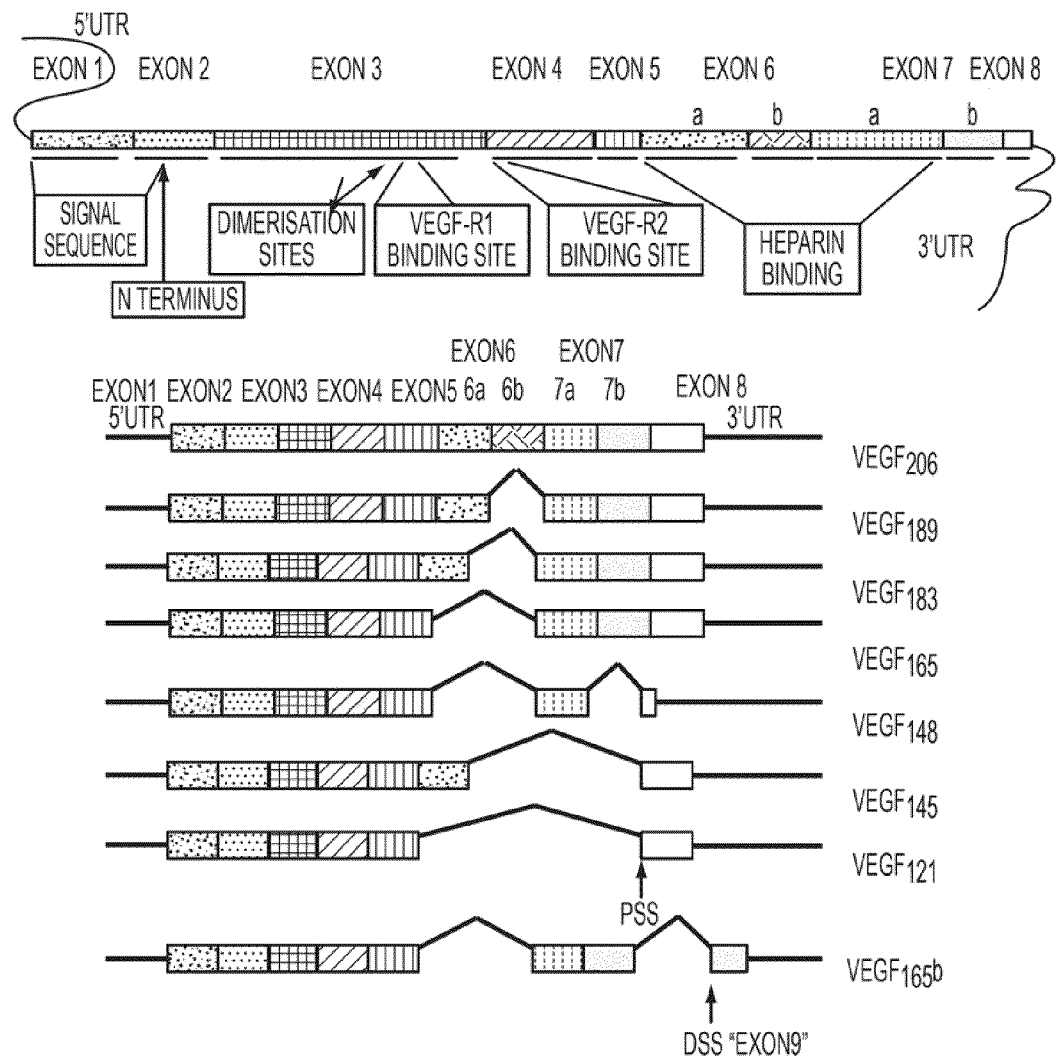
FIG. 10 is a schematic of the various isoforms of VEGF and their exon usage.

It is understood that human VEGF and its isoforms, as well as Flt-1 or Flk-1/KDR mRNA may contain target sequences in common with their respective alternative splice forms, cognates or mutants. A single siRNA comprising such a common targeting sequence can therefore induce RNAi-mediated degradation of different RNA types which contain the common targeting sequence. For example, as shown in FIG. 10, all VEGF isoforms share exons 1-5. However, in VEGF$_{121}$ (SEQ ID NO: 2) exons 6 and 7 (7a and 7b) are deleted. In VEGF$_{165}$ (SEQ ID NO: 3) exon 6 (6a and 6b) is deleted. In VEGF$_{189}$ (SEQ ID NO: 4) exon 6b is deleted. In VEGF$_{183}$ a portion of exon 6a is deleted as well as the complete exon 6b sequence. VEGF$_{148}$ has a deletion of exon 6 (6a and 6b) as well as exon 7b and a portion of exon 8. In VEGF$_{145}$ exon 6b and exon 7 (7a and 7b) are deleted. The only known anti-angiogenic isoform of VEGF, VEGF$_{165}^{b}$, lacks exon 6 (6a and 6b), but additionally comprises a pseudo-exon 9. The pseudo-exon 9 is a result of a reading frame shift caused by the deletion of a stop codon, thus allowing a portion of the 3'UTR to be translated as protein. See for example, Bates et al., Can. Res. 62:4123 (2002), herein incorporated by reference in its entirety. VEGF$_{206}$ (SEQ ID NO: 5) is the full length sequence VEGF with no deletions. Thus, in certain embodiments, the siRNA targets one or more isoforms, such as VEGF$_{121}$(SEQ ID NO: 2), VEGF$_{165}$ (SEQ ID NO: 3), and VEGF$_{189}$(SEQ ID NO: 4), VEGF$_{206}$(SEQ ID NO: 5; GenBank Accession No. CS245579), VEGF$_{183}$ (GenBank Accession No. AJ010438), VEGF$_{148}$ (GenBank Accession No. AF091352), and/or VEGF$_{145}$ (GenBank Accession No. CS245578), but spares others, such as VEGF$_{165b}$, because the siRNA targets a shared exon among certain isoforms but not others.

In one embodiment, provided is an isolated siRNA comprising of a duplex of a first RNA strand and a second RNA strand, said first RNA strand comprising a nucleotide sequence identical to a target sequence of about 19 to about 25 contiguous nucleotides to a vascular endothelial growth factor (VEGF) isoform selected from the group consisting of human VEGF$_{121}$, VEGF$_{165}$ VEGF$_{189}$, VEGF$_{206}$, VEGF$_{183}$, VEGF$_{148}$, VEGF$_{145}$ and combinations thereof; further wherein said siRNA is at least partially non-complementary to VEGF$_{165b}$, with the proviso that the human VEGF mRNA is not SEQ ID NO. 42. Further embodiments include methods of using such siRNA to inhibit angiogenesis and pharmaceutical compositions comprising a therapeutically effective amount of such siRNA to inhibit angiogenesis.

The siRNA can comprise partially purified RNA, substantially pure RNA, synthetic RNA, or recombinantly produced RNA, as well as altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, including modifications that make the siRNA resistant to nuclease digestion.

One or both strands of the siRNA can also comprise a 3' overhang. As used herein, a "3' overhang" refers to at least one unpaired nucleotide extending from the 3'-end of a duplexed RNA strand. In some embodiments, the siRNA does not comprise a overhang and has a blunt end. In some embodiments, both ends of the siRNA comprise a blunt end. In some embodiments, the siRNA comprises a 17 mer that contiguous with a target mRNA and dTdT overhang. In some embodiments, the siRNA is a siRNA that can inhibit the secretion or production of VEGF from cells from different species. For example, in some embodiments, the siRNA can inhibit VEGF secretion or inhibition from a human cell, a rat cell, and/or a mouse cell. In some embodiments, the siRNA can inhibit the secretion or production of VEGF from a mouse cell and a human cell, but not from a rat cell. In some embodiments, the siRNA can inhibit the secretion or production of VEGF from a rat cell and a human cell, but not from a mouse cell. In some embodiments, the siRNA can inhibit the secretion or production of VEGF from a human cell, a mouse cell, and a rat cell.

The selectivity of the siRNA can be based upon the homology between the different sequences. For example, FIG. 33 shows the homology between the terminal codons encoding human, mouse and rat VEGF. These differences can be exploited to produce siRNAs that can selectively inhibit the production of VEGF from one or more species.

In some embodiments, siRNAs comprising less than 21 nucleotides, e.g. 17, 18, 19, or 20, can be used to avoid any potential non-specific in vivo responses. (See, Ambati, Nature, 452, 591-597 (3 Apr. 2008)). For example, siRNAs comprising less than 21 nucleotides can be used to avoid activating a TLR3 response in vivo.

Thus in one embodiment, the siRNA comprises at least one 3' overhang of from 1 to about 6 nucleotides (which includes ribonucleotides or deoxynucleotides) in length, preferably from 1 to about 5 nucleotides in length, more preferably from 1 to about 4 nucleotides in length, and particularly preferably from about 2 to about 4 nucleotides in length.

In the embodiment in which both strands of the siRNA molecule comprise a 3' overhang, the length of the overhangs can be the same or different for each strand. In a most preferred embodiment, the 3' overhang is present on both strands of the siRNA, and is 2 nucleotides in length. For example, each strand of the siRNA can comprise 3' overhangs of dithymidylic acid ("TT") or diuridylic acid ("uu").

In order to enhance the stability of the present siRNA, the 3' overhangs can be also stabilized against degradation. In one embodiment, the overhangs are stabilized by including purine nucleotides, such as adenosine or guanosine nucleotides. Alternatively, substitution of pyrimidine nucleotides by modified analogues, e.g., substitution of uridine nucleotides in the 3' overhangs with 2'-deoxythymidine, is tolerated and does not affect the efficiency of RNAi degradation. In particular, the absence of a 2' hydroxyl in the 2'-deoxythymidine significantly enhances the nuclease resistance of the 3' overhang in tissue culture medium.

In certain embodiments, the siRNA comprises the sequence AA(N19)TT or NA(N21), where N is any nucleotide. These siRNA comprise approximately 30-70% GC, and preferably comprise approximately 50% G/C. The sequence of the sense siRNA strand corresponds to (N19)TT or N21 (i.e., positions 3 to 23), respectively. In the latter case, the 3' end of the sense siRNA is converted to TT. The rationale for this sequence conversion is to generate a symmetric duplex with respect to the sequence composition of the sense and antisense strand 3' overhangs. The antisense RNA strand is then synthesized as the complement to positions 1 to 21 of the sense strand.

Because position 1 of the 23-nt sense strand in these embodiments is not recognized in a sequence-specific manner by the antisense strand, the 3'-most nucleotide residue of the antisense strand can be chosen deliberately. However, the penultimate nucleotide of the antisense strand (complementary to position 2 of the 23-nt sense strand in either embodiment) is generally complementary to the targeted sequence.

In another embodiment, the siRNA comprises the sequence NAR(N17)YNN, where R is a purine (e.g., A or G) and Y is a pyrimidine (e.g., C or U/T). The respective 21-nt sense and antisense RNA strands of this embodiment therefore generally begin with a purine nucleotide. Such siRNA can be expressed from pol III expression vectors without a change in targeting site, as expression of RNAs from pol III promoters is only believed to be efficient when the first transcribed nucleotide is a purine.

In a further embodiment, the siRNA comprises a sequence having no more than five (5) consecutive purines or pyrimidines. In a further embodiment, the siRNA comprises a sequence having no more than five (5) consecutive nucleotides having the same nucleobase (i.e., A, C, G, or U/T).

The siRNA can be targeted to any stretch of approximately 19-25 contiguous nucleotides in any of the target mRNA sequences (the "target sequence"). Techniques for selecting target sequences for siRNA are given, for example, in Tuschl T et al., "The siRNA User Guide," revised Oct. 11, 2002, the entire disclosure of which is herein incorporated by reference. "The siRNA User Guide" is available on the world wide web at a website maintained by Dr. Thomas Tuschl, Department of Cellular Biochemistry, AG 105, Max-Planck-Institute for Biophysical Chemistry, 37077 Göttingen, Germany, and can be found by accessing the website of the Max Planck Institute and searching with the keyword "siRNA." Thus, the sense strand of the present siRNA comprises a nucleotide sequence identical to any contiguous stretch of about 19 to about 25 nucleotides in the target mRNA.

In some embodiments, the siRNA is 19 nucleotides and comprises 17 nucleotides that are identical to a target mRNA. In some embodiments, the siRNA is 19 nucleotides in length comprising at least one blunt end. In some embodiments, each end of the 19 mer has a blunt end. In some embodiments, the 19 mer comprises at least one dT overhang. In some embodiments, the 19 mer comprises two dT overhangs.

Generally, a target sequence on the target mRNA can be selected from a given cDNA sequence corresponding to the target mRNA, preferably beginning 50 to 100 nt downstream (i.e., in the 3' direction) from the start codon. The target sequence can, however, be located in the 5' or 3' untranslated regions, or in the region nearby the start codon (see, e.g., the target sequences of SEQ ID NOS: 73 and 74 in Table 1 below, which are within 100 nt of the 5'-end of the $VEGF_{121}$ cDNA.

In a further embodiment of the present invention, the target mRNA sequence comprises no more than five (5) consecutive purines or pyrimidines. For example, a suitable target sequence in the $VEGF_{121}$ cDNA sequence is:

```
    TCATCACGAAGTGGTGAAG        (SEQ ID NO: 8)
```

Thus, an siRNA targeting this sequence, and which has 3' uu overhangs on each strand (overhangs shown in bold), is:

```
    5'-ucaucacgaaguggugaaguu-3'    (SEQ ID NO: 9)

3'-uuaguagugcuucaccacuuc-5'    (SEQ ID NO: 10)
```

An siRNA targeting this same sequence, but having 3' TT overhangs on each strand (overhangs shown in bold) is:

```
    5'-ucaucacgaaguggugaagTT-3'    (SEQ ID NO: 11)

3'-TTaguagugcuucaccacuuc-5'    (SEQ ID NO: 12)
```

Other $VEGF_{121}$ target sequences from which siRNA can be derived are given in Table 1. It is understood that all $VEGF_{121}$ target sequences listed in Table 1 are within that portion of the $VEGF_{121}$ alternative splice form which is common to all human VEGF alternative splice forms. Thus, the $VEGF_{121}$ target sequences in Table 1 can also target $VEGF_{165}$, $VEGF_{189}$ and $VEGF_{206}$ mRNA. Target sequences which target a specific VEGF isoform can also be readily identified. For example, a target sequence which targets $VEGF_{165}$ mRNA but not $VEGF_{121}$ mRNA is AACGTACTTGCAGATGTGACA (SEQ ID NO: 13). Conversely, target sequences which target pro-angiogenic VEGF mRNA isoforms such as $VEGF_{121}$, $VEGF_{165}$, and $VEGF_{189}$, $VEGF_{206}$, $VEGF_{183}$, VEGF$_{148}$, and VEGF$_{145}$ and combinations thereof, but does not target anti-angiogenic VEGF$_{165b}$ mRNA include the sequences found in Table 2, with the proviso that the VEGF mRNA is not SEQ ID No. 42. In certain embodiments, said human VEGF mRNA is selected from the group consisting of SEQ ID NO: 86; SEQ ID NO: 87; SEQ ID NO: 88; SEQ ID NO: 89; SEQ ID NO: 90; SEQ ID NO: 91; SEQ ID NO: 92; SEQ ID NO: 93; SEQ ID NO: 94; SEQ ID NO: 95; SEQ ID NO: 96; SEQ ID NO: 97; and SEQ ID NO: 98. In certain embodiments, said human VEGF mRNA is selected from SEQ ID NO. 88 and SEQ ID NO. 94.

By selectively targeting the angiogenic isoforms of VEGF, while sparing the anti-angiogenic isoform, it is possible to enhance the anti-angiogenic effects of siRNA treatment. As shown in FIG. 11, the region between exon 7 and 9 differ between the angiogenic and antiangiogenic sequences. According to the various embodiments, it is possible to selectively target this region where the siRNA is at least partially complementary to the angiogenic isoforms, but at least partially or fully non-complementary to the anti-angiogenic isoform. Consequently, in certain embodiments, the siRNA would not inhibit the expression of the anti-angiogenic isoform, VEGF$_{165b}$ with the proviso that the VEGF mRNA is not SEQ ID No. 42. In certain embodiments, said human VEGF mRNA is selected from the group consisting of SEQ ID NO: 86; SEQ ID NO: 87; SEQ ID NO: 88; SEQ ID NO: 89; SEQ ID NO: 90; SEQ ID NO: 91; SEQ ID NO: 92; SEQ ID NO: 93; SEQ ID NO: 94; SEQ ID NO: 95; SEQ ID NO: 96; SEQ ID NO: 97; SEQ ID NO: 98, SEQ ID NO 99, SEQ ID NO 100, SEQ ID NO 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, and SEQ ID NO: 118. In certain embodiments, said human VEGF mRNA is selected from SEQ ID NO. 88 and SEQ ID NO. 94.

Exemplary target sequences for human Flt-1 for human Flk-1/KDR are given in PCT/US2003/0022444 filed Jul. 18, 2003, herein incorporated by reference in its entirety.

TABLE 1

VEGF Target Sequences

| target sequence | SEQ ID NO: |
|---|---|
| cognate VEGF mRNA sequence | 1 |
| Splice variant VEGF$_{121}$ sequence | 2 |
| Splice variant VEGF$_{165}$ sequence | 3 |
| Splice variant VEGF$_{189}$ sequence | 4 |
| Splice variant VEGF$_{206}$ sequence | 5 |
| TCATCACGAAGTGGTGAAG | 8 |
| UCAUCACGAAGUGGUGAAGUU | 9 |
| UUAGUAGUGCUUCACCACUUC | 10 |
| UCAUCACGAAGUGGUGAAGTT | 11 |
| TTAGUAGUGCUUCACCACUUC | 12 |
| AACGTACTTGCAGATGTGACA | 13 |
| GTTCATGGATGTCTATCAG | 14 |

TABLE 1-continued

VEGF Target Sequences

| target sequence | SEQ ID NO: |
|---|---|
| TCGAGACCCTGGTGGACAT | 15 |
| TGACGAGGGCCTGGAGTGT | 16 |
| TGACGAGGGCCTGGAGTGT | 17 |
| CATCACCATGCAGATTATG | 18 |
| ACCTCACCAAGGCCAGCAC | 19 |
| GGCCAGCACATAGGAGAGA | 20 |
| CAAATGTGAATGCAGACCA | 21 |
| ATGTGAATGCAGACCAAAG | 22 |
| TGCAGACCAAAGAAAGATA | 23 |
| AGAAAGATAGAGCAAGACA | 24 |
| GAAAGATAGAGCAAGACAA | 25 |
| GATAGAGCAAGACAAGAAA | 26 |
| GACAAGAAAATCCCTGTGG | 27 |
| GAAAATCCCTGTGGGCCTT | 28 |
| AATCCCTGTGGGCCTTGCT | 29 |
| TCCCTGTGGGCCTTGCTCA | 30 |
| GCATTTGTTTGTACAAGAT | 31 |
| GATCCGCAGACGTGTAAAT | 32 |
| ATGTTCCTGCAAAAACACA | 33 |
| TGTTCCTGCAAAAACACAG | 34 |
| AAACACAGACTCGCGTTGC | 35 |
| AACACAGACTCGCGTTGCA | 36 |
| ACACAGACTCGCGTTGCAA | 37 |
| CACAGACTCGCGTTGCAAG | 38 |
| GGCGAGGCAGCTTGAGTTA | 39 |
| ACGAACGTACTTGCAGATG | 40 |
| CGAACGTACTTGCAGATGT | 41 |
| CGTACTTGCAGATGTGACA | 42 |
| GTGGTCCCAGGCTGCACCC | 43 |
| GGAGGAGGGCAGAATCATC | 44 |
| GTGGTGAAGTTCATGGATG | 45 |
| AATCATCACGAAGTGGTGAAG | 46 |
| AAGTTCATGGATGTCTATCAG | 47 |
| AATCGAGACCCTGGTGGACAT | 48 |
| AATGACGAGGGCCTGGAGTGT | 49 |
| AACATCACCATGCAGATTATG | 50 |
| AAACCTCACCAAGGCCAGCAC | 51 |
| AAGGCCAGCACATAGGAGAGA | 52 |

TABLE 1-continued

VEGF Target Sequences

| target sequence | SEQ ID NO: |
|---|---|
| AACAAATGTGAATGCAGACCA | 53 |
| AAATGTGAATGCAGACCAAAG | 54 |
| AATGCAGACCAAAGAAAGATA | 55 |
| AAAGAAAGATAGAGCAAGACA | 56 |
| AAGAAAGATAGAGCAAGACAA | 57 |
| AAGATAGAGCAAGACAAGAAAAT | 58 |
| AAGACAAGAAAATCCCTGTGGGC | 59 |
| AAGAAAATCCCTGTGGGCCTTGC | 60 |
| AATCCCTGTGGGCCTTGCTCAGA | 61 |
| AAGCATTTGTTTGTACAAGATCC | 62 |
| AAGATCCGCAGACGTGTAAATGT | 63 |
| AAATGTTCCTGCAAAAACACAGA | 64 |
| AATGTTCCTGCAAAAACACAGAC | 65 |
| AAAAACACAGACTCGCGTTGCAA | 66 |
| AAAACACAGACTCGCGTTGCAAG | 67 |
| AAACACAGACTCGCGTTGCAAGG | 68 |
| AACACAGACTCGCGTTGCAAGGC | 69 |
| AAGGCGAGGCAGCTTGAGTTAAA | 70 |
| AAACGAACGTACTTGCAGATGTG | 71 |
| AACGAACGTACTTGCAGATGTGA | 72 |
| AAGTGGTCCCAGGCTGCACCCAT | 73 |
| AAGGAGGAGGGCAGAATCATCAC | 74 |
| AAGTGGTGAAGTTCATGGATGTC | 75 |
| AAAATCCCTGTGGGCCTTGCTCA | 76 |
| ACCUCACCAAGGCCAGCACUU | 77 |
| GUGCUGGCCUUGGUGAGGUU | 78 |
| GGCUACGUCCAGCGCACC | 79 |
| AAACCUCACCAAAGCCAGCAC | 80 |
| ACCUCACCAAGGCCAGCAC | 119 |
| GUGCUGGCCUUGGUGAGGU | 120 |

TABLE 2

VEGF Target Sequences selectively excluding VEGF$_{165b}$

| siRNA Name | Target sequence (5'-3') |
|---|---|
| OPK-HVB-001 | AACGTACTTGCAGATGTGA (SEQ ID NO: 86) |
| OPK-HVB-002 | ACGTACTTGCAGATGTGAC (SEQ ID NO: 87) |
| OPK-HVB-003 | CGTACTTGCAGATGTGACA (SEQ ID NO: 42) |
| OPK-HVB-004 | GTACTTGCAGATGTGACAA (SEQ ID NO: 88) |
| OPK-HVB-005 | TACTTGCAGATGTGACAAG (SEQ ID NO: 89) |
| OPK-HVB-006 | ACTTGCAGATGTGACAAGC (SEQ ID NO: 90) |
| OPK-HVB-007 | CTTGCAGATGTGACAAGCC (SEQ ID NO: 91) |
| OPK-HVB-008 | TTGCAGATGTGACAAGCCG (SEQ ID NO: 92) |
| OPK-HVB-009 | TGCAGATGTGACAAGCCGA (SEQ ID NO: 93) |
| OPK-HVB-010 | GCAGATGTGACAAGCCGAG (SEQ ID NO: 94) |
| OPK-HVB-011 | CAGATGTGACAAGCCGAGG (SEQ ID NO: 95) |
| OPK-HVB-012 | AGATGTGACAAGCCGAGGC (SEQ ID NO: 96) |
| OPK-HVB-013 | GATGTGACAAGCCGAGGCG (SEQ ID NO: 97) |
| OPK-HVB-014 | ATGTGACAAGCCGAGGCGG (SEQ ID NO: 98) |
| OPK-HVB-004be | GTACTTGCAGATGTGACAA (SEQ ID NO: 99) |
| OPK-HVB-009be | TGCAGATGTGACAAGCCGA (SEQ ID NO: 100) |
| OPK-HVB-010be | GCAGATGTGACAAGCCGAG (SEQ ID NO: 101) |
| OPK-HVB-012be | AGATGTGACAAGCCGAGGC (SEQ ID NO: 102) |
| OPK-HVB-001a | AACGTACTTGCAGATGT (SEQ ID NO: 103) |
| OPK-HVB-002a | ACGTACTTGCAGATGTG (SEQ ID NO: 104) |
| OPK-HVB-003a | CGTACTTGCAGATGTGA (SEQ ID NO: 105) |
| OPK-HVB-004a | GTACTTGCAGATGTGAC (SEQ ID NO: 106) |
| OPK-HVB-005a | TACTTGCAGATGTGACA (SEQ ID NO: 107) |
| OPK-HVB-006a | ACTTGCAGATGTGACAA (SEQ ID NO: 108) |
| OPK-HVB-007a | CTTGCAGATGTGACAAG (SEQ ID NO: 109) |
| OPK-HVB-008a | TTGCAGATGTGACAAGC (SEQ ID NO: 110) |

TABLE 2-continued

VEGF Target Sequences selectively excluding VEGF$_{165b}$

| siRNA Name | Target sequence (5'-3') |
|---|---|
| OPK-HVB-009a | TGCAGATGTGACAAGCC (SEQ ID NO: 111) |
| OPK-HVB-010a | GCAGATGTGACAAGCCG (SEQ ID NO: 112) |
| OPK-HVB-011a | CAGATGTGACAAGCCGA (SEQ ID NO: 113) |
| OPK-HVB-012a | AGATGTGACAAGCCGAG (SEQ ID NO: 114) |
| OPK-HVB-013a | GATGTGACAAGCCGAGG (SEQ ID NO: 115) |
| OPK-HVB-014a | ATGTGACAAGCCGAGGC (SEQ ID NO: 116) |
| OPK-HVB-015a | TGTGACAAGCCGAGGCG (SEQ ID NO: 117) |
| OPK-HVB-016a | GTGACAAGCCGAGGCGG (SEQ ID NO: 118) |

The sequences with the names "OPK-HVB-XXXbe" refer to sequences that are 19 mer blunt end counterparts of the similar 21 mers. The sequences with the names "OPVHVB-XXXa" refer to 19 mers where there is a 17 bp nucleotide sequence with a dTdT overhang. Other sequences not specifically exemplified herein but targeting VEGF while sparing VEGF165b can also be made with similar properties.

Other blunt end nucleic acid molecules can also be used, but that do not necessarily spare VEGF165b. For example, an siRNA comprising a sense strand SEQ ID NO: 119 and an antisense strand comprising SEQ ID NO: 120 can be used. An siRNA comprising SEQ ID NO: 119 and SEQ ID NO: 120, wherein each siRNA comprises blunt ends can also be referred to as bevasiranib-be. For example, in some embodiments, the siRNA is a 19 mer with a blunt ends comprising SEQ ID NO: 119 and SEQ ID NO: 120 (See FIG. 36).

The siRNA can be obtained using a number of techniques known to those of skill in the art. For example, the siRNA can be chemically synthesized or recombinantly produced using methods known in the art, such as the Drosophila in vitro system described in U.S. published application 2002/0086356 of Tuschl et al., the entire disclosure of which is herein incorporated by reference.

In certain embodiments, the siRNA are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK).

Alternatively, siRNA can also be expressed from recombinant circular or linear DNA plasmids using any suitable promoter. Suitable promoters for expressing siRNA from a plasmid include, for example, the U6 or H1 RNA pol III promoter sequences and the cytomegalovirus promoter. Selection of other suitable promoters is within the skill in the art. The recombinant plasmids of the invention can also comprise inducible or regulatable promoters for expression of the siRNA in a particular tissue or in a particular intracellular environment.

The siRNA expressed from recombinant plasmids can either be isolated from cultured cell expression systems by standard techniques, or can be expressed intracellularly at or near the area of neovascularization in vivo. The use of recombinant plasmids to deliver siRNA to cells in vivo is discussed in more detail below.

siRNA can be expressed from a recombinant plasmid either as two separate, complementary RNA molecules, or as a single RNA molecule with two complementary regions.

Selection of plasmids suitable for expressing siRNA, methods for inserting nucleic acid sequences for expressing the siRNA into the plasmid, and methods of delivering the recombinant plasmid to the cells of interest are within the skill in the art. See, for example Tuschl, T. (2002), Nat. Biotechnol, 20: 446-448; Brummelkamp T R et al. (2002), Science 296: 550-553; Miyagishi M et al. (2002), Nat. Biotechnol. 20: 497-500; Paddison P J et al. (2002), Genes Dev. 16: 948-958; Lee N S et al. (2002), Nat. Biotechnol. 20: 500-505; and Paul C P et al. (2002), Nat. Biotechnol. 20: 505-508, the entire disclosures of which are herein incorporated by reference.

A plasmid comprising nucleic acid sequences for expressing an siRNA is described in Example 7 below. That plasmid, called pAAVsiRNA, comprises a sense RNA strand coding sequence in operable connection with a polyT termination sequence under the control of a human U6 RNA promoter, and an antisense RNA strand coding sequence in operable connection with a polyT termination sequence under the control of a human U6 RNA promoter. The plasmid pAAVsiRNA is ultimately intended for use in producing an recombinant adeno-associated viral vector comprising the same nucleic acid sequences for expressing an siRNA.

As used herein, "in operable connection with a polyT termination sequence" means that the nucleic acid sequences encoding the sense or antisense strands are immediately adjacent to the polyT termination signal in the 5' direction. During transcription of the sense or antisense sequences from the plasmid, the polyT termination signals act to terminate transcription.

As used herein, "under the control" of a promoter means that the nucleic acid sequences encoding the sense or antisense strands are located 3' of the promoter, so that the promoter can initiate transcription of the sense or antisense coding sequences.

The siRNA can also be expressed from recombinant viral vectors intracellularly at or near the area of neovascularization in vivo. The recombinant viral vectors of the invention comprise sequences encoding the siRNA and any suitable promoter for expressing the siRNA sequences. Suitable promoters include, for example, the U6 or H1 RNA pol III promoter sequences and the cytomegalovirus promoter. Selection of other suitable promoters is within the skill in the art. The recombinant viral vectors of the invention can also comprise inducible or regulatable promoters for expression of the siRNA in a particular tissue or in a particular intracellular environment. The use of recombinant viral vectors to deliver siRNA to cells in vivo is discussed in more detail below.

siRNA can be expressed from a recombinant viral vector either as two separate, complementary RNA molecules, or as a single RNA molecule with two complementary regions.

Any viral vector capable of accepting the coding sequences for the siRNA molecule(s) to be expressed can be used, for example vectors derived from adenovirus (AV); adeno-associated virus (AAV); retroviruses (e.g, lentiviruses (LV), Rhabdoviruses, murine leukemia virus); herpes virus, and the like. The tropism of the viral vectors can also be modified by pseudotyping the vectors with envelope proteins or other surface antigens from other viruses. For example, an AAV vector of the invention can be pseudotyped with surface proteins from vesicular stomatitis virus (VSV), rabies, Ebola, Mokola, and the like.

Selection of recombinant viral vectors suitable for use in the invention, methods for inserting nucleic acid sequences for expressing the siRNA into the vector, and methods of delivering the viral vector to the cells of interest are within the skill in the art. See, for example, Dornburg R (1995), *Gene Therap.* 2: 301-310; Eglitis M A (1988), *Biotechniques* 6: 608-614; Miller A D (1990), *Hum Gene Therap.* 1: 5-14; and Anderson W F (1998), *Nature* 392: 25-30, the entire disclosures of which are herein incorporated by reference.

Preferred viral vectors are those derived from AV and AAV. In a particularly preferred embodiment, the siRNA is expressed as two separate, complementary single-stranded RNA molecules from a recombinant AAV vector comprising, for example, either the U6 or H1 RNA promoters, or the cytomegalovirus (CMV) promoter.

A suitable AV vector for expressing the siRNA, a method for constructing the recombinant AV vector, and a method for delivering the vector into target cells, are described in Xia H et al. (2002), *Nat. Biotech.* 20: 1006-1010.

Suitable AAV vectors for expressing the siRNA, methods for constructing the recombinant AAV vector, and methods for delivering the vectors into target cells are described in Samulski R et al. (1987), *J. Virol.* 61: 3096-3101; Fisher K J et al. (1996), *J. Virol.,* 70: 520-532; Samulski R et al. (1989), *J. Virol.* 63: 3822-3826; U.S. Pat. No. 5,252,479; U.S. Pat. No. 5,139,941; International Patent Application No. WO 94/13788; and International Patent Application No. WO 93/24641, the entire disclosures of which are herein incorporated by reference. An exemplary method for generating a recombinant AAV vector of the invention is described in Example 7 below.

The ability of an siRNA containing a given target sequence to cause RNAi-mediated degradation of the target mRNA can be evaluated using standard techniques for measuring the levels of RNA or protein in cells. For example, siRNA can be delivered to cultured cells, and the levels of target mRNA can be measured by Northern blot or dot blotting techniques, or by quantitative RT-PCR. Alternatively, the levels of VEGF and its isoforms as well as Flt-1 or Flk-1/KDR receptor protein in the cultured cells can be measured by ELISA or Western blot. A suitable cell culture system for measuring the effect of the present siRNA on target mRNA or protein levels is described in Example 1 below.

RNAi-mediated degradation of target mRNA by an siRNA containing a given target sequence can also be evaluated with animal models of neovascularization, such as the ROP or CNV mouse models. For example, areas of neovascularization in an ROP or CNV mouse can be measured before and after administration of an siRNA and, in some embodiments, compared to an untreated animal. A reduction in the areas of neovascularization in these models upon administration of the siRNA indicates, in some embodiments, the down-regulation of the target mRNA (see Example 6 below).

As discussed above, the siRNA is capable of targeting and causing the RNAi-mediated degradation of VEGF and its isoforms as well as Flt-1 or Flk-1/KDR mRNA, or alternative splice forms, mutants or cognates thereof, preferably VEGF, and more preferably human VEGF. Degradation of the target mRNA by the present siRNA reduces the production of a functional gene product from the VEGF and its isoforms as well as Flt-1 or Flk-1/KDR genes. Thus, another embodiment of the present invention provides a method of inhibiting expression of VEGF and its isoforms, such as $VEGF_{121}$ (SEQ ID NO: 2), $VEGF_{165}$ (SEQ ID NO: 3), and $VEGF_{189}$ (SEQ ID NO: 4), $VEGF_{206}$ (SEQ ID NO: 5; GenBank Accession No. CS245579), $VEGF_{183}$ (GenBank Accession No. AJ010438), $VEGF_{148}$ (GenBank Accession No. AF091352), and/or $VEGF_{145}$ (GenBank Accession No. CS245578), as well as Flt-1 or Flk-1/KDR in a subject, comprising administering an effective amount of an siRNA to the subject, such that the target mRNA is degraded. As the products of the VEGF and its isoforms as well as Flt-1 and Flk-1/KDR genes are required for initiating and maintaining angiogenesis, another embodiment of the present invention provides a method of inhibiting angiogenesis in a subject by the RNAi-mediated degradation of the target mRNA by the present siRNA.

RNAi-mediated degradation of the target mRNA can be detected by measuring levels of the target mRNA or protein in the cells of a subject, using standard techniques for isolating and quantifying mRNA or protein as described above.

Inhibition of angiogenesis can be evaluated by directly measuring the progress of pathogenic or nonpathogenic angiogenesis in a subject; for example, by observing the size of a neovascularized area before and after treatment with the siRNA. An inhibition of angiogenesis is indicated if the size of the neovascularized area stays the same or is reduced. Techniques for observing and measuring the size of neovascularized areas in a subject are within the skill in the art; for example, areas of choroid neovascularization can be observed, for example, by fluorescein angiography.

Inhibition of angiogenesis can also be inferred through observing a change or reversal in a pathogenic condition associated with the angiogenesis. For example, in ARMD, a slowing, halting or reversal of vision loss indicates an inhibition of angiogenesis in the choroid. For tumors, a slowing, halting or reversal of tumor growth, or a slowing or halting of tumor metastasis, indicates an inhibition of angiogenesis at or near the tumor site. Inhibition of non-pathogenic angiogenesis can also be inferred from, for example, fat loss or a reduction in cholesterol levels upon administration of the siRNA.

It is understood that the siRNA can degrade the target mRNA (and thus inhibit angiogenesis) in substoichiometric amounts. Without wishing to be bound by any theory, it is believed that the siRNA causes degradation of the target mRNA in a catalytic manner. Thus, compared to standard anti-angiogenic therapies, significantly less siRNA needs to be delivered at or near the site of neovascularization to have a therapeutic effect.

One skilled in the art can readily determine an effective amount of the siRNA to be administered to a given subject, by taking into account factors such as the size and weight of the subject; the extent of the neovascularization or disease penetration; the age, health and sex of the subject; the route of administration; and whether the administration is regional or systemic. Generally, an effective amount of the siRNA comprises an intercellular concentration at or near the neovascularization site of from about 1 nanomolar (nM) to about 100 nM, preferably from about 2 nM to about 50 nM, more preferably from about 2.5 nM to about 10 nM. It is contemplated that greater or lesser amounts of siRNA can be administered.

The present methods can be used to inhibit angiogenesis which is non-pathogenic; i.e., angiogenesis which results from normal processes in the subject. Examples of non-pathogenic angiogenesis include endometrial neovascularization, and processes involved in the production of fatty tissues or cholesterol. Thus, the invention provides a method for inhibiting non-pathogenic angiogenesis, e.g., for controlling weight or promoting fat loss, for reducing cholesterol levels, or as an abortifacient.

The present methods can also inhibit angiogenesis which is associated with an angiogenic disease; i.e., a disease in which pathogenicity is associated with inappropriate or uncontrolled angiogenesis. For example, most cancerous solid tumors generate an adequate blood supply for themselves by inducing angiogenesis in and around the tumor site. This tumor-induced angiogenesis is often required for tumor growth, and also allows metastatic cells to enter the bloodstream.

Other angiogenic diseases include diabetic retinopathy, age-related macular degeneration (ARMD), psoriasis, rheumatoid arthritis and other inflammatory diseases. These diseases are characterized by the destruction of normal tissue by newly formed blood vessels in the area of neovascularization. For example, in ARMD, the choroid is invaded and destroyed by capillaries. The angiogenesis-driven destruction of the choroid in ARMD eventually leads to partial or full blindness.

Preferably, an siRNA is used to inhibit the growth or metastasis of solid tumors associated with cancers; for example breast cancer, lung cancer, head and neck cancer, brain cancer, abdominal cancer, colon cancer, colorectal cancer, esophagus cancer, gastrointestinal cancer, glioma, liver cancer, tongue cancer, neuroblastoma, osteosarcoma, ovarian cancer, pancreatic cancer, prostate cancer, retinoblastoma, Wilm's tumor, multiple myeloma; skin cancer (e.g., melanoma), lymphomas and blood cancer.

More preferably, an siRNA is used to inhibit choroidal neovascularization in age-related macular degeneration.

For treating angiogenic diseases, the siRNA can administered to a subject in combination with a pharmaceutical agent which is different from the present siRNA. Alternatively, the siRNA can be administered to a subject in combination with another therapeutic method designed to treat the angiogenic disease. For example, the siRNA can be administered in combination with therapeutic methods currently employed for treating cancer or preventing tumor metastasis (e.g., radiation therapy, chemotherapy, and surgery). For treating tumors, the siRNA is preferably administered to a subject in combination with radiation therapy, or in combination with chemotherapeutic agents such as cisplatin, carboplatin, cyclophosphamide, 5-fluorouracil, adriamycin, daunorubicin or tamoxifen.

In the present methods, the present siRNA can be administered to the subject either as naked siRNA, in conjunction with a delivery reagent, or as a recombinant plasmid or viral vector which expresses the siRNA.

Suitable delivery reagents for administration in conjunction with the present siRNA include, but not limited to, the Mirus Transit TKO lipophilic reagent; lipofectin; lipofectamine; cellfectin; or polycations (e.g., polylysine), or liposomes. In some embodiments the delivery reagent is RiboJuice™ (Novagen), a siRNA transfection reagent, which comprises amine and lipid based reagents. A preferred delivery reagent is a liposome. In some embodiments, the siRNA is delivered free of a liposomal delivery agent.

Liposomes can aid in the delivery of the siRNA to a particular tissue, such as retinal or tumor tissue, and can also increase the blood half-life of the siRNA. Liposomes suitable for use in the invention are formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example as described in Szoka et al. (1980), *Ann. Rev. Biophys. Bioeng.* 9: 467; and U.S. Pat. Nos. 4,235,871, 4,501,728, 4,837,028, and 5,019,369, the entire disclosures of which are herein incorporated by reference.

Preferably, the liposomes encapsulating the present siRNA comprises a ligand molecule that can target the liposome to a particular cell or tissue at or near the site of angiogenesis. Ligands which bind to receptors prevalent in tumor or vascular endothelial cells, such as monoclonal antibodies that bind to tumor antigens or endothelial cell surface antigens, are preferred.

Particularly preferably, the liposomes encapsulating the present siRNA are modified so as to avoid clearance by the mononuclear macrophage and reticuloendothelial systems, for example by having opsonization-inhibition moieties bound to the surface of the structure. In one embodiment, a liposome of the invention can comprise both opsonization-inhibition moieties and a ligand.

Opsonization-inhibiting moieties for use in preparing the liposomes of the invention are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer which significantly decreases the uptake of the liposomes by the macrophage-monocyte system ("MMS") and reticuloendothelial system ("RES"); e.g., as described in U.S. Pat. No. 4,920,016, the entire disclosure of which is herein incorporated by reference. Liposomes modified with opsonization-inhibition moieties thus remain in the circulation much longer than unmodified liposomes. For this reason, such liposomes are sometimes called "stealth" liposomes.

Stealth liposomes are known to accumulate in tissues fed by porous or "leaky" microvasculature. Thus, target tissue characterized by such microvasculature defects, for example solid tumors, will efficiently accumulate these liposomes; see Gabizon, et al. (1988), *P.N.A.S., USA,* 18: 6949-53. In addition, the reduced uptake by the RES lowers the toxicity of stealth liposomes by preventing significant accumulation in the liver and spleen. Thus, liposomes of the invention that are modified with opsonization-inhibition moieties can deliver the present siRNA to tumor cells.

Opsonization inhibiting moieties suitable for modifying liposomes are preferably water-soluble polymers with a number-average molecular weight from about 500 to about 40,000 daltons, and more preferably from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside $GM_1$. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups.

Preferably, the opsonization-inhibiting moiety is a PEG, PPG, or derivatives thereof. Liposomes modified with PEG or PEG-derivatives are sometimes called "PEGylated liposomes."

The opsonization inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using $Na(CN)BH_3$ and a solvent mixture such as tetrahydrofuran and water in a 30:12 ratio at 60° C.

Recombinant plasmids which express siRNA are discussed above. Such recombinant plasmids can also be administered directly or in conjunction with a suitable delivery reagent, including the Mirus Transit LT1 lipophilic reagent; lipofectin; lipofectamine; cellfectin; polycations (e.g., polylysine) or liposomes. Recombinant viral vectors which express siRNA are also discussed above, and methods for delivering such vectors to an area of neovascularization in a patient are within the skill in the art.

The siRNA can be administered to the subject by any means suitable for delivering the siRNA to the cells of the tissue at or near the area of neovascularization. For example, the siRNA can be administered by gene gun, electroporation, or by other suitable parenteral or enteral administration routes.

Suitable enteral administration routes include oral, rectal, or intranasal delivery.

Suitable parenteral administration routes include intravascular administration (e.g. intravenous bolus injection, intravenous infusion, intra-arterial bolus injection, intra-arterial infusion and catheter instillation into the vasculature); peri- and intra-tissue administration (e.g., peri-tumoral and intra-tumoral injection, intra-retinal injection or subretinal injection); subcutaneous injection or deposition including subcutaneous infusion (such as by osmotic pumps); direct (e.g., topical) application to the area at or near the site of neovascularization, for example by a catheter or other placement device (e.g., a corneal pellet or a suppository, eye-dropper, or an implant comprising a porous, non-porous, or gelatinous material); and inhalation. Suitable placement devices include the ocular implants described in U.S. Pat. Nos. 5,902,598 and 6,375,972, and the biodegradable ocular implants described in U.S. Pat. No. 6,331,313, the entire disclosures of which are herein incorporated by reference. Such ocular implants are available from Control Delivery Systems, Inc. (Watertown, Mass.) and Oculex Pharmaceuticals, Inc. (Sunnyvale, Calif.).

In a preferred embodiment, injections or infusions of the siRNA are given at or near the site of neovascularization. More preferably, the siRNA is administered topically to the eye, e.g. in liquid or gel form to the lower eye lid or conjunctival cul-de-sac, as is within the skill in the art (see, e.g., Acheampong A A et al, 2002, *Drug Metabol. and Disposition* 30: 421-429, the entire disclosure of which is herein incorporated by reference).

Typically, the siRNA is administered topically to the eye in amounts of from about 5 microliters to about 75 microliters, for example from about 7 microliters to about 50 microliters, preferably from about 10 microliters to about 30 microliters. It is understood that topical instillation in the eye of siRNA in volumes greater than 75 microliters can result in loss of siRNA from the eye through spillage and drainage. Thus, it is preferable to administer a high concentration of siRNA (e.g., 100-1000 nM) in as small a volume as possible.

A particularly preferred parenteral administration route is intraocular administration. It is understood that intraocular administration of the present siRNA can be accomplished by injection or direct (e.g., topical) administration to the eye, as long as the administration route allows the siRNA to enter the eye. In addition to the topical routes of administration to the eye described above, suitable intraocular routes of administration include intravitreal, intraretinal, subretinal, subtenon, peri- and retro-orbital, trans-corneal and trans-scleral administration. Such intraocular administration routes are within the skill in the art; see, e.g., and Acheampong A A et al, 2002, supra; and Bennett et al. (1996), *Hum. Gene Ther.* 7: 1763-1769 and Ambati J et al., 2002, *Progress in Retinal and Eye Res.* 21: 145-151, the entire disclosures of which are herein incorporated by reference. In another preferred embodiment, the siRNA is administered by intravitreal injection.

The siRNA can be administered in a single dose or in multiple doses. Where the administration of the siRNA is by infusion, the infusion can be a single sustained dose or can be delivered by multiple infusions. Injection of the agent directly into the tissue is at or near the site of neovascularization preferred. Multiple injections of the agent into the tissue at or near the site of neovascularization are particularly preferred.

One skilled in the art can also readily determine an appropriate dosage regimen for administering the siRNA to a given subject. For example, the siRNA can be administered to the subject once, such as by a single injection or deposition at or near the neovascularization site. Alternatively, the siRNA can be administered to a subject multiple times daily or weekly. For example, the siRNA can be administered to a subject once weekly for a period of from about three to about twenty-eight weeks, and alternatively from about seven to about ten weeks. In a certain dosage regimen, the siRNA is injected at or near the site of neovascularization (e.g., intravitreally) once a week for seven weeks. It is understood that periodic administrations of the siRNA for an indefinite length of time may be necessary for subjects suffering from a chronic neovascularization disease, such as wet ARMD or diabetic retinopathy.

Where a dosage regimen comprises multiple administrations, it is understood that the effective amount of siRNA administered to the subject can comprise the total amount of siRNA administered over the entire dosage regimen.

The siRNA are preferably formulated as pharmaceutical compositions prior to administering to a subject, according to techniques known in the art. Pharmaceutical compositions of the present invention are characterized as being at least sterile and pyrogen-free. As used herein, "pharmaceutical formulations" include formulations for human and veterinary use. Methods for preparing pharmaceutical compositions of the invention are within the skill in the art, for example as described in *Remington's Pharmaceutical Science*, 17th ed., Mack Publishing Company, Easton, Pa. (1985), the entire disclosure of which is herein incorporated by reference.

In one embodiment, the pharmaceutical formulations comprise an siRNA (e.g., 0.1 to 90% by weight), or a physiologically acceptable salt thereof, mixed with a physiologically acceptable carrier medium. Preferred physiologically acceptable carrier media are water, buffered water, saline solutions (e.g., normal saline or balanced saline solutions such as Hank's or Earle's balanced salt solutions), 0.4% saline, 0.3% glycine, hyaluronic acid and the like.

Pharmaceutical compositions can also comprise conventional pharmaceutical excipients and/or additives. Suitable pharmaceutical excipients include stabilizers, antioxidants, osmolality adjusting agents, buffers, and pH adjusting agents. Suitable additives include physiologically biocompatible buffers (e.g., tromethamine hydrochloride), additions of chelants (such as, for example, DTPA or DTPA-bisamide) or calcium chelate complexes (as for example calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For topical administration to the eye, conventional intraocular delivery reagents can be used. For example, pharmaceutical compositions of the invention for topical intraocular delivery can comprise saline solutions as described above, corneal penetration enhancers, insoluble particles, petrolatum or other gel-based ointments, polymers which undergo a viscosity increase upon instillation in the eye, or mucoadhesive polymers. Preferably, the intraocular delivery reagent increases corneal penetration, or prolongs preocular retention of the siRNA through viscosity effects or by establishing physicochemical interactions with the mucin layer covering the corneal epithelium.

Suitable insoluble particles for topical intraocular delivery include the calcium phosphate particles described in U.S. Pat. No. 6,355,271 of Bell et al., the entire disclosure of which is herein incorporated by reference. Suitable polymers which undergo a viscosity increase upon instillation in the eye include polyethylenepolyoxypropylene block copolymers such as poloxamer 407 (e.g., at a concentration of 25%), cellulose acetophthalate (e.g., at a concentration of 30%), or a low-acetyl gellan gum such as Gelrite® (available from CP Kelco, Wilmington, Del.). Suitable mucoadhesive polymers include hydrocolloids with multiple hydrophilic functional groups such as carboxyl, hydroxyl, amide and/or sulfate groups; for example, hydroxypropylcellulose, polyacrylic acid, high-molecular weight polyethylene glycols (e.g., >200,000 number average molecular weight), dextrans, hyaluronic acid, polygalacturonic acid, and xylocan. Suitable corneal penetration enhancers include cyclodextrins, benzalkonium chloride, polyoxyethylene glycol lauryl ether (e.g., Brij® 35), polyoxyethylene glycol stearyl ether (e.g., Brij® 78), polyoxyethylene glycol oleyl ether (e.g., Brij® 98), ethylene diamine tetraacetic acid (EDTA), digitonin, sodium taurocholate, saponins and polyoxyethylated castor oil such as Cremaphor EL.

For solid compositions, conventional nontoxic solid carriers can be used; for example, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can comprise any of the carriers and excipients listed above and 10-95%, preferably 25%-75%, of one or more siRNA. A pharmaceutical composition for aerosol (inhalational) administration can comprise 0.01-20% by weight, preferably 1%-10% by weight, of one or more siRNA encapsulated in a liposome as described above, and propellant. A carrier can also be included as desired; e.g., lecithin for intranasal delivery.

The invention will now be illustrated with the following non-limiting examples.

Example 1 siRNA Transfection and Hypoxia Induction In Vitro siRNA Design—A 19 nt sequence located 329 nt from the 5' end of human VEGF mRNA was chosen as a target sequence: AAACCTCACCAAGGCCAGCAC (SEQ ID NO: 51). To ensure that it was not contained in the mRNA from any other genes, this target sequence was entered into the BLAST search engine provided by NCBI. The use of the BLAST algorithm is described in Altschul et al. (1990), *J. Mol. Biol.* 215: 403-410 and Altschul et al. (1997), *Nucleic Acids Res.* 25: 3389-3402, the disclosures of which are herein incorporated by reference in their entirety. As no other mRNA was found which contained the target sequence, an siRNA duplex was synthesized to target this sequence (Dharmacon Research, Inc., Lafayette, Colo.).

The siRNA duplex had the following sense and antisense strands.

```
sense:
5'-accucaccaaggccagcacTT-3'.        (SEQ ID NO: 77)

antisense:
5'-gugcuggccuuggugagguTT-3'.        (SEQ ID NO: 78)
```

Together, the siRNA sense and antisense strands formed a 19 nt double-stranded siRNA with TT 3' overhangs (shown in bold) on each strand. This siRNA was termed "Candidate 5" or "Cand5." Other siRNA which target human VEGF mRNA were designed and tested as described for Cand5 (bevasiranib).

An siRNA targeting the following sequence in green fluorescent protein (GFP) mRNA was used as a nonspecific control: GGCTACGTCCAGCGCACC (SEQ ID NO: 79). The siRNA was purchased from Dharmacon (Lafayette, Colo.).

siRNA Transfection and Hypoxia Induction In Vitro—Human cell lines (293; Hela and ARPE19) were separately seeded into 24-well plates in 250 microliters of complete DMEM medium one day prior to transfection, so that the cells were ~50% confluent at the time of transfection. Cells were transfected with 2.5 nM Cand5 siRNA, and with either no siRNA or 2.5 nM non-specific siRNA (targeting GFP) as controls. Transfections were performed in all cell lines with the "Transit TKO Transfection" reagent, as recommended by the manufacturer (Mirus).

Twenty four hours after transfection, hypoxia was induced in the cells by the addition of deferoxamine mesylate to a final concentration of 130 micromolar in each well. Twenty four hours post-transfection, the cell culture medium was removed from all wells, and a human VEGF ELISA (R&D systems, Minneapolis, Minn.) was performed on the culture medium as described in the Quantikine human VEGF ELISA protocol available from the manufacturer, the entire disclosure of which is herein incorporated by reference.

Figure 1B:
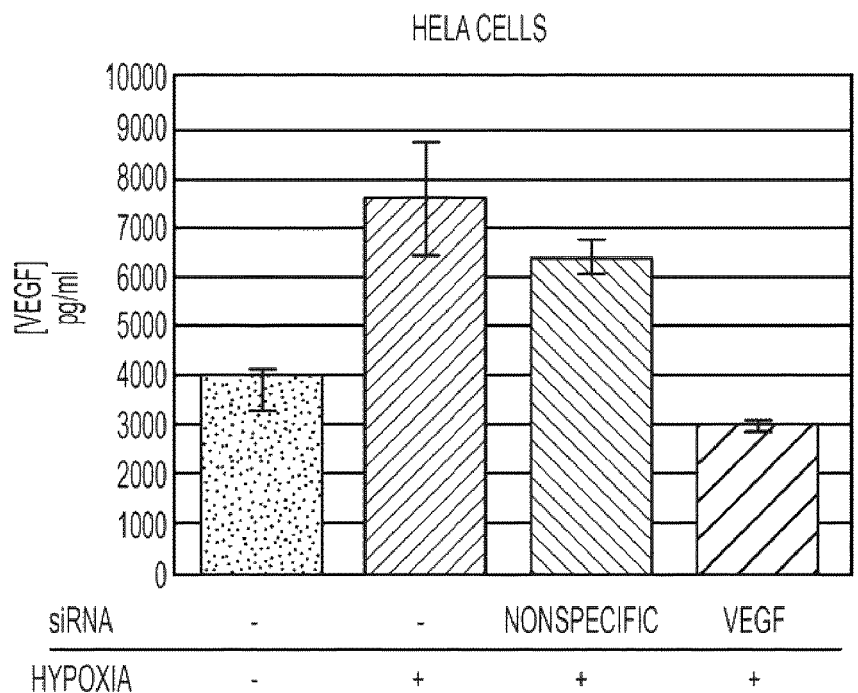

As can be seen in FIG. 1, RNAi degradation induced by Cand5 siRNA significantly reduces the concentration of VEGF produced by the hypoxic 293 and HeLa cells. There was essentially no difference in the amount of VEGF produced by hypoxic cells treated with either no siRNA or the non-specific siRNA control. Similar results were also seen with human ARPE19 cells treated under the same conditions. Thus, RNA interference with VEGF-targeted siRNA disrupts the pathogenic up-regulation of VEGF in human cultured cells in vitro.

The experiment outlined above was repeated on mouse NIH 3T3 cells using a mouse-specific VEGF siRNA (see Example 6 below), and VEGF production was quantified with a mouse VEGF ELISA (R&D systems, Minneapolis, Minn.) as described in the Quantikine mouse VEGF ELISA protocol available from the manufacturer, the entire disclosure of which is herein incorporated by reference. Results similar to those reported in FIG. 1 for the human cell lines were obtained.

Example 2

Effect of Increasing siRNA Concentration on VEGF Production in Human Cultured Cells The experiment outlined in Example 1 was repeated with human 293, HeLa and ARPE19 cells using a range of siRNA concentrations from 10 nM to 50 nM. The ability of the Cand5 siRNA to down-regulate VEGF production increased moderately up to approximately 13 nM siRNA, but a plateau effect was seen above this concentration. These results highlight the catalytic nature of siRNA-mediated RNAi degradation of mRNA, as the plateau effect appears to reflect VEGF production from the few cells not transfected with the siRNA. For the majority of cells which had been transfected with the siRNA, the increased VEGF mRNA production induced by the hypoxia is outstripped by the siRNA-induced degradation of the target mRNA at siRNA concentrations greater than about 13 nM.

Example 3

Specificity of siRNA Targeting

NIH 3T3 mouse fibroblasts were grown in 24-well plates under standard conditions, so that the cells were ~50% confluent one day prior to transfection. The human VEGF siRNA Cand5 was transfected into a NIH 3T3 mouse fibroblasts as in Example 1. Hypoxia was then induced in the transfected cells, and murine VEGF concentrations were measured by ELISA as in Example 1.

Figure 2:
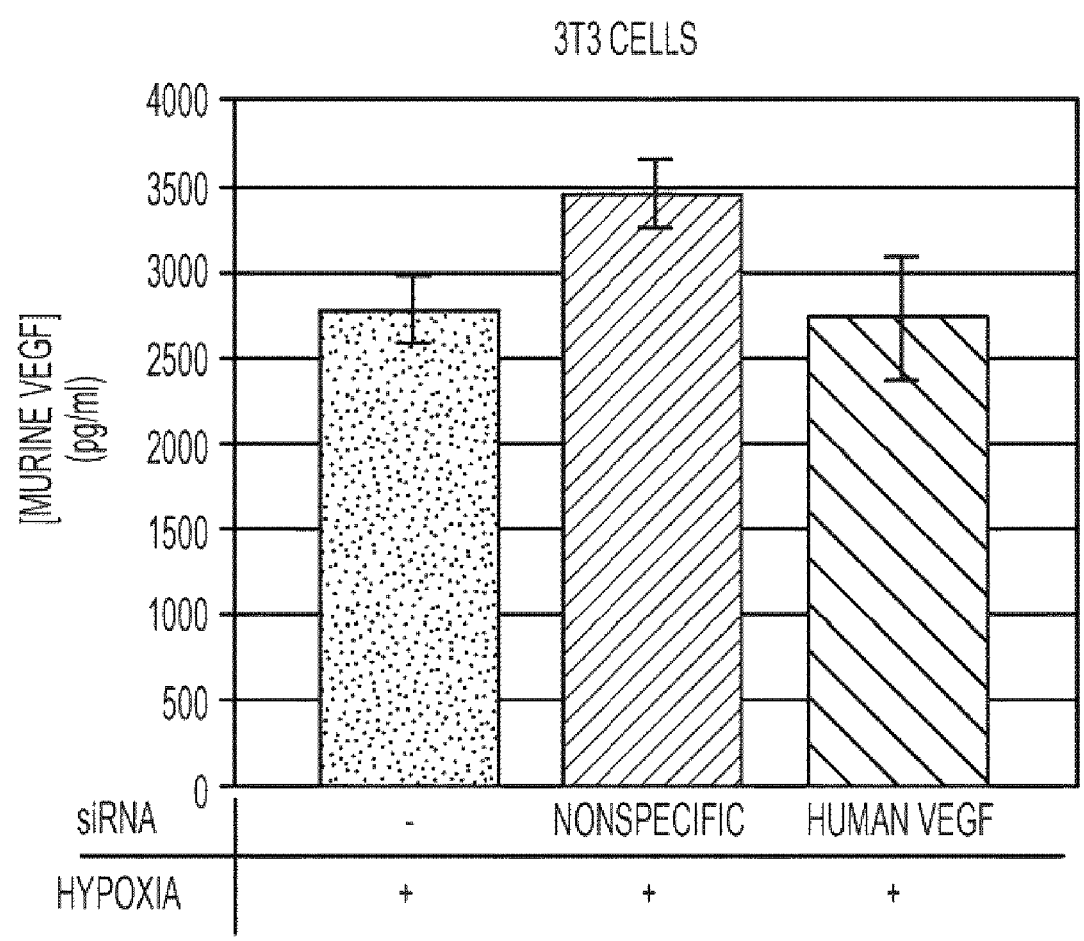
FIG. 2 is a histogram of murine VEGF concentration (in pg/ml) in hypoxic NIH 3T3 cells treated with no siRNA ("−"); nonspecific siRNA ("nonspecific"); or siRNA targeting human VEGF mRNA ("VEGF"). Each bar represents the average of six experiments and the error is the standard deviation of the mean.
Figure 3:
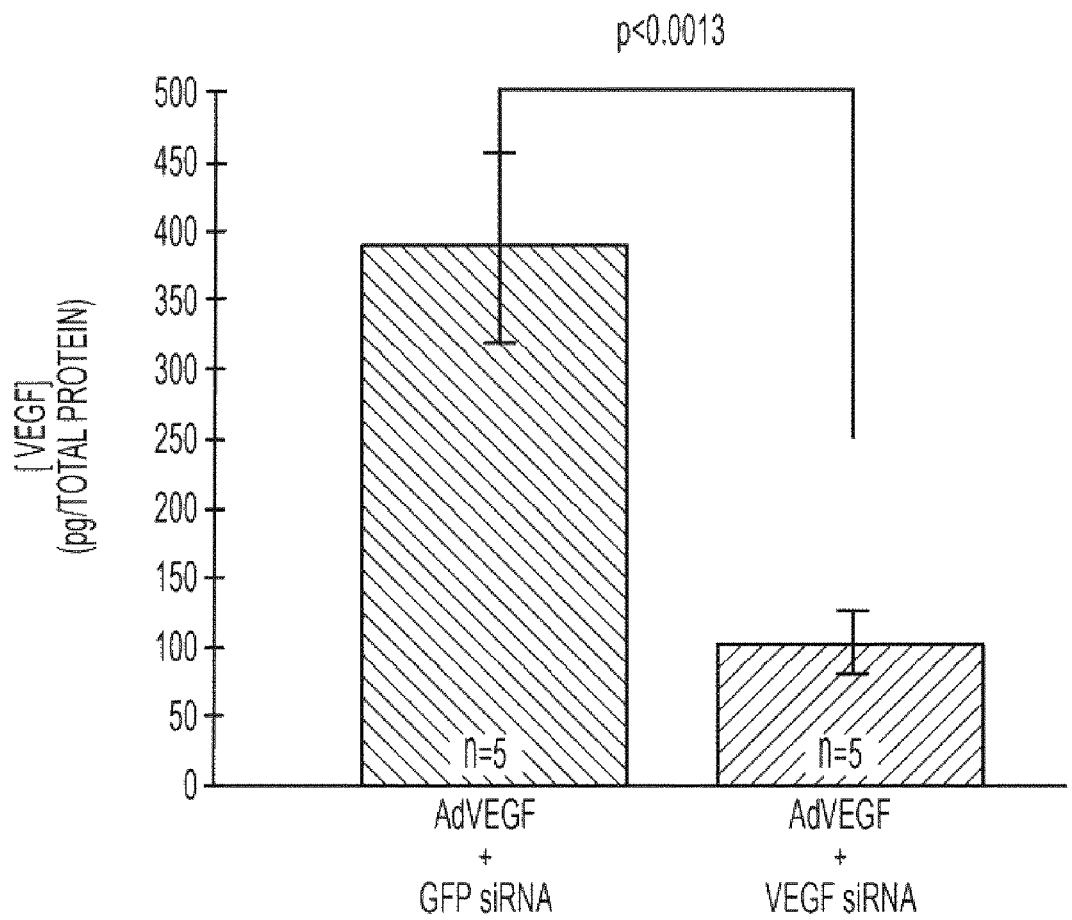
FIG. 3 is a histogram of human VEGF concentration (pg/total protein) in retinas from mice injected with adenovirus expressing human VEGF ("AdVEGF") in the presence of either GFP siRNA (dark gray bar) or human VEGF siRNA (light grey bar). Each bar represents the average of 5 eyes and the error bars represent the standard error of the mean.

The sequence targeted by the human VEGF siRNA Cand5 differs from the murine VEGF mRNA by one nucleotide. As can be seen in FIG. 2, the human VEGF siRNA has no affect on the ability of the mouse cells to up-regulate mouse VEGF after hypoxia. These results show that siRNA induced RNAi degradation is sequence-specific to within a one nucleotide resolution.

Example 4

In Vivo delivery of siRNA to Murine Retinal Pigment Epithelial Cells

VEGF is upregulated in the retinal pigment epithelial (RPE) cells of human patients with age-related macular degeneration (ARMD). To show that functional siRNA can be delivered to RPE cells in vivo, GFP was expressed in mouse retinas with a recombinant adenovirus, and GFP expression was silenced with siRNA. The experiment was conducted as follows.

One eye from each of five adult C57/Black6 mice (Jackson Labs, Bar Harbor, Me.) was injected subretinally as described in Bennett et al. (1996), supra., with a mixture containing ~1×10⁸ particles of adenovirus containing eGFP driven by the CMV promoter and 20 picomoles of siRNA targeting eGFP conjugated with transit TKO reagent (Mirus).

As positive control, the contralateral eyes were injected with a mixture containing ~1×10⁸ particles of adenovirus containing eGFP driven by the CMV promoter and 20 picomoles of siRNA targeting human VEGF conjugated with transit TKO reagent (Mirus). Expression of GFP was detected by fundus ophthalmoscopy 48 hours and 60 hours after injection. Animals were sacrificed at either 48 hours or 60 hours post-injection. The eyes were enucleated and fixed in 4% paraformaldehyde, and were prepared either as flat mounts or were processed into 10 micron cryosections for fluorescent microscopy.

No GFP fluorescence was detectable by ophthalmoscopy in the eyes which received the siRNA targeted to GFP mRNA in 4 out of 5 mice, whereas GFP fluorescence was detectable in the contralateral eye which received the non-specific control siRNA. A representative flat mount analyzed by fluorescence microscopy showed a lack of GFP fluorescence in the eye which received GFP siRNA, as compared to an eye that received the non-specific control siRNA. Cryosections of another retina showed that the recombinant adenovirus efficiently targets the RPE cells, and when the adenovirus is accompanied by siRNA targeted to GFP mRNA, expression of the GFP transgene is halted.

While there is some GFP fluorescence detectable by fluorescence microscopy in eyes that received siRNA targeted to GFP mRNA, the fluorescence is greatly suppressed as compared to controls that received non-specific siRNA. These data demonstrate that functional siRNA can be delivered in vivo to RPE cells.

Example 5

In Vivo Expression and siRNA-Induced RNAi Degradation of Human VEGF in Murine Retinas In order to demonstrate that siRNA targeted to VEGF functioned in vivo, an exogenous human VEGF expression cassette was delivered to mouse RPE cells via an adenovirus by subretinal injection, as in Example 4. One eye received Cand5 siRNA, and the contralateral eye received siRNA targeted to GFP mRNA. The animals were sacrificed 60 hours post-injection, and the injected eyes were removed and snap frozen in liquid $N_2$ following enucleation. The eyes were then homogenized in lysis buffer, and total protein was measured using a standard Bradford protein assay (Roche, Germany). The samples were normalized for total protein prior to assaying for human VEGF by ELISA as described in Example 1.

Figure 4:
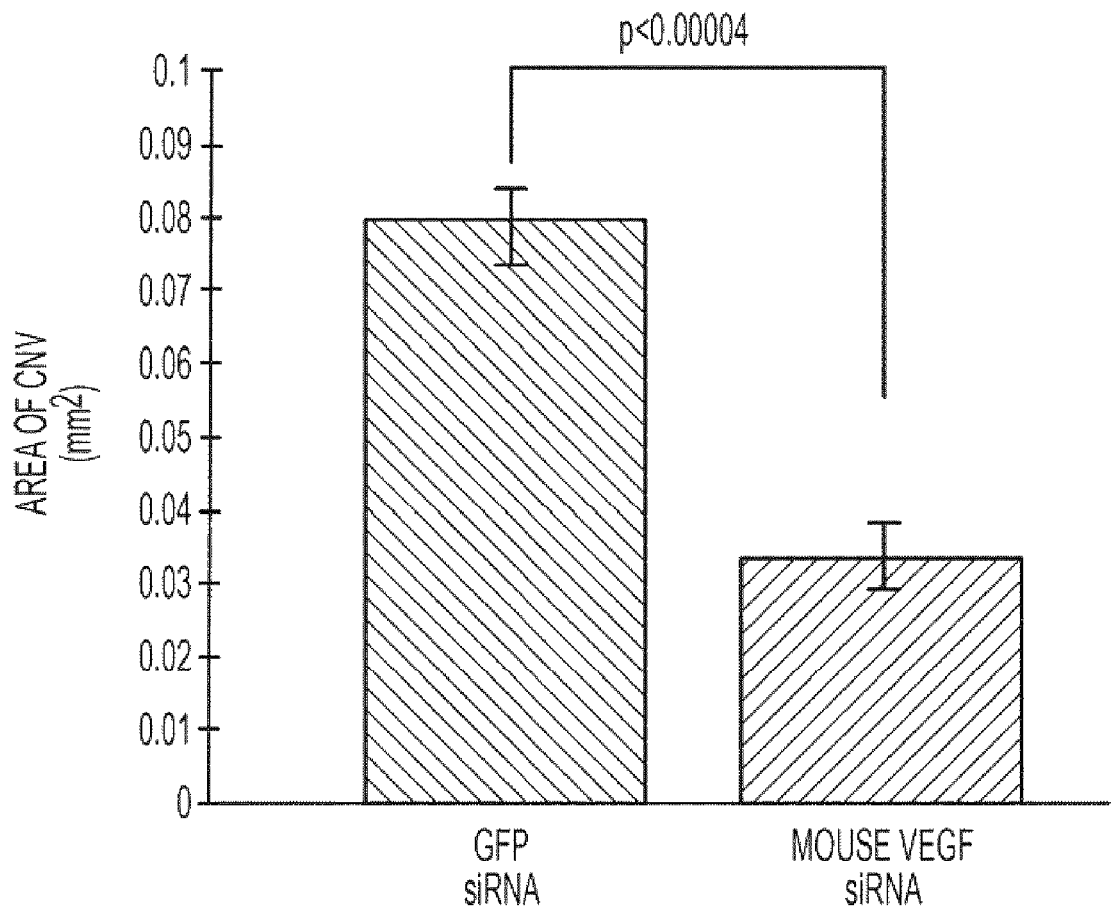
FIG. 4 is a histogram showing the mean area (in mm$^2$) of laser-induced CNV in control eyes given subretinal injections of GFP siRNA (N=9; "GFP siRNA"), and in eyes given subretinal injections of mouse VEGF siRNA (N=7; "Mouse VEGF siRNA"). The error bars represent the standard error of the mean.

The expression of VEGF was somewhat variable from animal to animal. The variability of VEGF levels correlated well to those observed in the GFP experiments of Example 4, and can be attributed to some error from injection to injection, and the differential ability of adenovirus to delivery the target gene in each animal. However, there was a significant attenuation of VEGF expression in each eye that received VEGF siRNA, as compared to the eyes receiving the non-specific control siRNA (FIG. 4). These data indicate that the Cand5 siRNA was potent and effective in silencing human VEGF expression in murine RPE cells in vivo.

Example 6

Inhibition of Choroidal Neovascularization in the Mouse CNV Model

There is evidence that choroidal neovascularization in ARMD is due to the upregulation of VEGF in the RPE cells. This human pathologic condition can be modeled in the mouse by using a laser to burn a spot on the retina ("laser photo-coagulation" or "laser induction"). During the healing process, VEGF is believed to be up-regulated in the RPE cells of the burned region, leading to re-vascularization of the choroid. This model is called the mouse choroidal neovascularization ("CNV") model.

For rescue of the mouse CNV model, a mouse siRNA was designed that incorporated a one nucleotide change from the human "Cand5" siRNA from Example 1. The mouse siRNA specifically targeted mouse VEGF mRNA at the sequence AAACCUCACCAAAGCCAGCAC (SEQ ID NO: 80). Other siRNA that target mouse VEGF were also designed and tested. The GFP siRNA used as a nonspecific control in Example 1 was also used as a non-specific control here.

Twenty four hours after laser induction, one eye from each of eleven adult C57/Black6 mice (Jackson Labs, Bar Harbor, Me.) was injected subretinally with a mixture containing ~1×10⁸ particles of adenovirus containing LacZ driven by the CMV promoter and 20 picomoles of siRNA targeting mouse VEGF conjugated with transit TKO reagent (Mirus), as in Example 4. As a control, contralateral eyes received a mixture containing ~1×10⁸ particles of adenovirus containing LacZ driven by the CMV promoter and 20 picomoles of siRNA targeting GFP conjugated with transit TKO reagent (Mirus).

Fourteen days after the laser treatment, the mice were perfused with fluorescein and the area of neovascularization was measured around the burn spots. Areas of the burn spots in the contra-lateral eye were used as a control. The site of neovascularization around the burn spots in animals that received siRNA targeting mouse VEGF was, on average, ¼ the area of the control areas. These data support the use of VEGF-directed siRNA (also called "anti-VEGF siRNA") for therapy of ARMD.

Example 7

Generation of an Adeno-Associated Viral Vector for Expression of siRNA

A "cis-acting" plasmid for generating a recombinant AAV vector for delivering an siRNA was generated by PCR based subcloning, essentially as described in Samulski R et al. (1987), supra. The cis-acting plasmid was called "pAAV-siRNA."

Figure 5:
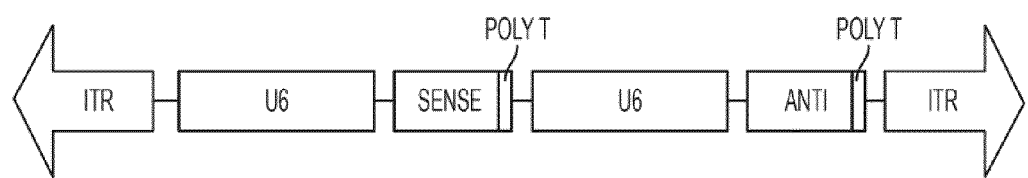
FIG. 5 is a schematic representation of pAAVsiRNA, a cis-acting plasmid used to generate a recombinant AAV viral vector of the invention. "ITR": AAV inverted terminal repeats; "U6": U6 RNA promoters; "Sense": siRNA sense coding sequence; "Anti": siRNA antisense coding sequence; "PolyT": polythymidine termination signals.

The rep and cap genes of psub201 were replaced with the following sequences in this order: a 19 nt sense RNA strand coding sequence in operable connection with a polyT termination sequence under the control of a human U6 RNA promoter, and a 19 nt antisense RNA strand coding sequence in operable connection with a polyT termination sequence under the control of a human U6 RNA promoter. A schematic representation of pAAVsiRNA is given if FIG. 5.

A recombinant AAV siRNA vector was obtained by transfecting pAAVsiRNA into human 293 cells previously infected with E1-deleted adenovirus, as described in Fisher K J et al. (1996), supra. The AAV rep and cap functions were provided by a trans-acting plasmid pAAV/Ad as described in Samulski R et al. (1989), supra. Production lots of the recombinant AAV siRNA vector were titered according to the number of genome copies/ml, as described in Fisher K J et al. (1996), supra.

Example 8

VEGF-Directed siRNA Inhibits Experimental Choroidal Neovascularization

The ability of murine VEGF-directed siRNA to inhibit experimental laser-induced choroidal neovascularization (CNV) in mice was tested as follows.

The retinas of adult female C57BL/6 mice were laser photocoagulated using an 810 nm diode laser (75 um, 140 mw, 0.10 seconds) (OcuLight Six; IRIS Medical, Mountain View, Calif.). Three laser spots were applied to both eyes of each mouse. Thirty-six hours following laser photocoagulation, an siRNA targeted to mouse VEGF ("mVEGF1.siRNA") was delivered subretinally or intravitreally to one eye of each mouse. For subretinal injection, the siRNA was conjugated with Transit TKO transfection reagent (Mirus) and mixed with recombinant adenovirus (rAdenovirus). For intravitreal injection, the siRNA was delivered in the absence of transfection reagent and rAdenovirus. As a control, the contralateral eyes of each mouse received subretinal or intravitreal injections of identical formulations with an siRNA targeted to GFP ("GFP1.siRNA"), which has no homology to mouse VEGF.

Figure 6A:
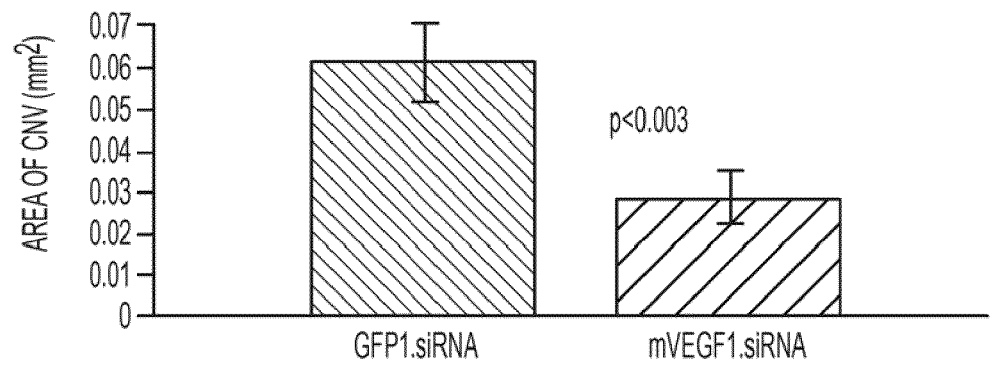
FIG. 6 shows histograms of the mean area (in mm$^2$) of laser-induced CNV in treatment in mouse eyes injected (A) subretinally or (B) intravitreally with a mouse anti-VEGF siRNA ("mVEGF1.siRNA") or control siRNA ("GFP1.siRNA"). The error bars represent the standard error of the mean. (C) is a histogram of the mean area (in mm$^2$) of laser-induced CNV in mouse eyes injected intravitreally with: phosphate-buffered saline with no siRNA at 1 day post-laser induction ("PBS"; CNV area measured at 14 days post-laser induction); control siRNA at 14 days post-laser induction ("GFP1.siRNA"; CNV area measured at 21 days post-laser induction); or a mouse anti-VEGF siRNA at 14 days post-laser induction ("mVEGF1.siRNA"; CNV area measured at 21 days post-laser induction). The error bars represent the standard error of the mean.
Figure 6B:
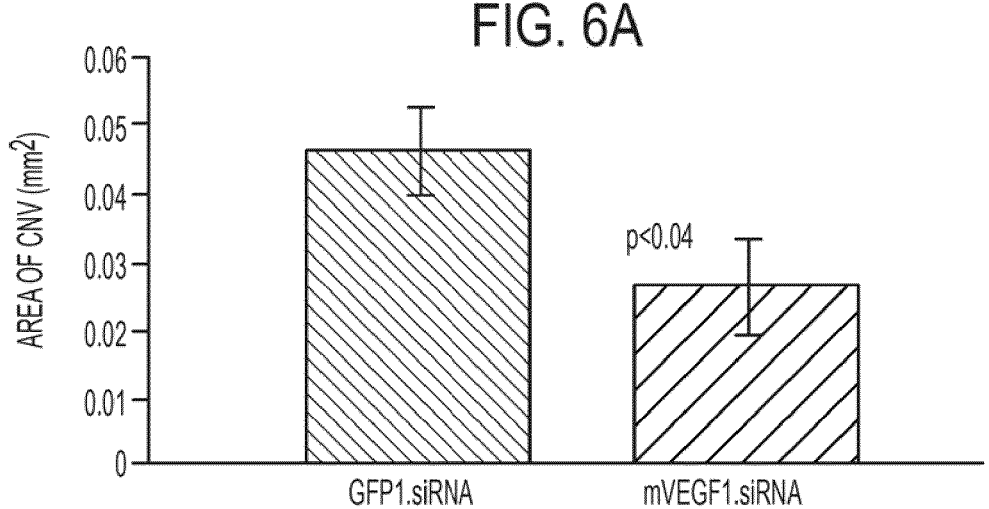

Fourteen days following laser treatment, all animals were perfused with high molecular weight FITC-dextran, choroidal flat mounts were prepared as described above, and the flat mounts were photographed and analyzed microscopically in a masked fashion. The area of CNV in each flat mount was measured with Openlab software (Improvision, Boston, Mass.). The mean areas of CNV in eyes treated with mVEGF1.siRNA were significantly smaller than those areas from GFP1.siRNA-treated eyes for both subretinal (FIG. 6A; $P<0.003$) and intravitreal (FIG. 6B; $P<0.04$) delivery.

In a second experiment, the retinas of adult female C57BL/6 mice were laser photocoagulated as described above, and the animals were divided into control and test groups. One day following laser photocoagulation, phosphate buffered saline was delivered intravitreally to the animals of the control group, which were perfused with dextran-fluorescein 14 days after laser treatment. Choroidal flat mounts were then prepared and the areas of CNV in each flat mount were measured as above.

Fourteen days following laser photocoagulation, mVEGF1.siRNA was delivered by intravitreal injection into one eye of each mouse in the test group. Contralateral eyes were injected with GFP1.siRNA as a control. The test group animals were perfused with high molecular weight dextran-fluorescein 21 days after laser treatment. Choroidal flat mounts were then prepared and the areas of CNV in each flat mount were measured, as above.

Figure 6C:
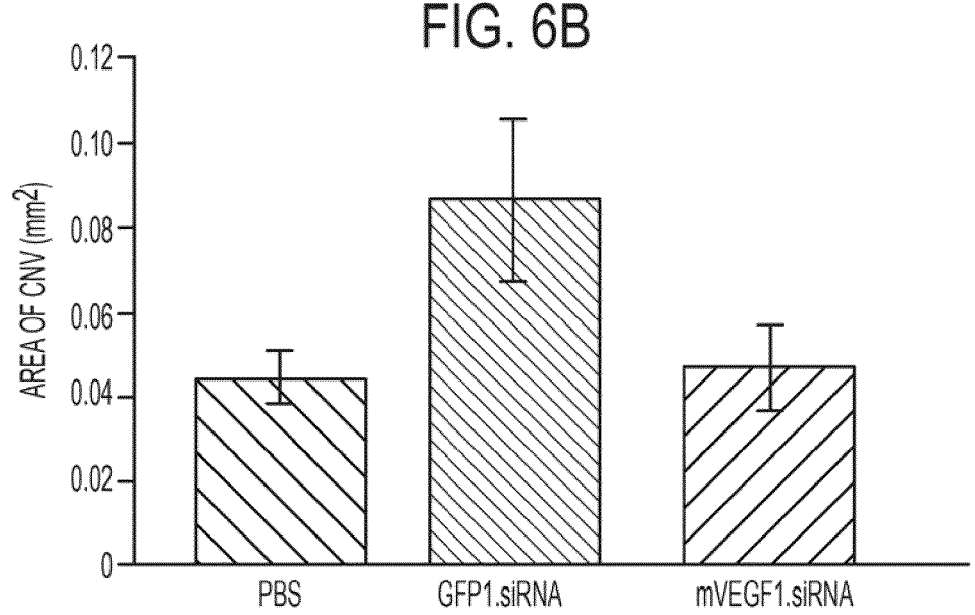

In this latter experiment, the anti-VEGF siRNA was administered during CNV growth, as opposed to before CNV growth, and thus is more representative of the condition of human patients presenting with wet AMD. As can be seen from FIG. 6, the mean areas of CNV in mVEGF1.siRNA-treated eyes were significantly smaller than those areas measured in GFP1.siRNA-treated eyes (FIG. 6C; $P<0.05$). The mean areas of CNV in mVEGF1.siRNA-treated eyes at day 21 and control ("PBS") eyes at day 14 were not significantly different (FIG. 6C; $P=0.469$).

The results of these experiments indicate that age-related macular degeneration can be treated with anti-VEGF siRNA.

Example 9

In Vivo RNA Interference of Human VEGF Induced by Anti-VEGF siRNA in Murine RPE Cells The ability of Cand5 siRNA to induce RNAi of VEGF in vivo over time was evaluated as follows.

AAV.CMV.VEGF, which expresses human VEGF from an adeno-associated viral vector, was generously provided by Dr. A. Auricchio. AAV.CMV.VEGF was injected subretinally and bilaterally in eyes of five C57Bl/6 mice. Twenty-eight days after injection of AAV.CMV.VEGF, Cand5 siRNA was delivered by intravitreal injection into one eye and control GFP1.siRNA was delivered by intravitreal injection in the contralateral eye of each animal.

At day 0 (pre-siRNA injection), and at 6, 10 and 14 days after siRNA injection, the mice were sacrificed and the eyes were snap frozen in liquid nitrogen following enucleation. The eyes were then homogenized in lysis buffer (Roche, Basel, Switzerland), and total protein was measured using a Bradford assay, as in Example 5 above. Two mice were used for the 0 day time point (n=2), and three mice each were used for the 6, 10 and 14 day time points (n=3). The samples were normalized for total protein prior to assaying for human VEGF by ELISA, according to the manufacturer's recommendations (R&D systems, Minneapolis, Minn.). Percent of VEGF (% VEGF) for each mouse was calculated as the concentration of VEGF ("[VEGF]") in the eye injected with Cand5 divided by the [VEGF] in the eye injected with GFP1.siRNA, multiplied by 100.

Figure 7:
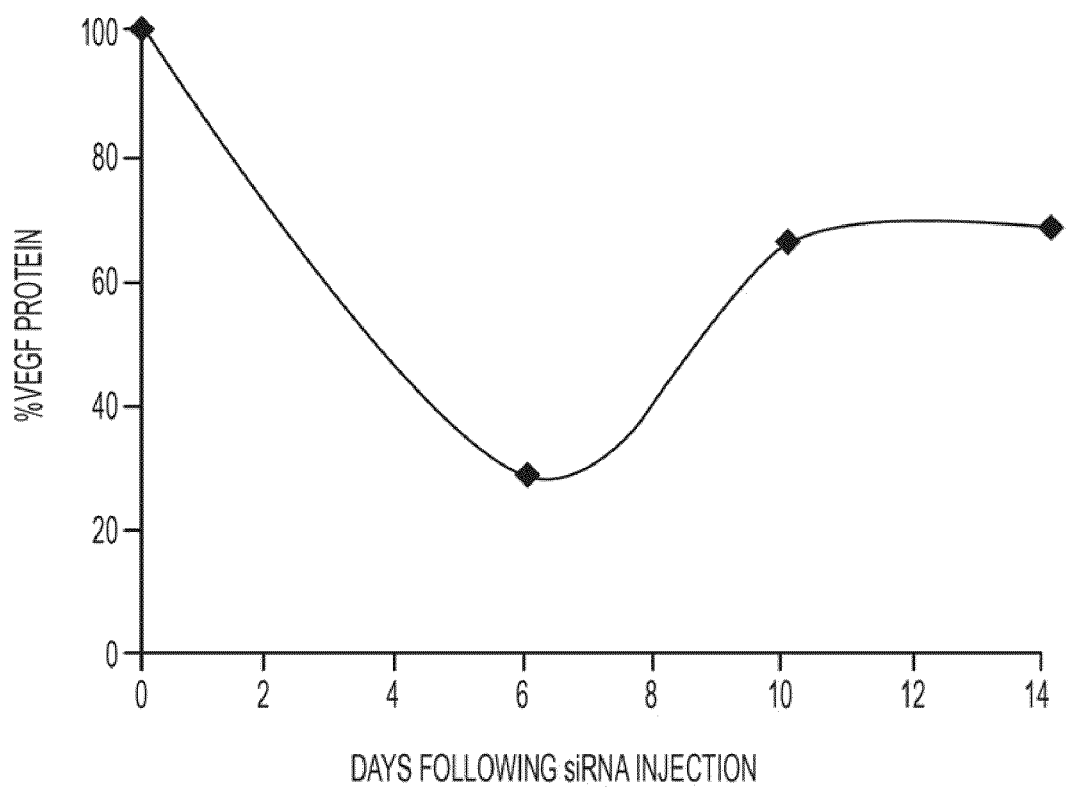
FIG. 7 is a graph of the percent of VEGF ("% VEGF") protein in mouse eyes injected sub-retinally with human anti-VEGF siRNA ("Cand5") and control siRNA ("GFP1.siRNA") at 0 (n=2; pre-siRNA injection), 6 (n=3), 10 (n=3) and 14 (n=3) days post-injection. % VEGF=([VEGF] in the Cand5 eye/[VEGF] in the GFP1.siRNA eye)*100.

As can be seen from FIG. 7, a single injection of Cand5 induced an RNAi-mediated decrease in VEGF levels of approximately 70% by day 6 post-siRNA injection, with a reduction in VEGF production of approximately 35% continuing through at least day 14 post-siRNA injection. These results indicate that siRNA directed against human VEGF is capable of inducing RNAi of human VEGF in vivo for a sustained period of time.

Example 10

In Vivo RNA Interference of VEGF in Monkeys with Anti-VEGF siRNA

The objectives of this study were to determine the safety and efficacy of Cand5 when administered by single intravitreal injection to male cynomolgus monkeys following induction of CNV. Cand5 was administered in the vehicle control article to naive male cynomolgus monkeys in the following dose levels: 0 mg/eye (control), 0.07 mg/eye, 0.18 mg/eye, 0.35 mg/eye and, and 0.70 mg/eye.

CNV was induced by laser treatment to the maculae of both eyes of each animal, and the doses of Cand5 were given shortly following laser treatment. The animals were evaluated for changes in clinical signs, body weight and ocular condition (extensive ophthalmic examinations, electroretinography and tonometry). Fluorescein angiography was performed and blood samples were collected. At the end of the study (Day 44), all animals were euthanized and a complete gross necropsy was performed. Selected tissues were collected and preserved for histopathologic evaluation.

No adverse systemic or local (ocular) effects of Cand5 were detected when monkeys were administered a single intravitreal injection into both eyes at doses up to 0.70 mg/eye following laser lesioning of the macula and during subsequent development of CNV.

Example 11

In Vitro RNA Interference of VEGF with Anti-VEGF siRNA in Human Embryonic Kidney 293 Cells Human embryonic kidney 293 cells (obtained from ATCC, Manassas, Va.) were cultured in Dulbecco's Modified Eagle Medium (DMEM; obtained from Cellgro, Herndon, Va.) with 10% fetal bovine serum (FBS; from JRH Biosciences, Lenexa, Kans.) and an antibiotic-antimycotic reagent, used for the prevention of cell culture growth contaminants (from Gibco, Carlsbad, Calif.).

siRNAs were synthesized by Integrated DNA Technologies (Coralville, Iowa). The siRNA target sequences are shown in Table 2. An additional siRNA was used in this study that targets the gene of enhanced green fluorescent protein (EGFP) as a negative control.

TABLE 2

| Name | GC Content | Nucleotide Start Site | Target Sequence 5'-3' |
|---|---|---|---|
| hVEGF#1 | 58% | 92 | aaggaggagggcagaatcatc (SEQ ID NO: 81) |
| hVEGF#2 | 42% | 124 | aagttcatggatgtctatcag (SEQ ID NO: 47) |
| hVEGF#3 | 58% | 162 | aatcgagaccctggtggacat (SEQ ID NO: 48) |
| hVEGF#4 | 42% | 301 | aacatcaccatgcagattatg (SEQ ID NO: 50) |
| hVEGF#5 | 58% | 338 | aaggccagcacataggagaga (SEQ ID NO: 52) |
| hVEGF#6 | 42% | 380 | aatgtgaatgcagaccaaaga (SEQ ID NO: 82) |
| hVEGF#7 | 37% | 396 | aaagaaagatagagcaagaca (SEQ ID NO: 56) |
| hVEGF#8 | 32% | 450 | aaagcatttgtttgtacaaga (SEQ ID NO: 83) |
| hVEGF#9 | 42% | 467 | aagatccgcagacgtgtaaat (SEQ ID NO: 84) |
| hVEGF#10 | 53% | 498 | aaacacacactcgcgttgcaa (SEQ ID NO: 85) |
| Cand5 | 63% | 328 | aaacctcaccaaggccagcac (SEQ ID NO: 51) | siRNA Transfection and Hypoxia Induction In Vitro. Human 293 cells were cultured in 24 well plates at 37° C. with 5% $CO_2$ overnight. The next day, transfections were performed when cells were about 50%-70% confluent. Cells were transfected with siRNAs directed against human VEGF. siRNAs were mixed in a CaPi reagent and added to 20 µl of 250 mM $CaCl_2$ solution. The siRNA/$CaCl_2$ mixture was added drop-wise to 20 µl of 2× Hanks Balanced Salt Solution (HBS), while mixing by vortex. The siRNA/$CaCl_2$/HBS complex was added directly to the medium in each well (300 µL/well). After a 4-hour incubation at 37° C., the medium was removed, and the cells were further incubated with 10% DMSO-containing serum-free medium (300 µL/well at room temperature for 1-2 minutes). This medium was then removed, and the cells were fed again with growth medium (500 µL/well). Negative controls included transfection reagent lacking siRNA and nonspecific siRNA (EGFP1 siRNA). For screening experiments siRNAs were used at a concentration of 25 nM. For dose response experiments, siRNAs were used at concentrations of 1 nM, 5 nM and 25 nM. Hypoxia was induced with desferrioxamine at a final concentration of 130 uM 4 hours after transfection was performed. Desferrioxamine mimics a hypoxic state, as it is proposed to disrupt normal oxygen-sensing pathways in mammalian cells by inhibiting heme-$Fe^{2+}$ interactions.

VEGF Protein Quantification. Approximately 48 hours post transfection, the supernatant was removed from all wells and a human VEGF ELISA (R & D systems, Minneapolis, Minn.) was performed on the 293 cells as described in the Quantikine human VEGF ELISA protocol. VEGF-specific antibody was added to each well causing color development in proportion to the amount of VEGF bound to the plate. ELISA results were read on an AD340 plate reader at 450 nm (Beckman Coulter).

Figure 8:
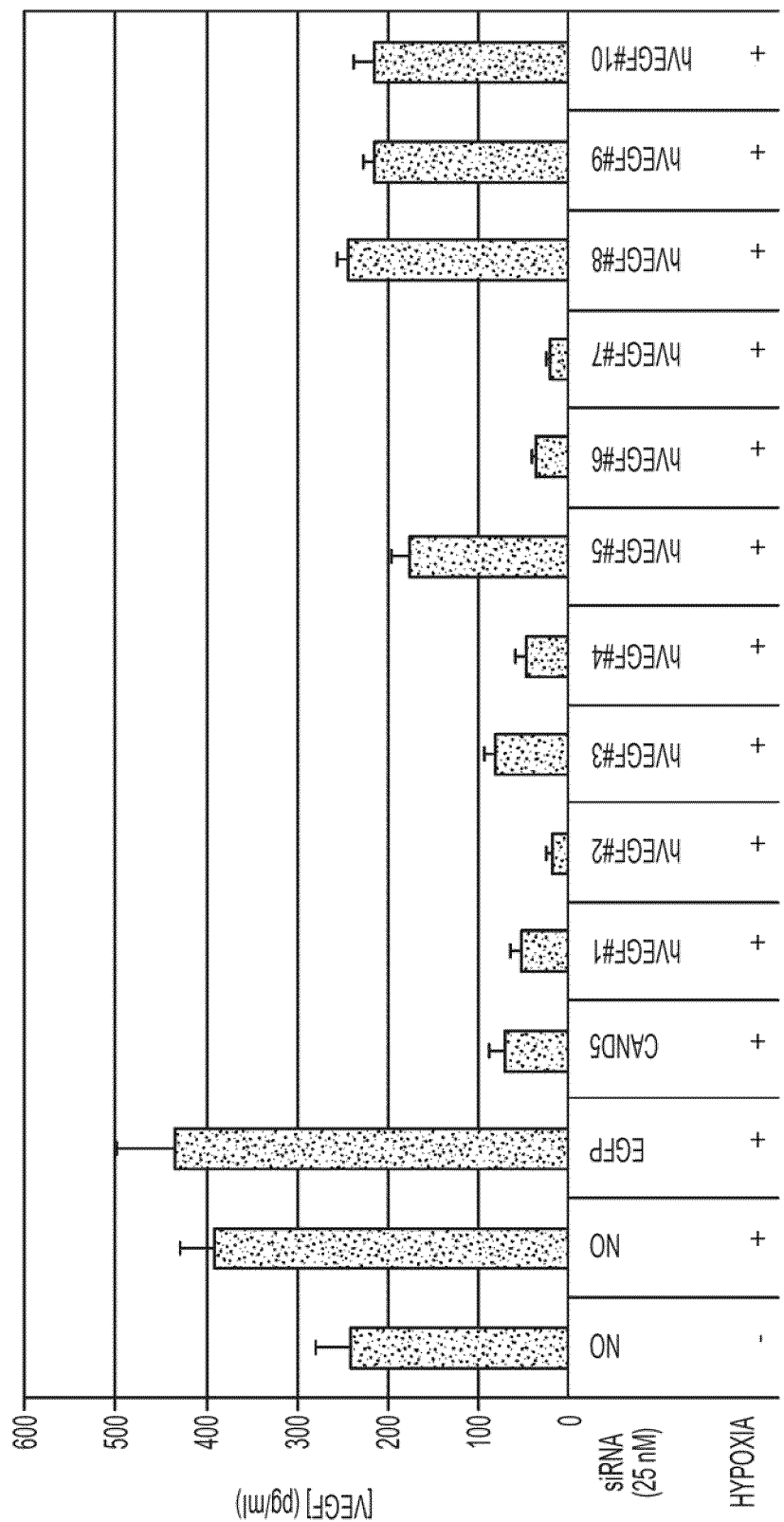
FIG. 8 is a graph of hVEGF protein levels in 293 cells transfected with transfected with human VEGF siRNAs, non-specific siRNA (EGFP siRNA) or mock transfections without siRNA.
Figure 9:
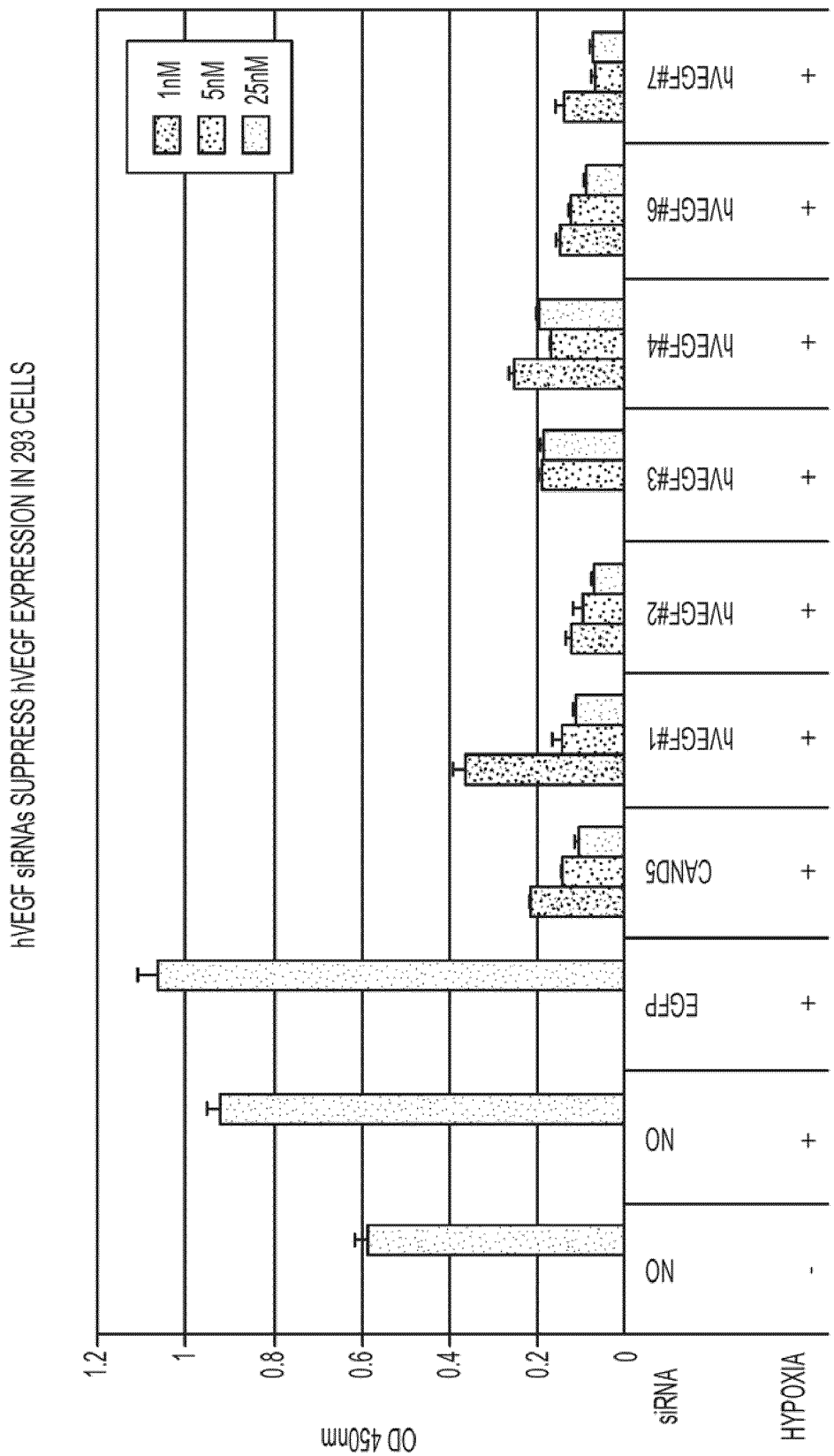
FIG. 9 is a graph of the dose response studies with Cand5 (bevasrianib), hVEGF#1, hVEGF#2, hVEGF#3, hVEGF#4, hVEGF#6 and hVEGF#7.

Results. Human VEGF siRNAs Suppresses Hypoxia-Induced Up-regulation of Human VEGF Protein in 293 Cells. Human VEGF was upregulated by the desferrioxamine-mediated induction of hypoxia. Readings of OD 450 nm reflected the human VEGF protein levels in cell samples. The hypoxia-induced increase of hVEGF protein levels were significantly reduced in cells transfected with all of the human VEGF siRNAs (FIG. 8). No effect on hVEGF levels were observed with transfections with nonspecific siRNA (EGFP siRNA) or mock transfections without siRNA. Dose response studies were performed on Cand5, hVEGF#1, hVEGF#2, hVEGF#3, hVEGF#4, hVEGF#6 and hVEGF#7 (FIG. 9).

Example 12

In Vitro RNA Interference of VEGF Isoforms $VEGF_{165b}$ has been identified as an endogenous anti-angiogenic VEGF isoform. siRNA were designed to selectively inhibit certain VEGF isoforms, such as $VEGF_{165}$, but spare $VEGF_{165b}$.

Methods: ARPE19 cells were seeded in 24 well plates (50,000 cells per well). Eighteen to twenty-four hours post-seeding, cells were 50-75% confluent and used for transfection. Fourteen human VEGF-A specific siRNAs were designed and tested. Cells were transfected with the siRNAs (25 nM) using RiboJuice™ siRNA Transfection Reagent (Novagen) following the manufacturer's protocol. Specifically, for a single well of cells, 40.5 µL it serum free OPTI-MEM® was pipetted into an eppendorf tube then 2 µL of RiboJuice™ was added to the OPTI-MEM. The solution was mixed by gentle vortexing and centrifuged briefly to collect contents at bottom of the tube and incubated at room temperature for 5 minutes. siRNA (7.5 µL of a 1 µM stock) was added to the RiboJuice™/medium mix and gently mixed and briefly centrifuged to collect contents at the bottom of the tube. The mixture was incubated at room temperature for 15 minutes. During the incubation, media was removed from cells and replaced with 250 µL of fresh complete ARPE19 growth media (DMEM/F12; 10% FBS, 1% penicillin/streptomycin). After the 15 minute incubation the siRNA/RiboJuice™/medium mixture (50 µL) was added dropwise to the cells. The final concentration of siRNA in the 300 µL volume was 25 nM. Cells were maintained at 37° C., 5% $CO_2$ for 24 hours. In additional experiments, reactions were scaled up to transfect cells in triplicate wells with each siRNA. 24 hours post-transfection, the transfection mixture was removed and the cells were treated with 500 µLs of serum free DMEM/F12, DMEM/F12 containing 10 ng/mL human recombinant TGFβII or DMEM/F12 containing 10 ng/mL TGFβII and 5 µg/mL cycloheximide The cells were returned to 37° C. and 5% $CO_2$ for an additional 24 hours. Afterwards, the media was removed from the cells and analyzed for protein expression by ELISA (Quantikine human VEGF ELISA kit (R&D Systems)). Media was removed from cells and collected in eppendorf tubes and placed on ice and immediately analyzed for VEGF protein via ELISA, or stored at −80° C. and analyzed for VEGF protein at a later time point.

Based on these results, a select number of siRNA candidates were put through an additional transfection screen. Cells were collected, RNA extracted, and semi-quantitative RT-PCR was performed to determine the siRNAs' inhibitory effect on $VEGF_{165}$, $VEGF_{165b}$, $VEGF_{121}$ and $VEGF_{189}$. GAPDH housekeeping gene expression was used as a control. Specifically, after removing the media from the wells, 200 µLs of lysis/binding solution from the RNAqueous Kit (Ambion) was added to each well. RNA was quantified via spectrophotometry (OD 260 nM). The lysed cells were collected and RNA was extracted following the manufacturer's protocol. RNA was reverse transcribed using SuperScript™ III Reverse Transcriptase (Invitrogen) according to the manufacturer's protocol. cDNA was analyzed for GAPDH, $VEGF_{165}$, $VEGF_{165b}$, $VEGF_{121}$ and $VEGF_{189}$ using PCR. Primers used for PCR are shown in Table 3.

TABLE 3

| Primer Name | Description | Sequence 5'-3' |
|---|---|---|
| P121 | Reverse primer VEGF121 | GGCTTGTCACATTTTTCTTG (SEQ ID NO: 131) |
| P165 | Reverse primer VEGF165 | CCCACAGGGATTTTCTTGTC (SEQ ID NO: 132) |
| P189 | Reverse primer VEGF189 | CTTTCCCTTTCCTCGAACTG (SEQ ID NO: 133) |
| hVEGF-E | Forward primer used for VEGF121, VEGF165 & VEGF 189 | GCTACTGCCATCCAATCGAG (SEQ ID NO: 134) |
| P165bR | Reverse primer for VEGF165b | GTCTTTCCTGGTGAGAGATC (SEQ ID NO: 135) |
| hVEGF-A | Forward primer for VEGF165b | CTGTCTTGGGTGCATTGGAG (SEQ ID NO: 136) |
| GAPDH-B | Reverse primer GAPDH | GAGGCAGGGATGATGTTCTG (SEQ ID NO: 137) |
| GAPDH-A | Forward primer GAPDH | CATGGCAAATTCCATGGCAC (SEQ ID NO: 138) |

For PCR analysis, 3 µL cDNA was combined with 1 µL of each appropriate forward (10 µM) and reverse primer (10 µM) primer and 45 µL of Platinum PCR Supermix (Invitrogen) such that the final concentration of each primer was 200 nM. The cDNA was amplified in a thermocycler with the following PCR conditions:
Step 1: 94° C. for 2 minutes
Step 2: 94° C. for 15 seconds
Step 3: 55° C. for 30 seconds
Step 4: 72° C. for 30 seconds
Step 5: Repeat steps 2-4 30 times for GAPDH, $VEGF_{165}$, $VEGF_{121}$ and $VEGF_{189}$ or 35 times for $VEGF_{165b}$
Step 6: 72° C. for 10 minutes
Step 7: 4° C.

PCR product was then visualized on a 2% agarose gel prepared in 1×TAE buffer.

Figure 12:
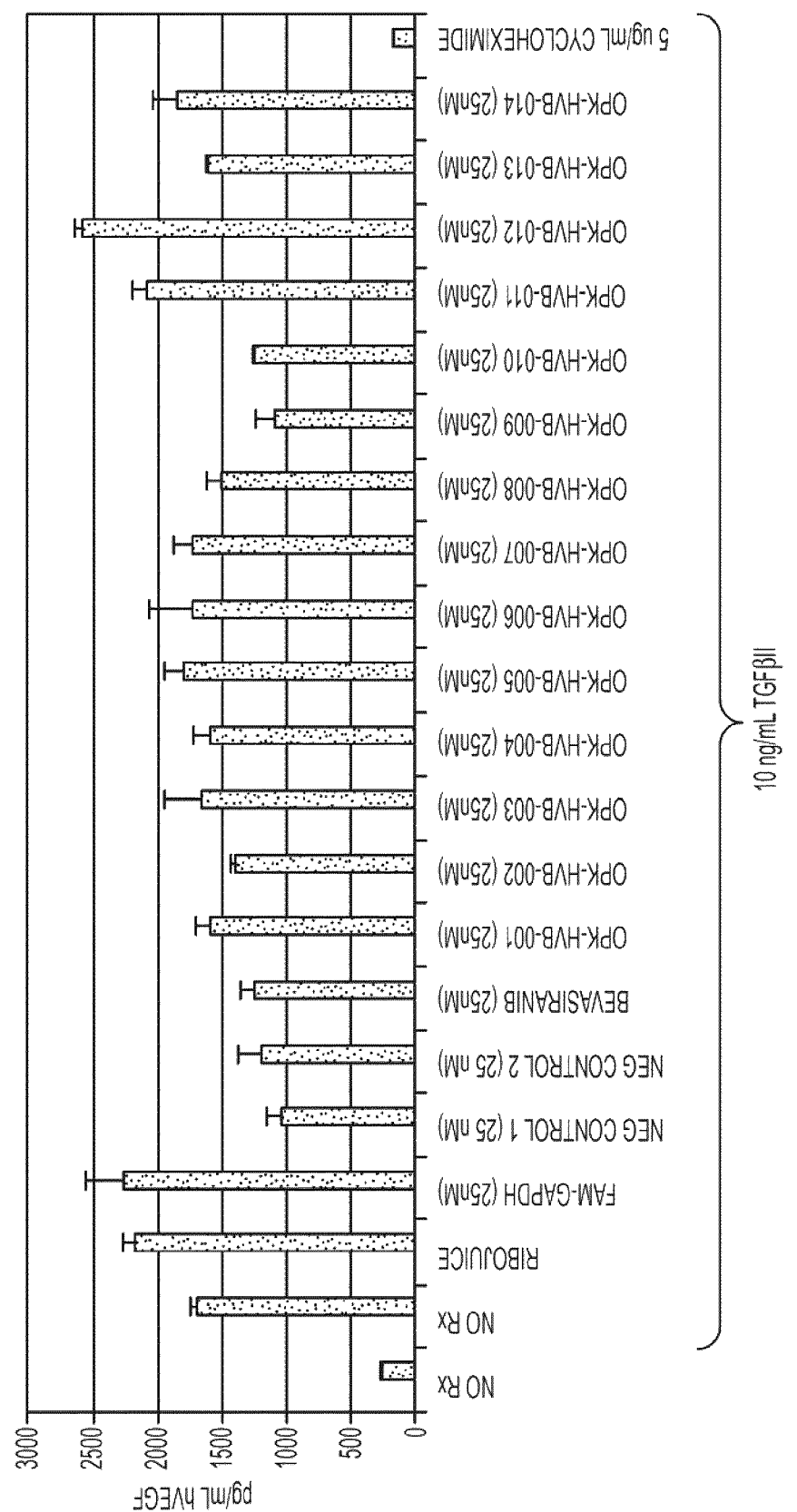
FIG. 12 depicts the amount of VEGF protein expressed for various siRNAs targeting the VEGF$_{165}$ exon 7/8 junction.
Figure 13:
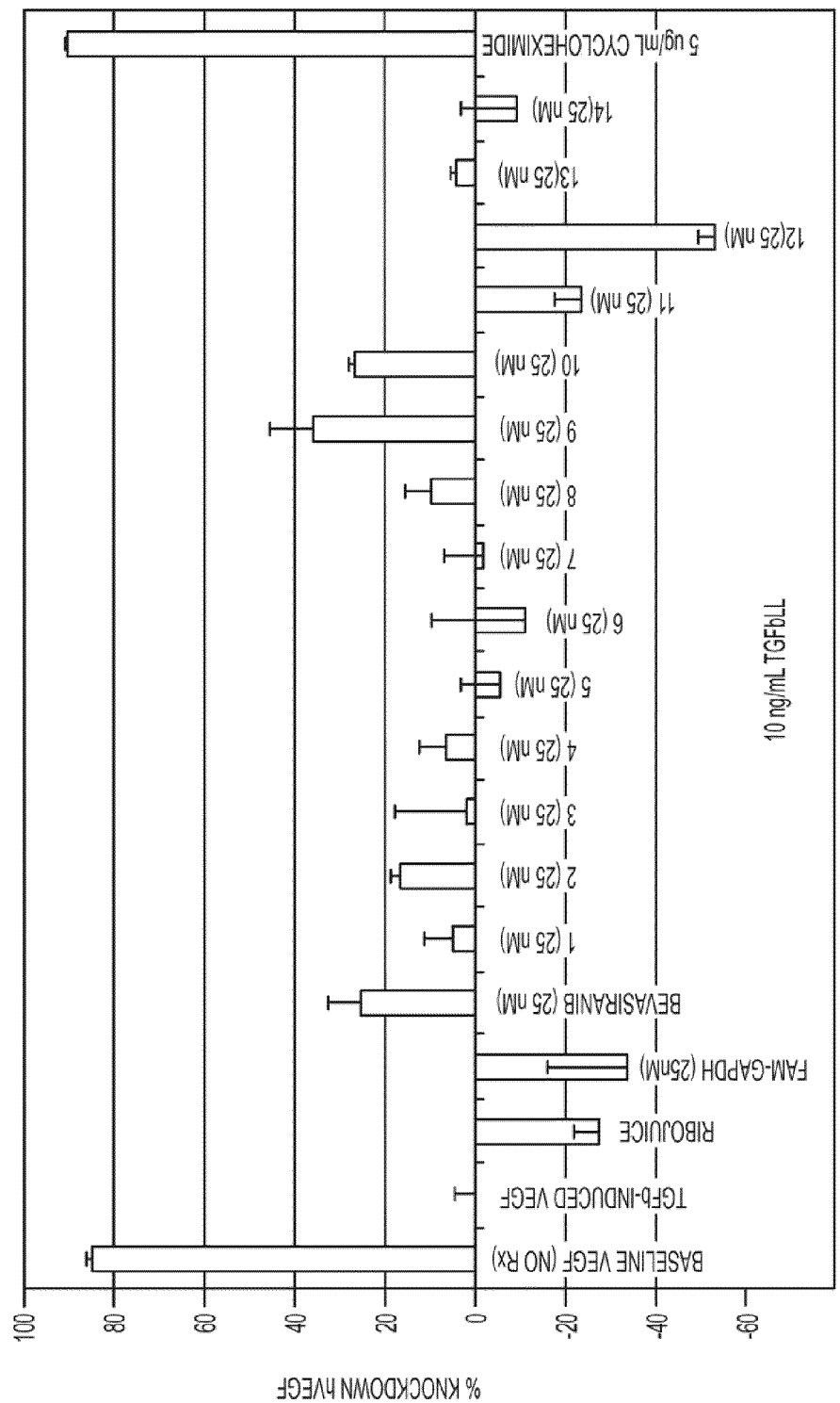
FIG. 13 depicts the percent knockdown of human VEGF protein for various siRNAs targeting the VEGF$_{165}$ exon 7/8 junction.
Figure 14:
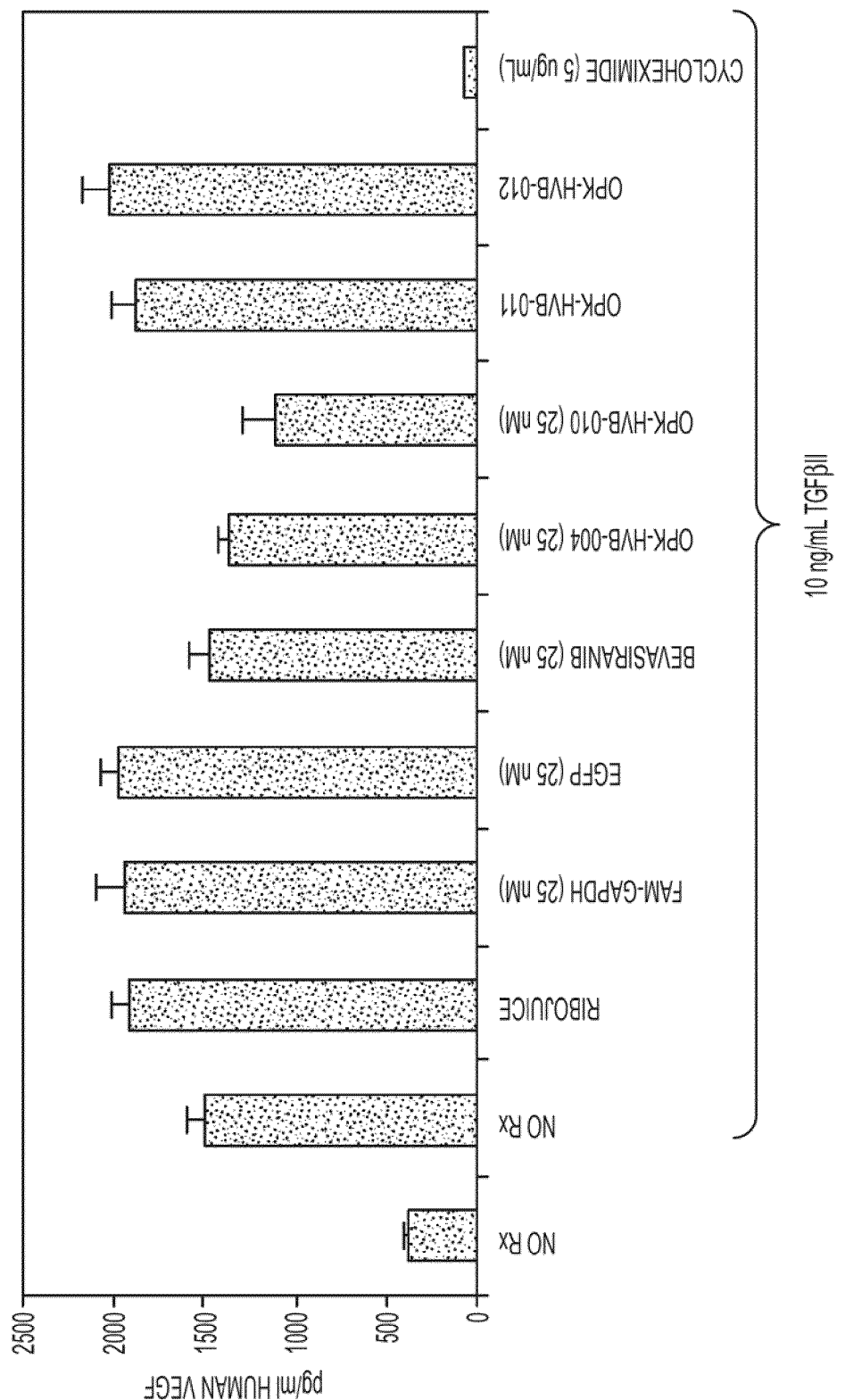
FIG. 14 depicts the amount of VEGF protein expressed for a secondary screen of siRNAs targeting the VEGF$_{165}$ exon 7/8 junction.
Figure 15:
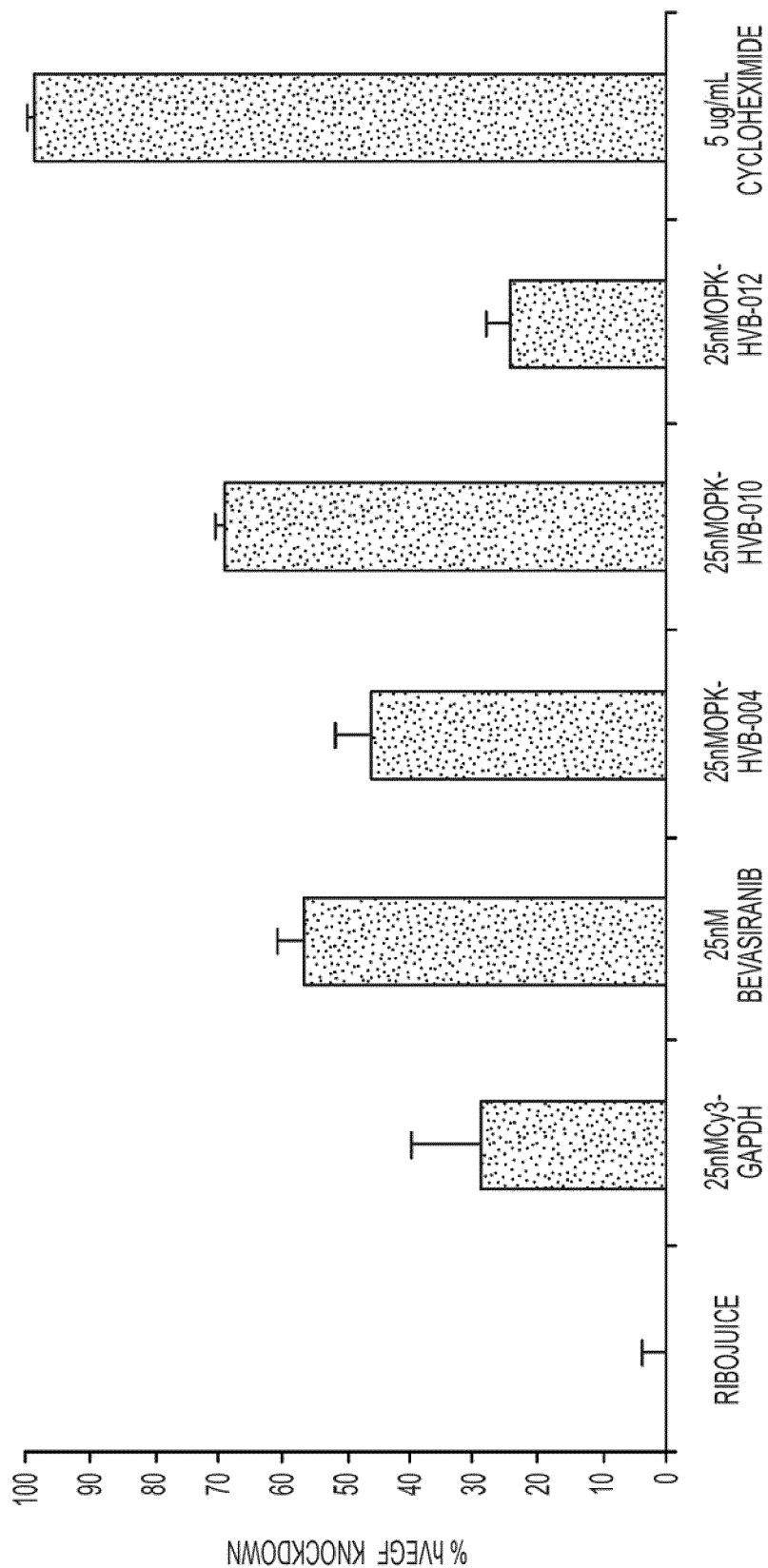
FIG. 15 depicts the percent knockdown of human VEGF protein for a secondary screen of siRNAs targeting the VEGF$_{165}$ exon 7/8 junction.

Results: Treatment of ARPE19 cells with TGFβII induced VEGF production in ARPE19 cells and ELISA results demonstrated several siRNA candidates inhibited the production of TGFβII-induced VEGF in ARPE19 cells. RT-PCR confirmed that 2 candidates inhibited production of $VEGF_{165}$, $VEGF_{121}$ and $VEGF_{189}$, but spared $VEGF_{165b}$. As shown in FIG. 12 (pg/mL hVEGF) and 13 (% knockdown hVEGF), VEGF siRNA candidates (Table 2) were screened for the ability to inhibit VEGF protein production by ARPE19 cells as tested by ELISA. Cells were treated with 10 ng/mL TGFβII to upregulate VEGF production. ELISA measured total VEGF protein and was not selective for any particular splice variant. Several candidates (OPK-HVB-004, OPK-HVB- 010, and OPK-HVB-011) demonstrate an inhibitory effect and warranted further study. As shown in FIG. 14 (pg/mL hVEGF) and 15 (% knockdown hVEGF), a secondary screen of VEGF production using the same methods as in FIGS. 12 and 13 demonstrated that OPK-HVB-004 and OPK-HVB-010 inhibited VEGF protein production and warranted further investigation.

Figure 16:
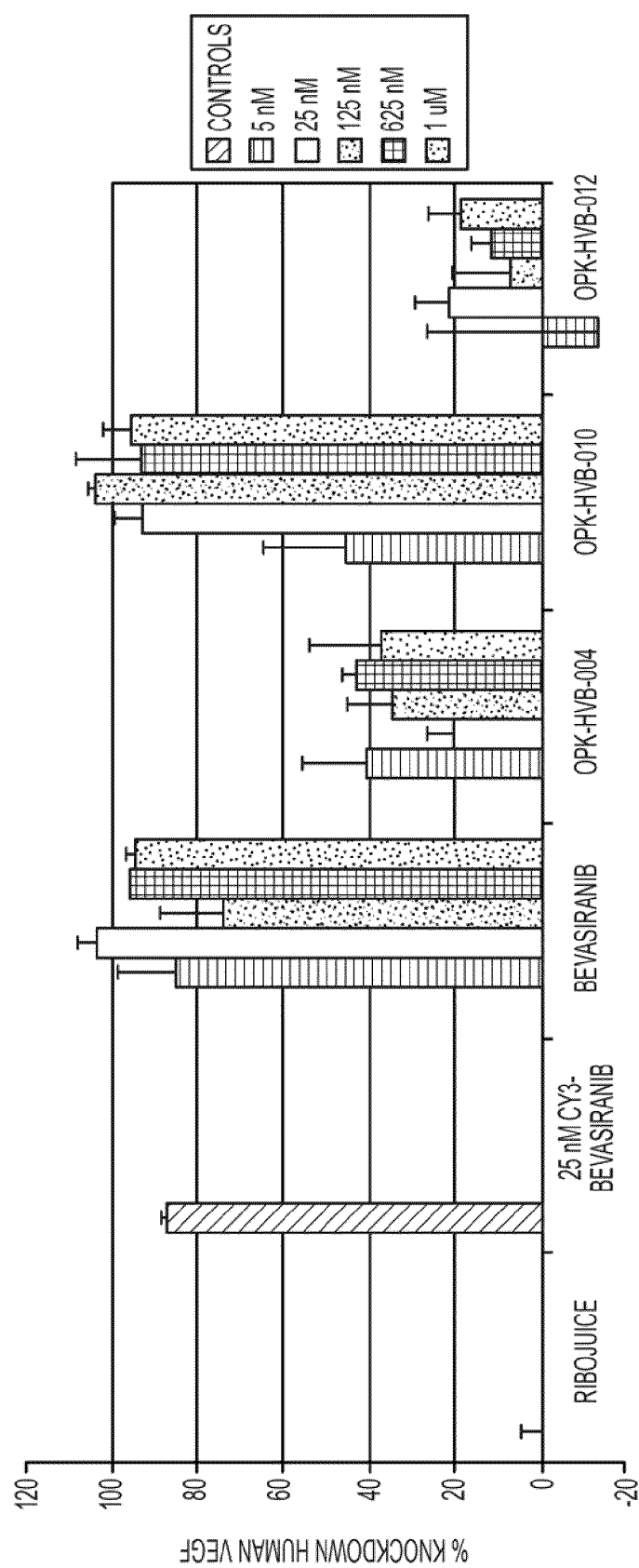
FIG. 16 depicts the percent knockdown of human VEGF protein for a secondary screen of siRNAs targeting the VEGF$_{165}$ exon 7/8 junction at varying concentrations.
Figure 24:
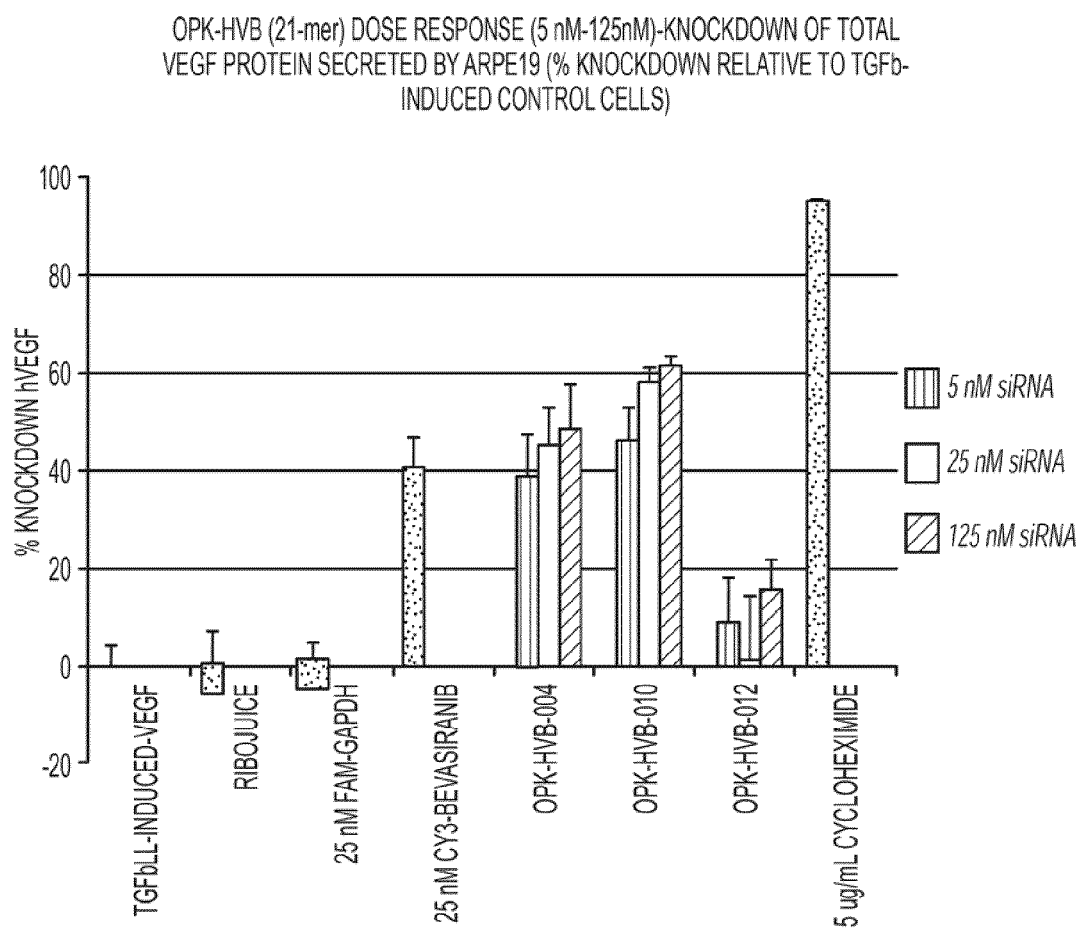
FIG. 24 depicts the effect of siRNAs on total VEGF protein secretion by ARPE19 cells.
Figure 27:
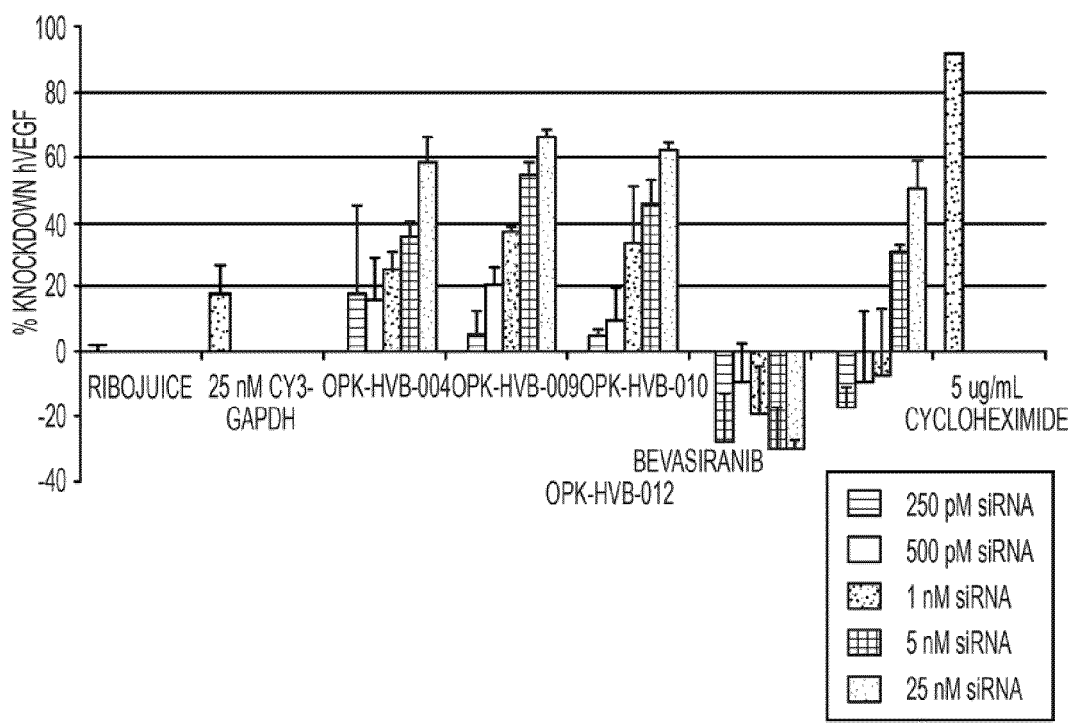
FIG. 27 depicts the effect of siRNAs on total VEGF protein secretion by ARPE19 cells.

FIGS. 16, 24 and 27 demonstrate a dose response efficacy of human VEGF knockdown with several candidates (OPK-HVB-004, OPK-HVB-010, and OPK-HVB-012) at varying concentrations.

Figure 17:
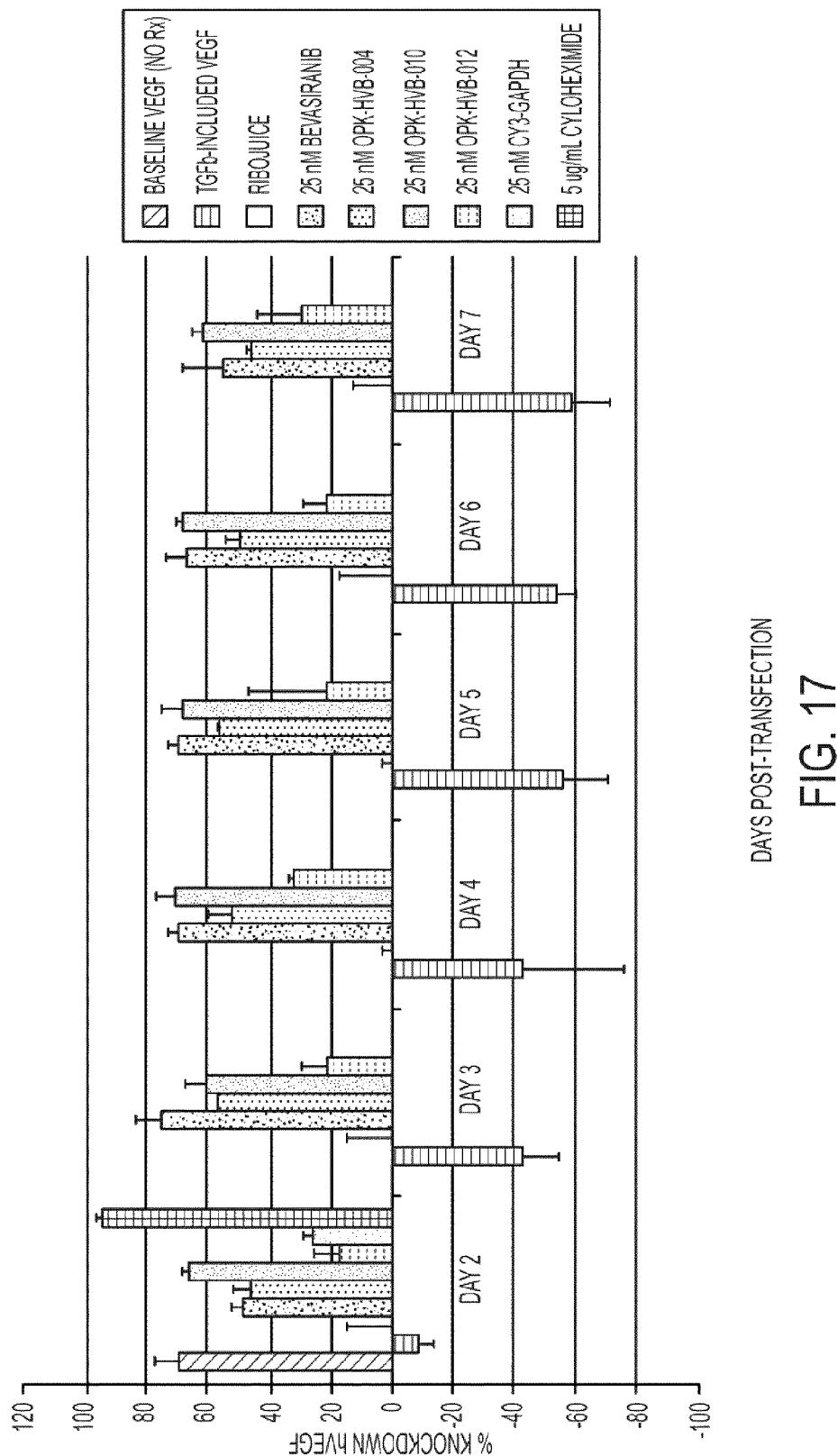
FIG. 17 depicts the percent knockdown of human VEGF protein over seven days for a secondary screen of siRNAs targeting the VEGF$_{165}$ exon 7/8 junction.

FIG. 17 demonstrates downregulation of human VEGF over one week (7 days) of several candidates (OPK-HVB-004, OPK-HVB-010, and OPK-HVB-012).

Figure 18:
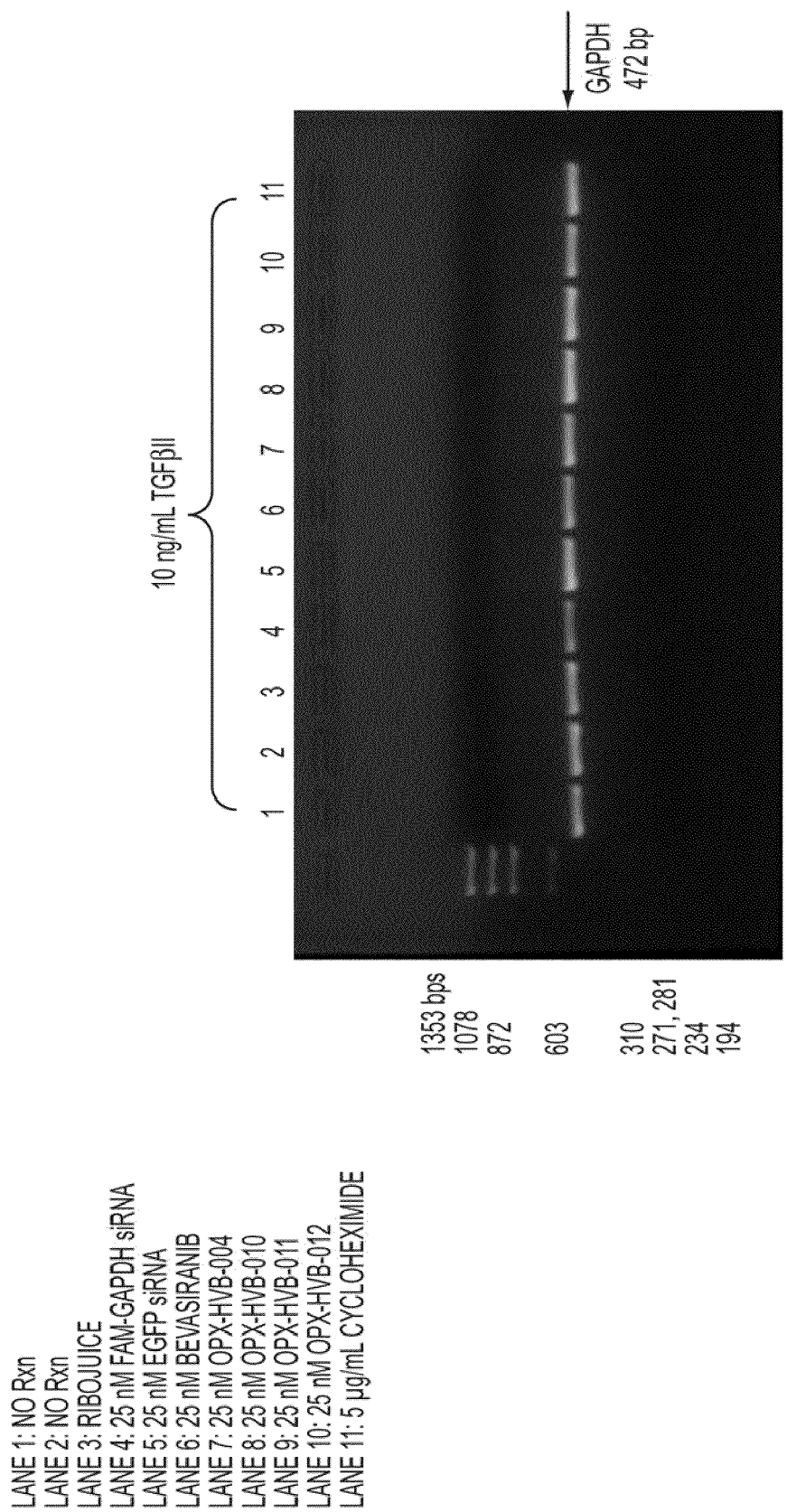
FIG. 18 depicts the effect of siRNA targeting the VEGF$_{165}$ exon 7/8 junction on GAPDH mRNA expression using RT-PCR.

As a control, GAPDH RT-PCR was performed on variously treated cells as shown in FIG. 18. Although the actual amount of RNA present was not quantified, the procedures are semi-quantitative when compared to the reference control lane 3. Specifically, downregulation of RNA production is demonstrated when a band appears fainter. In this experiment, samples in Lanes 2-11 were treated with 10 ng/mL TGFβII to upregulate the production of VEGF. The FAM-GAPDH siRNA downregulated GAPDH message (lane 4), while the other treatments have no effect on GAPDH mRNA, thus confirming that there is no variability in total RNA production in the treated cells.

Figure 19:
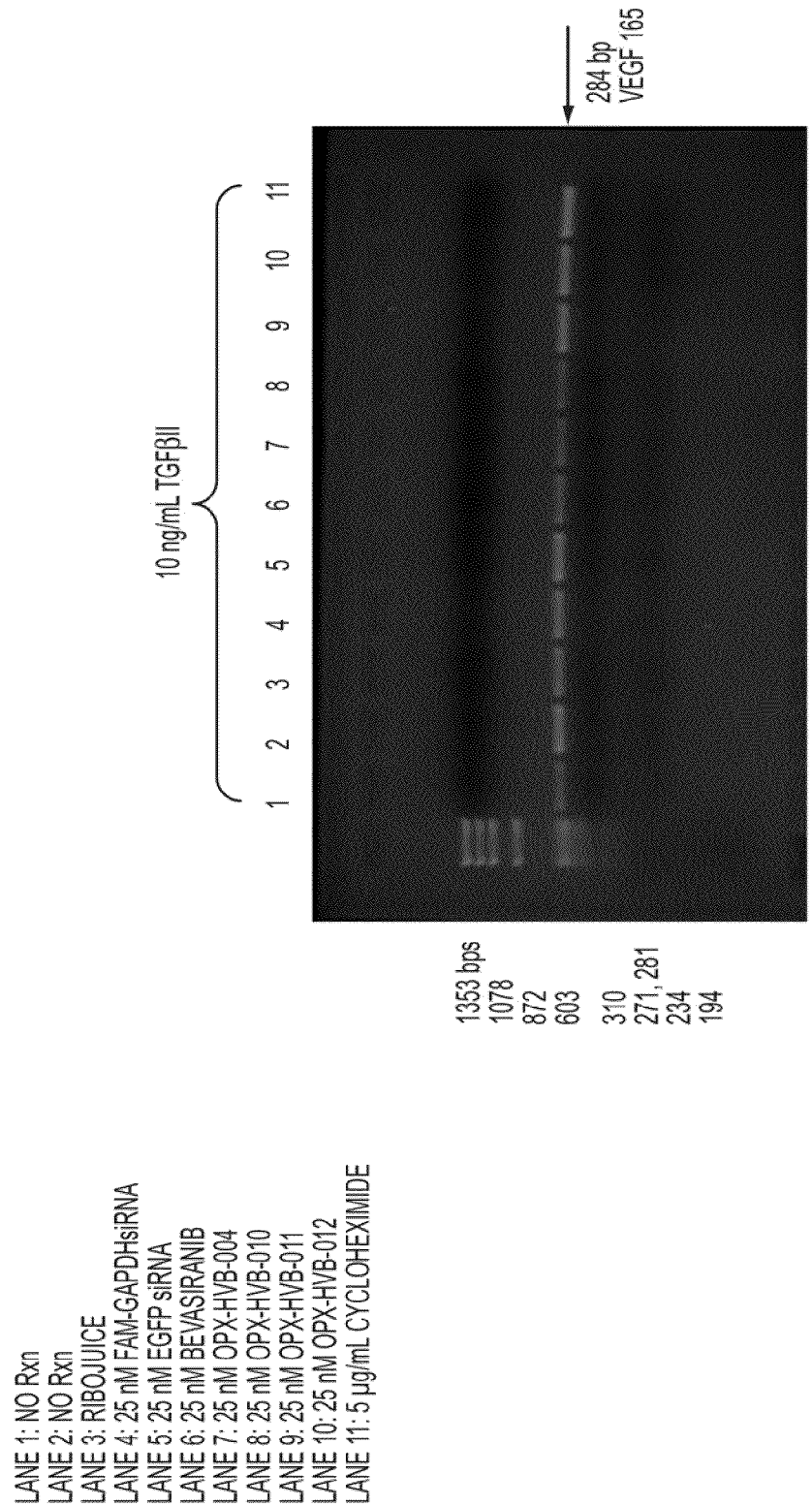
FIG. 19 depicts the effect of siRNA targeting the VEGF$_{165}$ exon 7/8 junction on VEGF$_{165}$ mRNA expression using RT-PCR.

$VEGF_{165}$ isoform RT-PCR was also performed on the treated cells as shown in FIG. 19. Samples in Lanes 2-11 were treated with 10 ng/mL TGFβII to upregulate the production of VEGF. 25 nM bevasiranib (lane 6), which is known to downregulate all VEGF isoforms, 25 nM OPK-HVB-004 (lane 7) and 25 nM OPK-HVB-010 (lane 8), down-regulated the production of $VEGF_{165}$ mRNA following induction with TGFβII (lane 2), as demonstrated by the bands being lighter than control in lane 3.

Figure 20:
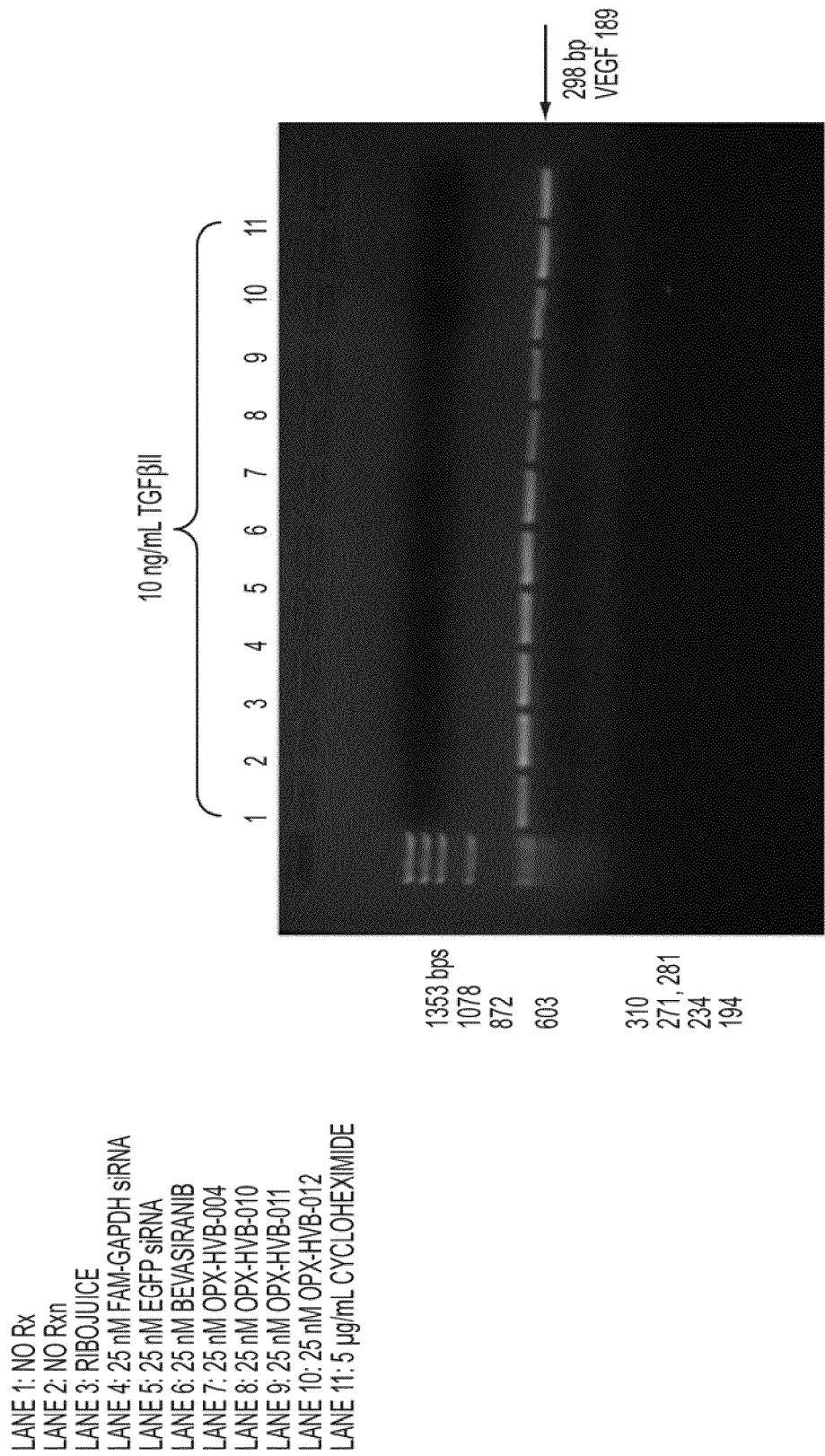
FIG. 20 depicts the effect of siRNA targeting the VEGF exon 7/8 junction on VEGF$_{189}$ mRNA expression using RT-PCR.

$VEGF_{189}$ isoform RT-PCR was also performed as shown in FIG. 20. Samples in Lanes 2-11 were treated with 10 ng/mL TGFβII to upregulate the production of VEGF.

25 nM bevasiranib (lane 6), 25 nM OPK-HVB-004 (lane 7) and 25 nM OPK-HVB-010 lane 8) downregulated the production of $VEGF_{189}$ mRNA following induction with TGFβII (lane 2) as demonstrated by the bands being lighter than control in lane 3.

Figure 21:
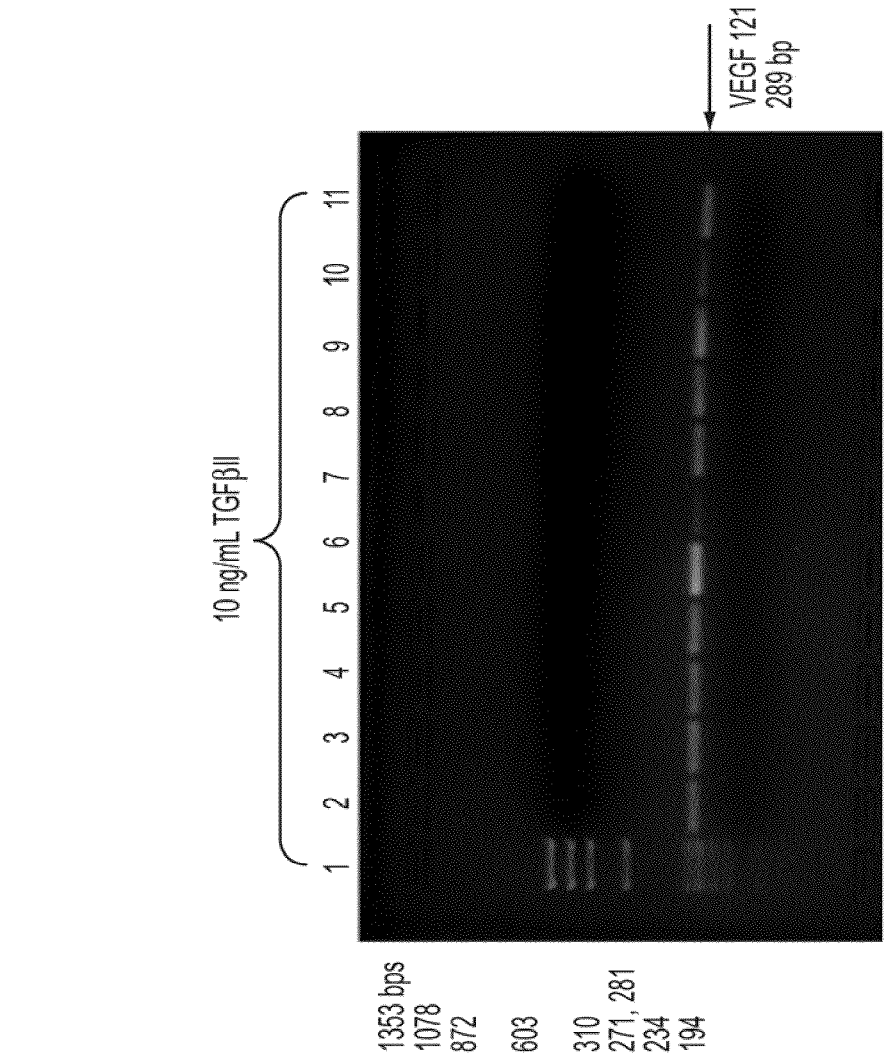
FIG. 21 depicts the effect of siRNA targeting the VEGF exon 7/8 junction on VEGF$_{121}$ mRNA expression using RT-PCR.

$VEGF_{121}$ isoform RT-PCR was then performed as shown in FIG. 21. Samples in Lanes 2-11 were treated with 10 ng/mL TGFβII to upregulate the production of VEGF.

$VEGF_{121}$ mRNA was downregulated in lane 6 (25 nM bevasiranib) as demonstrated by the bands being lighter than control in lane 3.

Figure 22:
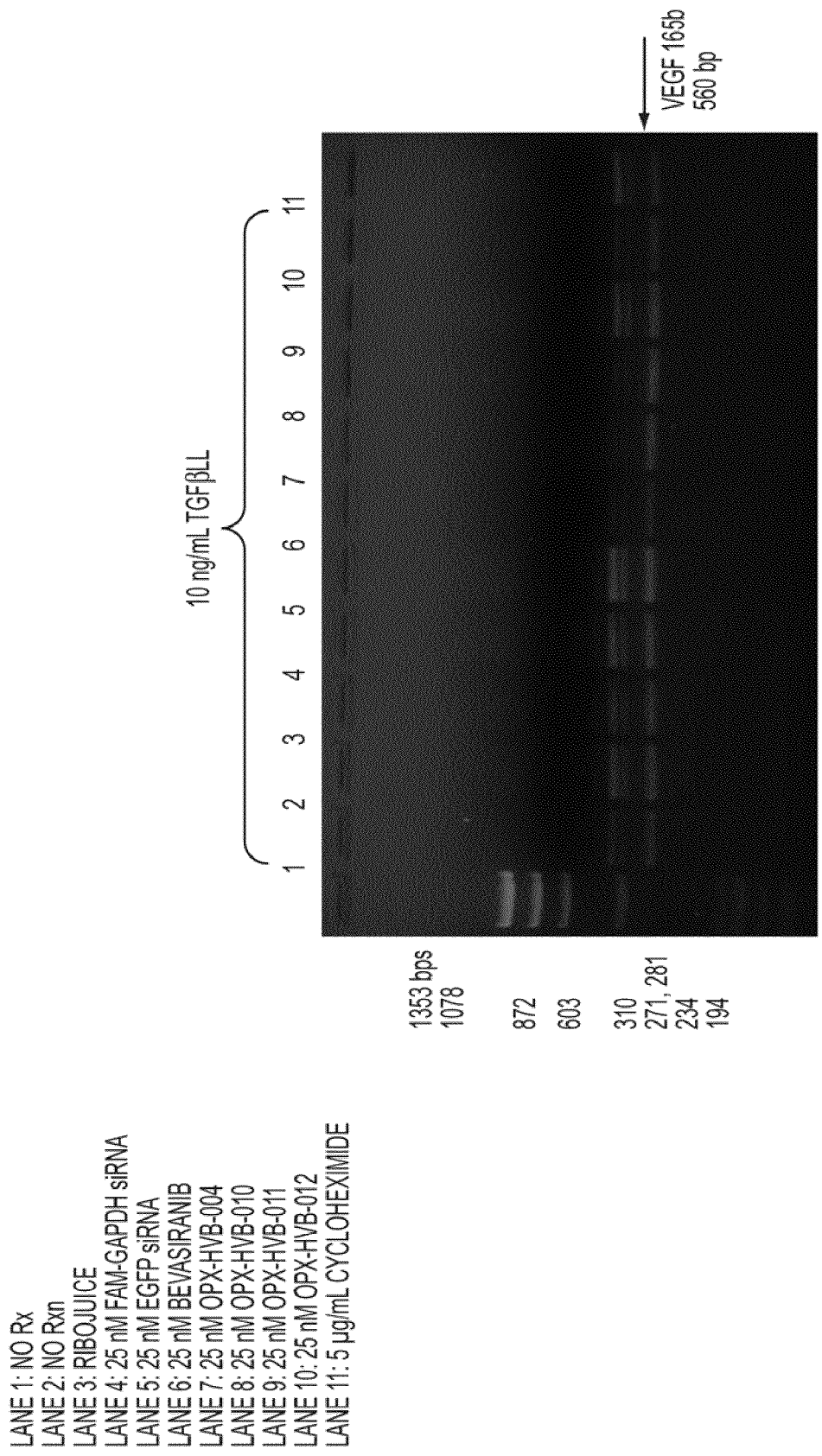
FIG. 22 depicts the effect of siRNA targeting the VEGF$_{165}$ exon 7/8 junction on VEGF$_{165b}$ mRNA expression using RT-PCR. Double banding at about 600 bp is artefactual.

Finally, $VEGF_{165b}$ isoform RTPCR was performed as shown in FIG. 22.

Samples in Lanes 2-11 were treated with 10 ng/mL TGFβII to upregulate the production of VEGF. As an initial matter, the double banding >600 bp was determined to be artifactual. However, $VEGF_{165b}$ mRNA is downregulated by bevasiranib (lane 6) as shown by the bands being fainter that the control of lane 3. In contrast, bands for OPK-HVB-004 (lane 7) and OPK-HVB-010 (lane 8) were not fainter that control in lane 3. Thus, these siRNA constructs preserved $VEGF_{165b}$ expression while also being able to inhibit various other VEGF isoforms. Thus, siRNAs sparing $VEGFA_{165b}$ can be synthesized and may be more efficacious then siRNAs that knockdown all VEGF-A isoforms. $VEGF_{165b}$ sparing siRNAs may be potent therapeutic candidates for the treatment of ocular neovascularization.

Example 13

Cytokine Profile Following Treatment with siRNAs

The cytokine secretion profile of ARPE19 cells following treatment with polyinosinic-polycytidylic acid sodium salt [Poly (I:C)], a dsRNA analogue was determined Further tests to determined whether or not siRNAs behaved like Poly (I:C) and caused the cells to produce the same cytokines were conducted.

Methods. ARPE19 cells were seeded in 24 well plates (50,000 cells per well). Twenty-four hours later, media was removed and cells were treated with Poly (I:C); 0-1000 mg/mL (Sigma, St. Louis, Mo.) or poly deoxyinosinic-deoxycytidylic acid sodium salt [Poly (dI:dC); 50 mU/mL-800 mU/mL] (Sigma), prepared in serum free DMEM/F12(1:1) (Invitrogen, Carlsbad, Calif.). Forty-eight hours post-treatment, media was collected from cells and analyzed for IFN-α, IFN-β, IL-8, IL-6, TNFα, ICAM, IL-12 and MCP-1 via ELISA (QUANTIKINE® Immunoassays for IFN-γ, IL-8, IL-6, TNFa, ICAM, IL-12 and MCP-1, R&D Systems, Minneapolis, Minn.); VeriKine™ ELISA kits for IFN-α and IFN-β, PBL Biomedical Laboratories, Piscataway, N.J.) according to the manufacturers' protocols.

ARPE19 cells were transfected with bevasiranib, OPK-HVB-004, OPK-HVB-009, OPK-HVB-010 and OPK-HVB-012 (Dharmacon/Thermo Scientific, Chicago, Ill.). Cells were seeded in 24 well plates (40,000 cells per well). 24 hours later, cells were transfected with 25 nM siRNA using RiboJuice™ Transfection Reagent (Novagen/EMD, San Diego, Calif.) according to the manufacturer's protocol. 24 hours post-ransfection, cells were treated with 10 ng/mL human recombinant TGFβII (R&D Systems). 48 hours post-transfection (ie. 24 hours post-TGFbII treatment), media was collected and cytokine levels were analyzed, as described above. Additionally, media was analyzed for hVEGF via ELISA (R&D Systems). Results are shown in FIG. 23.

Conclusions. Based upon the foregoing it is suggested that (ii) ARPE19 cells produce several inflammatory cytokines in response to Poly (I:C), a dsRNA analogue, but do not produce three key mediators, IFN-α, IFN-β or IFN-γ; (ii) ARPE19 cells can be used to study the inflammatory potential and specific effects of dsRNAs such as siRNAs; and (iii) OPK-HVB-009 an OPK-HVB-010 did not cause ARPE19 cells to secrete any of the cytokines tested, suggesting they may have a low inflammatory potential.

Example 14

Dose Response Curves Shows Specificity of siRNAs

Figure 25:
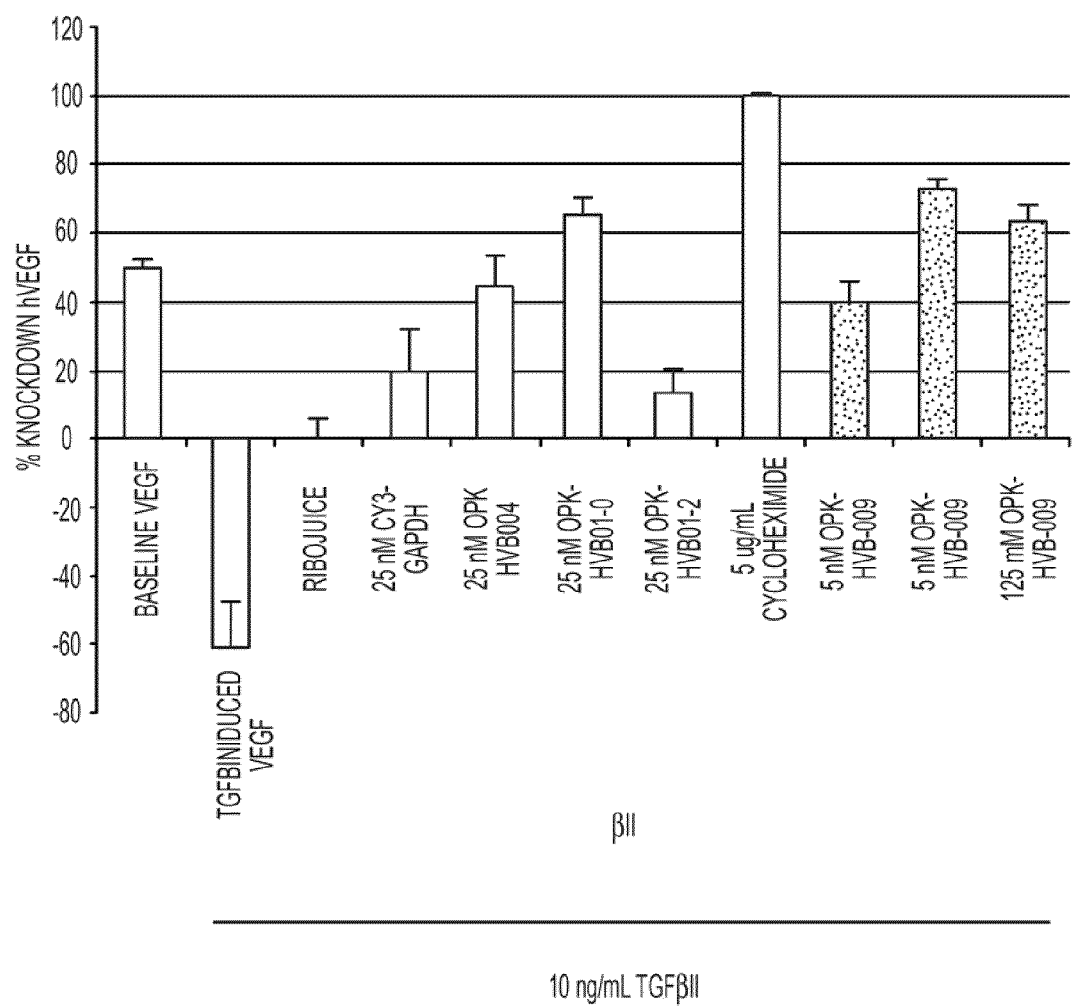
FIG. 25 depicts the effect of siRNAs on total VEGF protein secretion by ARPE19 cells.
Figure 26:
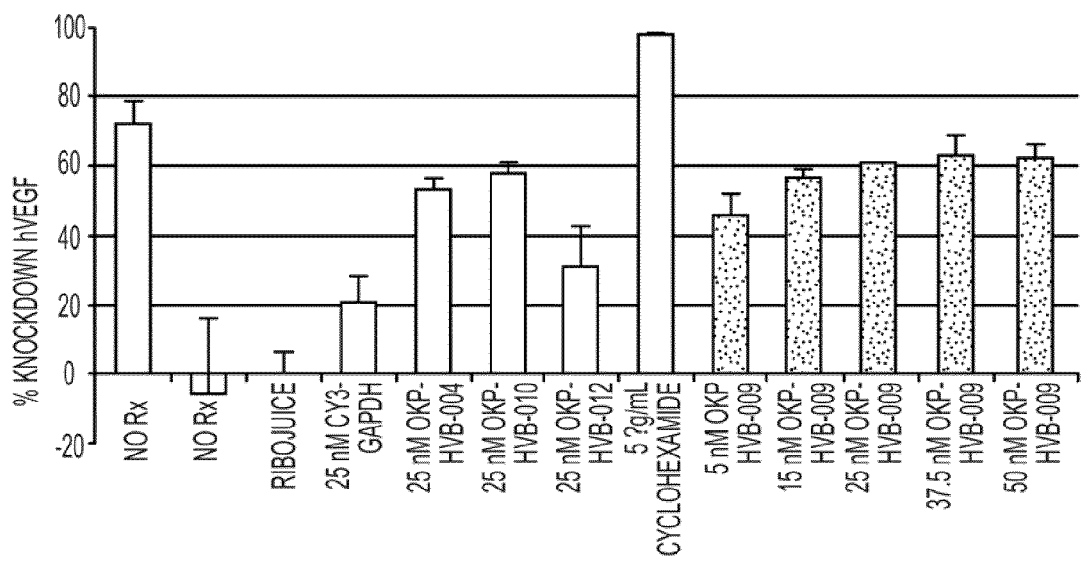
FIG. 26 depicts the effect of siRNAs on total VEGF protein secretion by ARPE19 cells.

A dose response curve was generated using various siRNAs, 21-mers, as shown in FIGS. 26 and 27. A dose response was seen with certain siRNAS indicating a specific response to the siRNAs used. A dose response curve was also generated for OPK-HVB-009 as shown in FIGS. 25 and 26. The cells were treated and transfected as described in Examples 12 and 13. Cells were seeded in 24 well plates (40,000 cells/well). Additionally, different concentrations were used, and therefore, the volumes of OPTI-MEM, RiboJuice™, and siRNA were adjusted accordingly when preparing the 50 μl transfection mix.

Example 15

Stability of siRNAs

Figure 28:
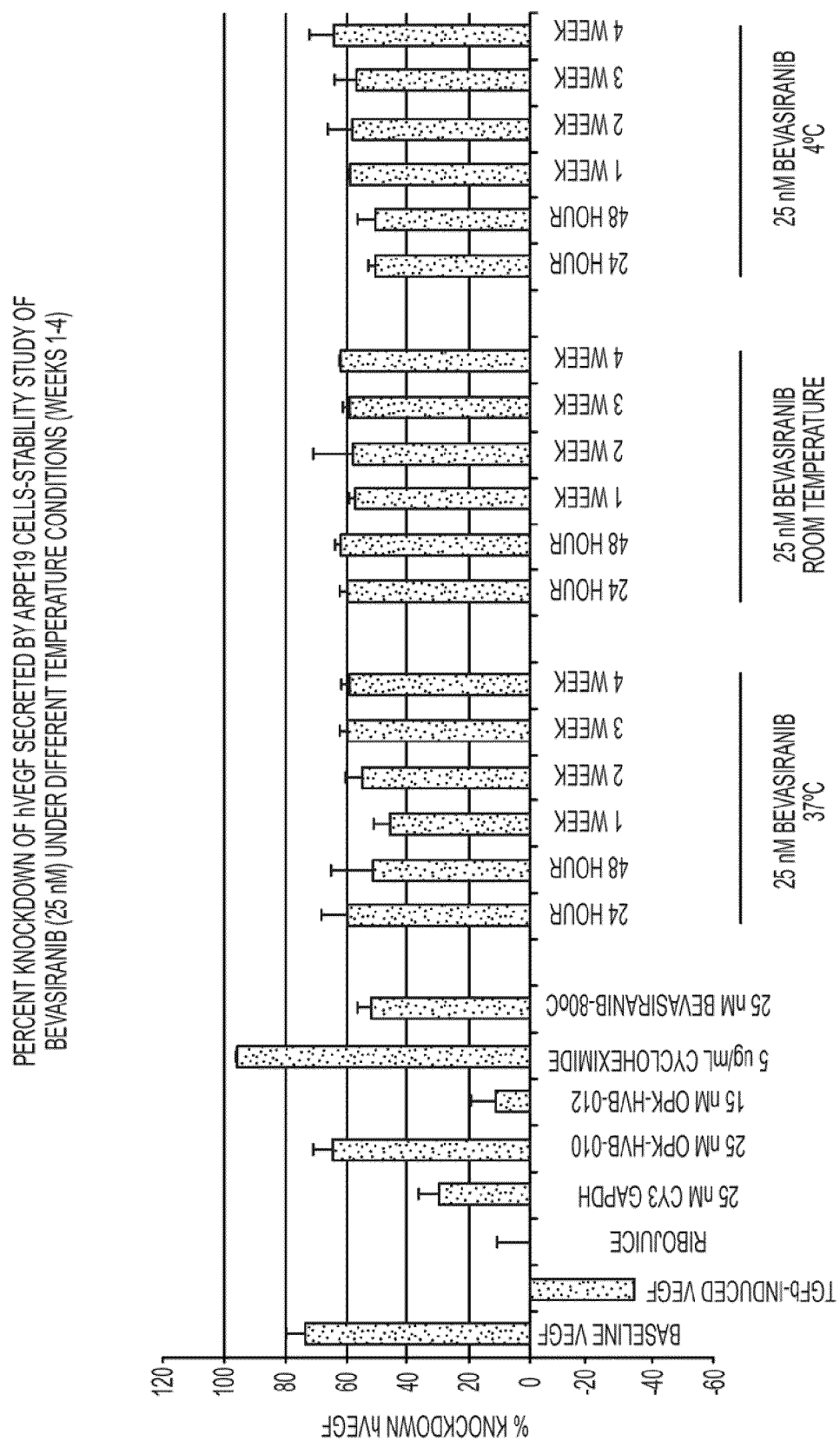
FIG. 28 depicts the stability of bevasiranib under different temperature conditions over time.
Figure 29:
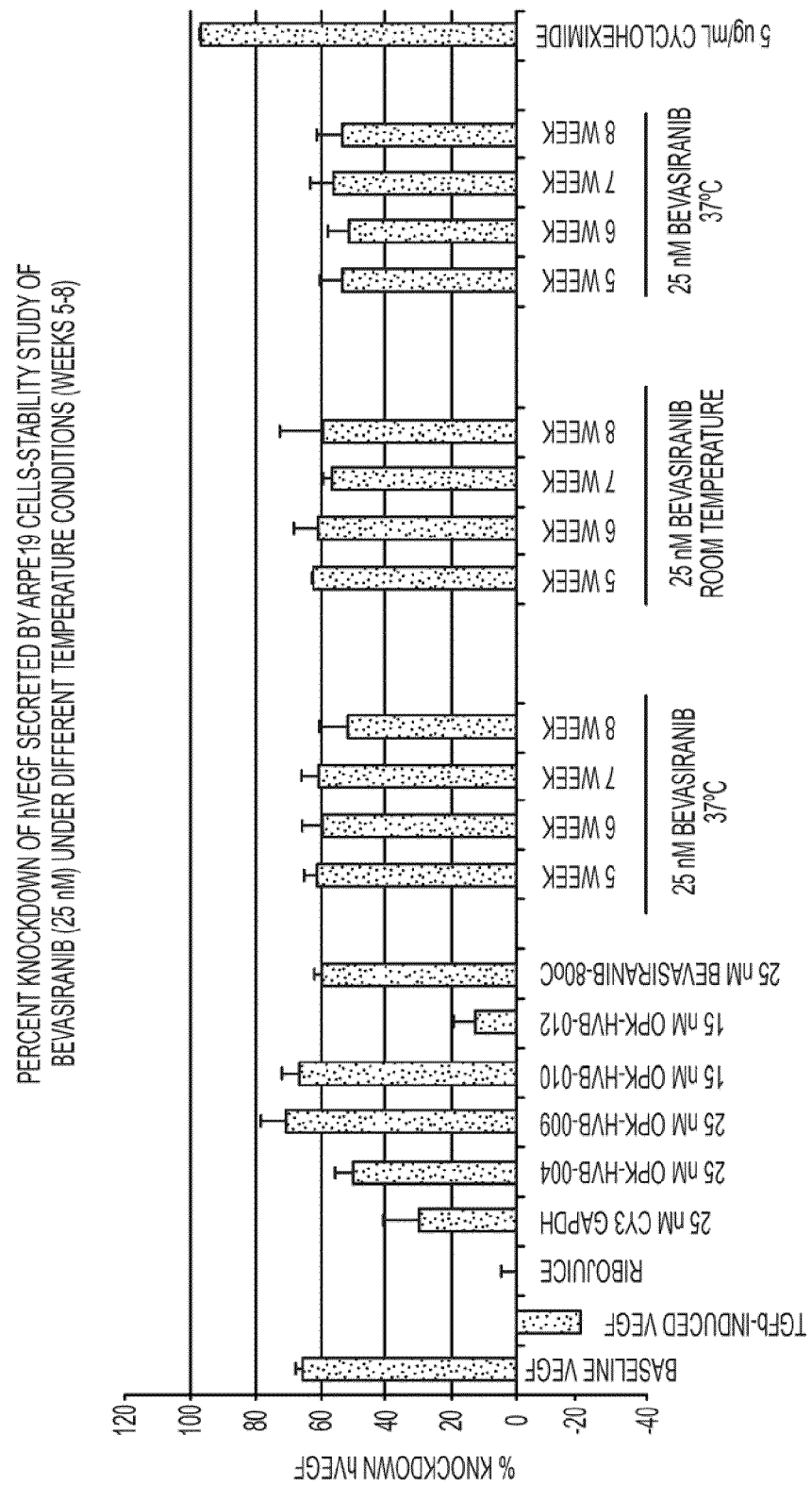
FIG. 29 depicts the stability of bevasiranib under different temperature conditions over time.
Figure 30:
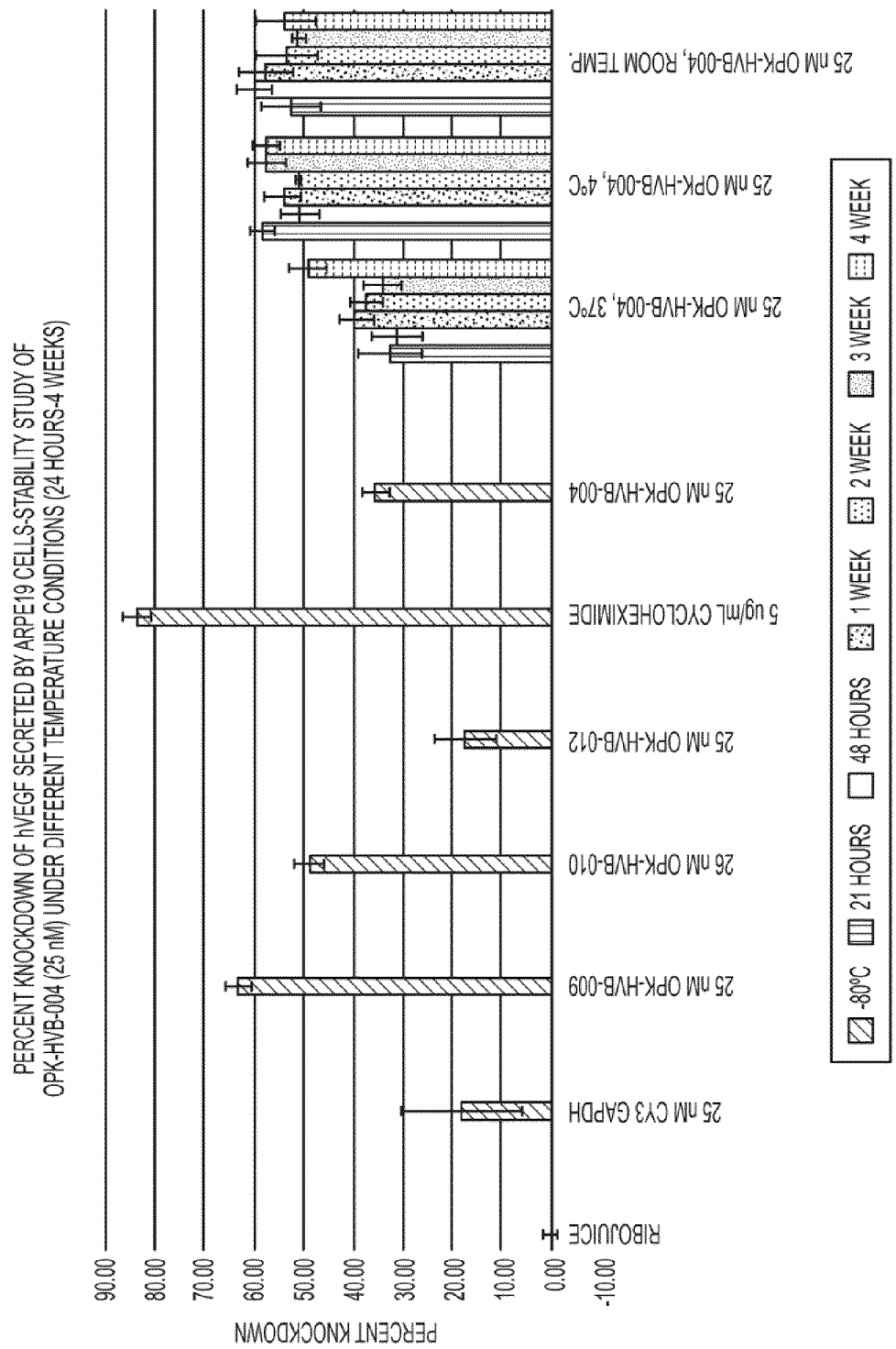
FIG. 30 depicts the stability of OPK-HVB-004 under different temperature conditions over time.

ARPE19 cells were transfected with siRNAs that had been stored under various conditions as shown in FIGS. 28, 29, 30

31, and 32. The cells were transfected as described in Examples 12 and 13. It was found that the siRNA molecules were stable under various conditions as shown in FIGS. 28, 29, 30, 31, and 32. For example, 7.5 µM siRNA was aliquoted into 3 tubes and each tube was stored at a different temperature (37° C., room temperature, 4° C.) for up to 8 weeks. Aliquots of each tube were collected at predetermined time points (24 hrs, 48 hrs and then weekly). Upon collection aliquots were stored at −80° C. Each aliquot was subsequently tested for efficacy in ARPE19 cells to see if the siRNAs maintained their stability under the different environmental conditions. siRNAs were transfected into ARPE19 cells using the methods described in Example 12 where 40,000 cells were seeded per well.

Example 16

Cross-Species Down Regulation of VEGF

C6 cells were seeded in 24 well plates (P12, 40,000 cells per well). Eighteen to twenty-four hours post-seeding, cells were 50-70% confluent and used for transfection. Cells were transfected with OPK-HVB-004, OPK-HVB-009, OPK-HVB-010 and OPK-HVB-012 using the RiboJuice™ siRNA Transfection Reagent (Novagen) following the manufacturer's protocol. Briefly, for a single well serum-free OPTI-MEM (40.5 µL-47 µL) was pipetted into an eppendorf tube and then 2 µL of RiboJuice™ were added to the OPTI-MEM (Gibco). The solution was mixed by gentle vortexing and centrifuged briefly to collect the contents at the bottom of the tube and incubated at room temperature for 5 min siRNA (0.3 µL-7.5 µL of a 100 nM or 1 µM stock) was added to the RiboJuice™/medium mix and gently mixed and briefly centrifuged to collect contents at the bottom of the tube. The mixture was incubated at room temperature for 15 minutes. During the incubation, media was removed from cells and replaced with 250 µL of fresh C6 growth media (F-12 Kaighn's, 2.5% fetal calf serum; 15% horse serum, 1% penicillin/streptomycin). After the 15 min incubation, the siRNA/RiboJuice™/medium mixture (50 µL) was added dropwise to the cells. The plate was gently rocked to ensure the complexes were evenly dispersed throughout the well. The final concentration of siRNA in the 300 µL volume was 250 µM, 500 µM, 1 nM, 5 nM or 25 nM. Cells were maintained at 37° C., 5% CO2 for 24 hours. All volumes were scaled up such that each siRNA was tested at each concentration in triplicate. 24 hours post-transfection, the transfection mixture was removed and cells were treated with 500 µLs of fresh C6 growth media or with fresh C6 growth media supplemented with 10 ng/mL human recombinant TGFβII. The cells were returned to 37° C., 5% $CO_2$ for an additional 24 hours. Afterwards the media was removed from the cells and analyzed for protein expression by ELISA (Quantikine rat VEGF ELISA kit, R&D Systems).

NIH3T3 cells were seeded in 24 well plates (P2-P6, 40,000 cells per well). Eighteen to twenty-four hours post-seeding, cells were 50-70% confluent and used for transfection. Cells were transfected with siRNAs using Lipofectamine™ Reagent 2000 (Invitrogen) following the manufacturer's protocol. Briefly for a single well, siRNA (1 µM or 7.5 µM) was diluted in 50 µL OPTI-MEM in an eppendorf tube and gently mixed and vortexed. In a second eppendorf tube 1 µL of Lipofectamine 2000 was combined with 49 µL of OPTI-MEM. The mixture was gently mixed and vortexed and incubated for 5 minutes at room temperature. After the 5 minutes, the diluted siRNA (50 µL volume) was added to the diluted Lipofectamine 2000 (50 µL). The contents were mixed gently and incubated at room temperature for 20 minutes. During the 20 minute incubation, media was removed from the cells and replaced with 500 µLs of fresh NIH3T3 growth media (DMEM, 10% fetal calf serum). After the 20 minutes the siRNA-Lipofectamine 2000 complex (100 µL) was added dropwise to the cells. The plate was gently rocked to ensure the complexes were evenly dispersed throughout the well. The cells were then incubated at 37° C., 5% $CO_2$ for 24 hours. The final concentration of siRNA in the 500 µL volume was 1 nM, 5 nM or 25 nM. 24 hours post-transfection, the transfection mixture was removed and cells were treated with 500 µLs of fresh DMEM or with fresh DMEM supplemented with 10 ng/mL human recombinant TGFβII. The cells were returned to 37° C., 5% $CO_2$ for an additional 24 hours. Afterwards the media was removed from the cells and analyzed for protein expression by ELISA (Quantikine mouse VEGF ELISA kit, R&D Systems).

Figure 34:
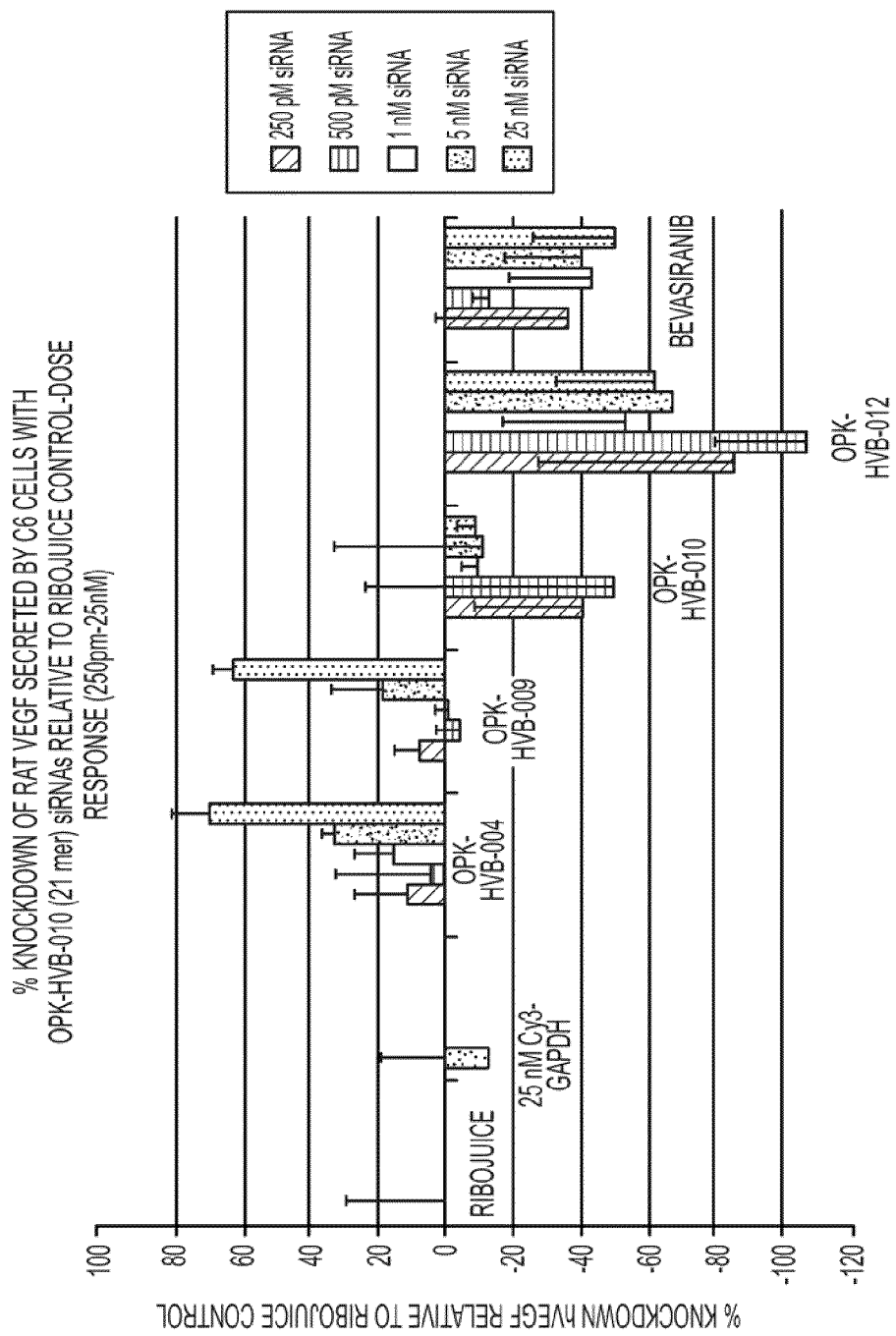
FIG. 34 depicts the effect of siRNAs on rat VEGF secretion by C6 cells.
Figure 35:
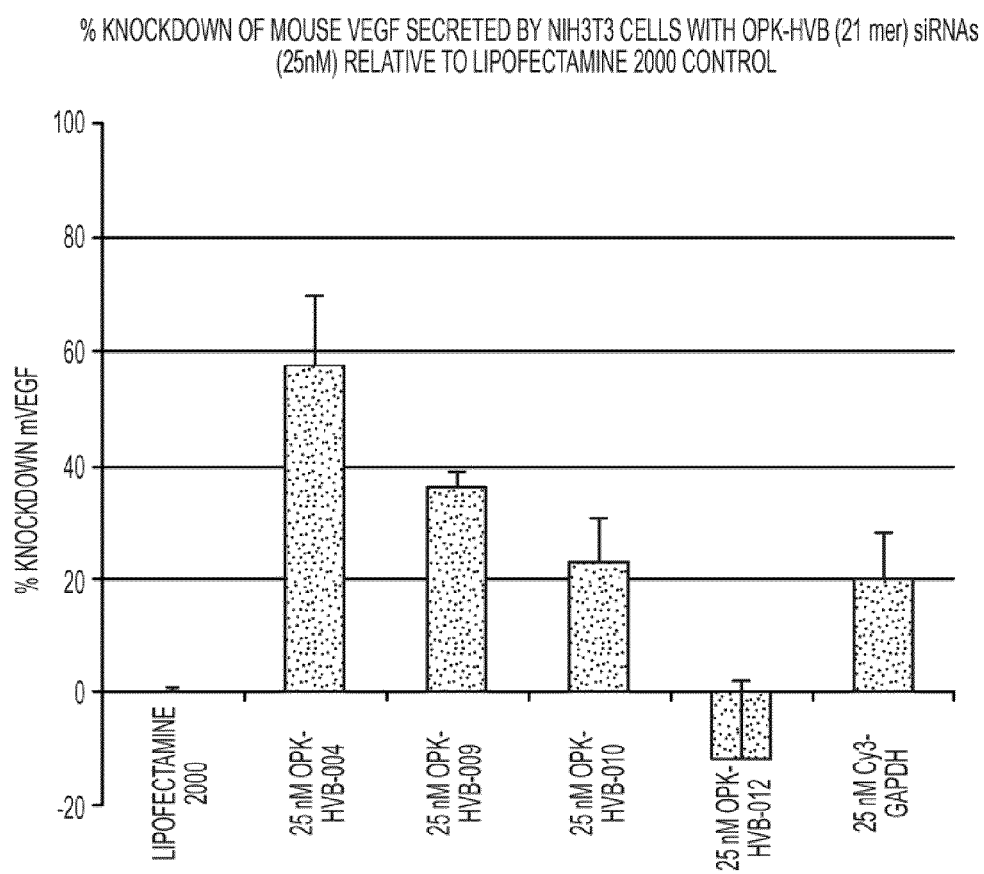
FIG. 35 depicts the effect of siRNAs on mouse VEGF secretion by NIH3T3 cells.
Figure 39:
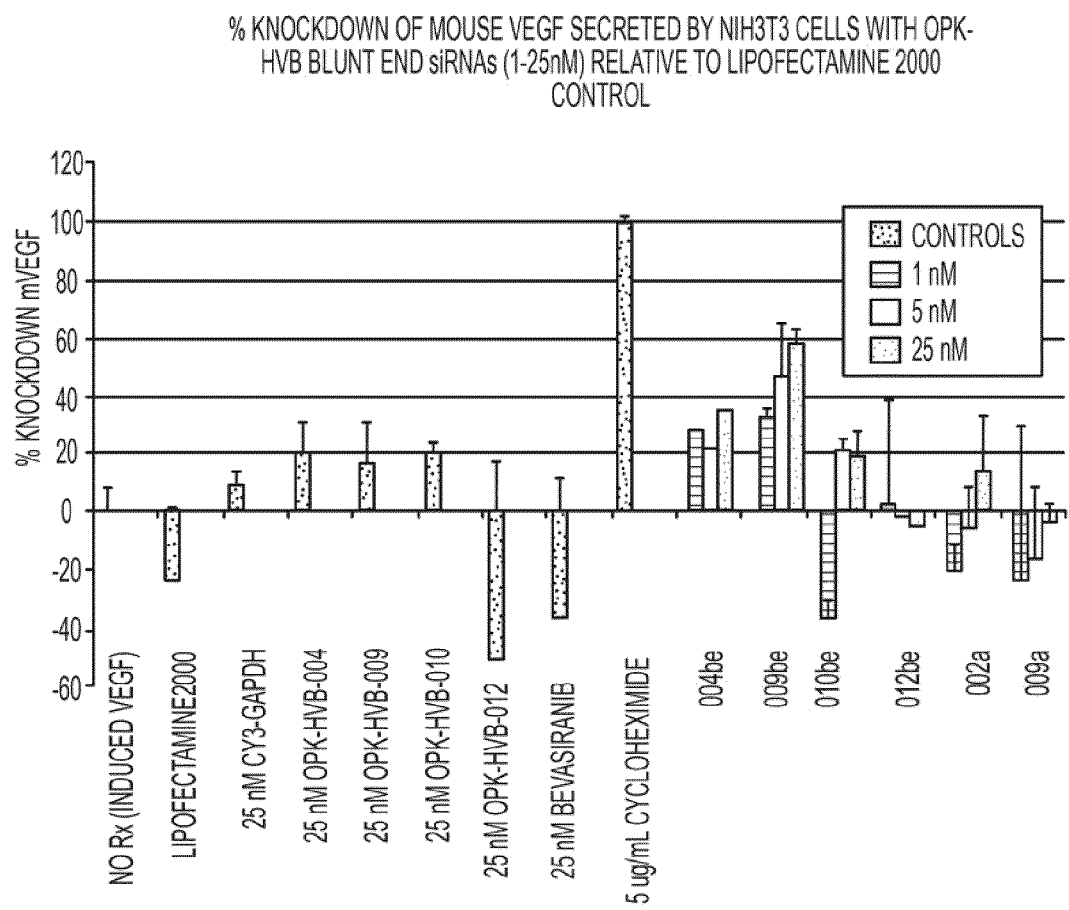
FIG. 39 depicts the effect of siRNAs on mouse VEGF secretion by NIH3T3 cells

Results of the experiments are shown in FIGS. 34, 35 and 39. OPK-HVB-004 and OPK-HVB-009 were able to inhibit VEGF secretion by C6 cells as shown in FIG. 34. Similar experiments were done in mouse cells (NIH3T3) and OPK-HVB-004, OPK-HVB-009, and OPK-HVB-010 were able to inhibit secretion of mouse VEGF as shown in FIGS. 35 and 39.

Example 17

Figure 36:
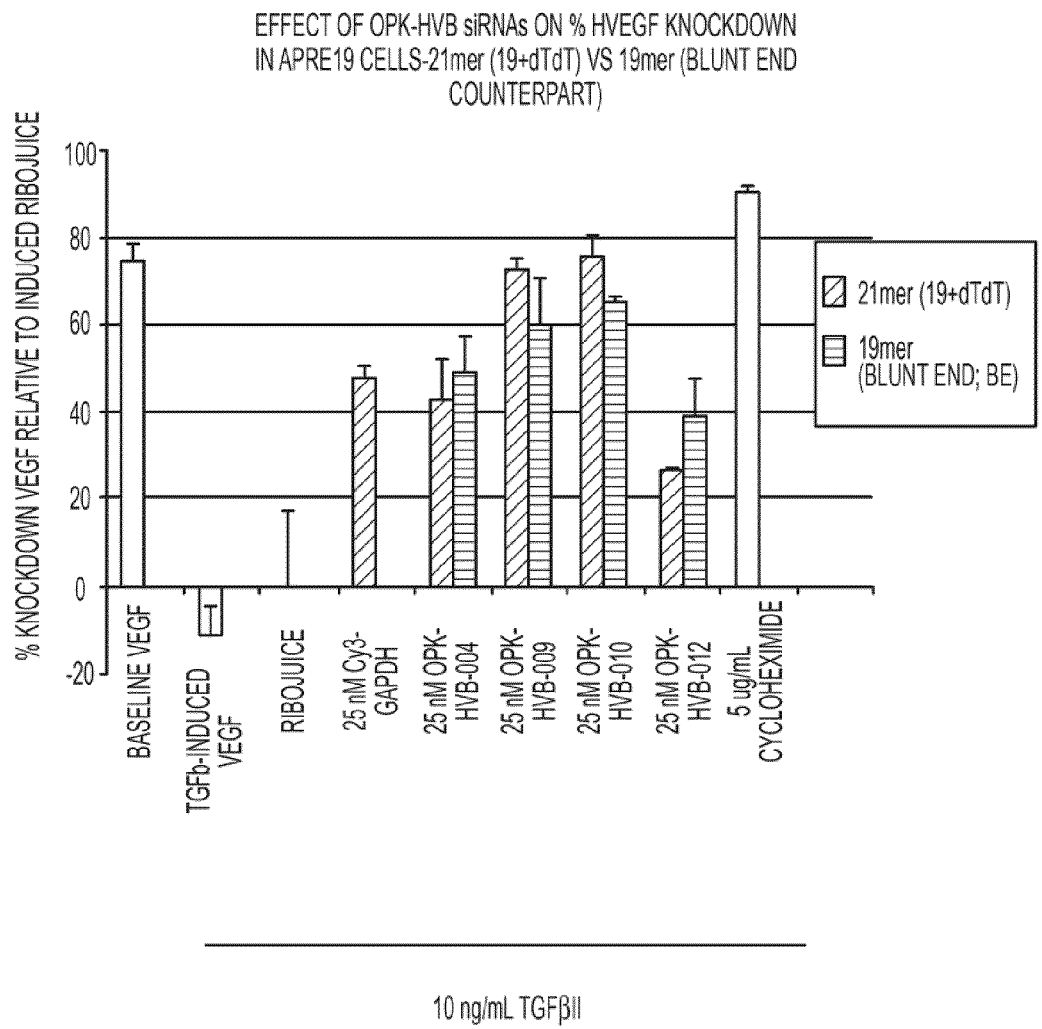
FIG. 36 depicts the effect of siRNAs on VEGF secretion by ARPE19 cells.

Comparison of Different siRNAs 21 mer siRNAs comprising an overhang were compared to a 19 mer blunt-end counterpart. ARPE19 cells were transfected with the different siRNAs as described in Examples 12, 13, and 14 and VEGF production was measured. The Blunt end counterpart was found to knockdown VEGF production in ARPE19 cells equally effective as the 21 mer as shown in FIG. 36. For example, a blunt end version of bevasiranib comprising SEQ ID NO: 119 and SEQ ID NO: 120 was equally effective at knocking down VEGF production as shown in FIG. 36.

Example 18

Figure 37:
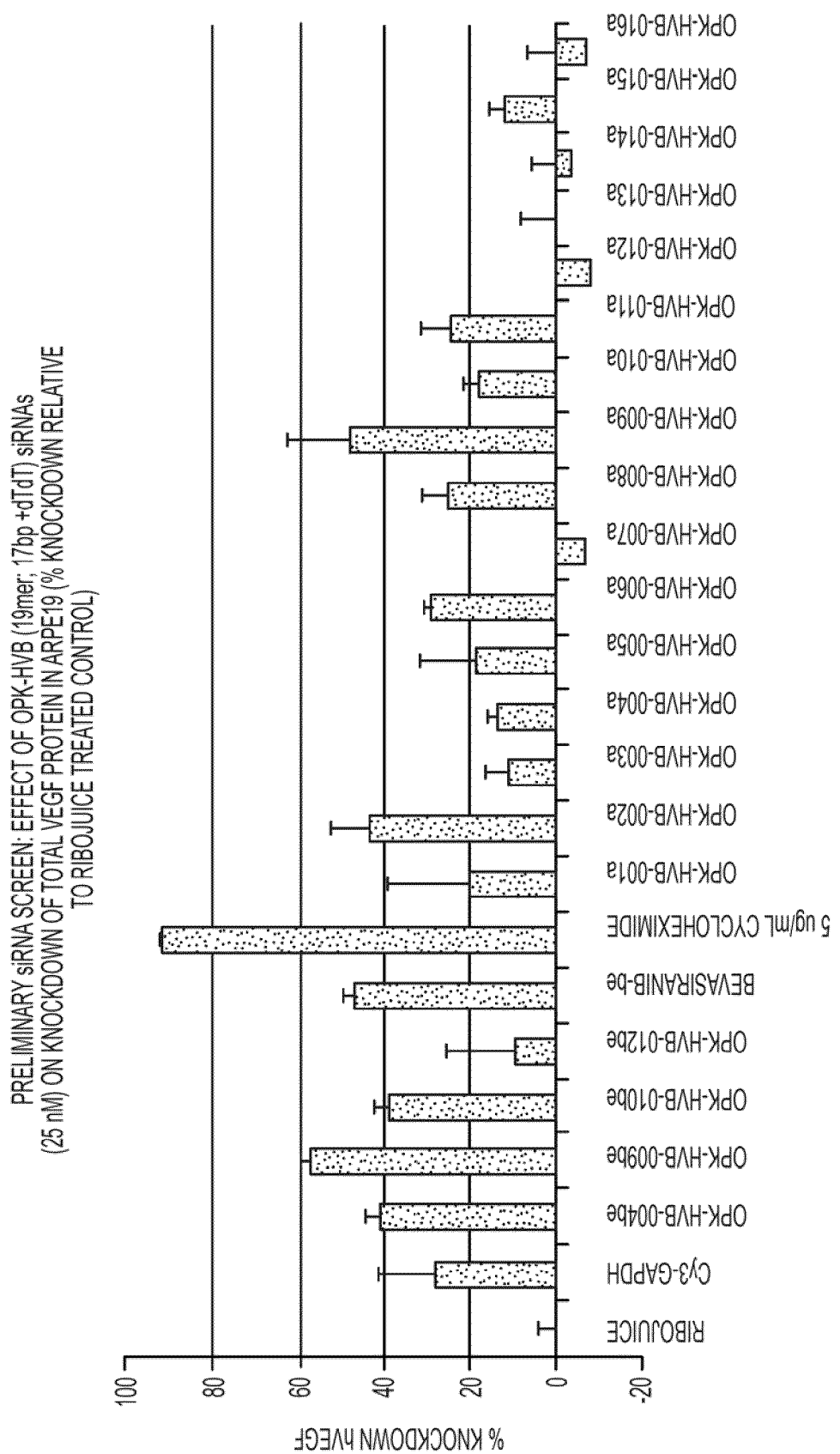
FIG. 37 depicts the effect of siRNAs on VEGF secretion by ARPE19 cells.

Screen of 19 mers Comprising 17 bp and an Overhang can Inhibit VEGF Production siRNAS comprising a 17 mer and a dTdT overhang were transfected in ARPE19 cells as described in Examples 12, 13, and 14. Several siRNAs were found to inhibit VEGF production as shown in FIG. 37.

Example 19

Figure 38:
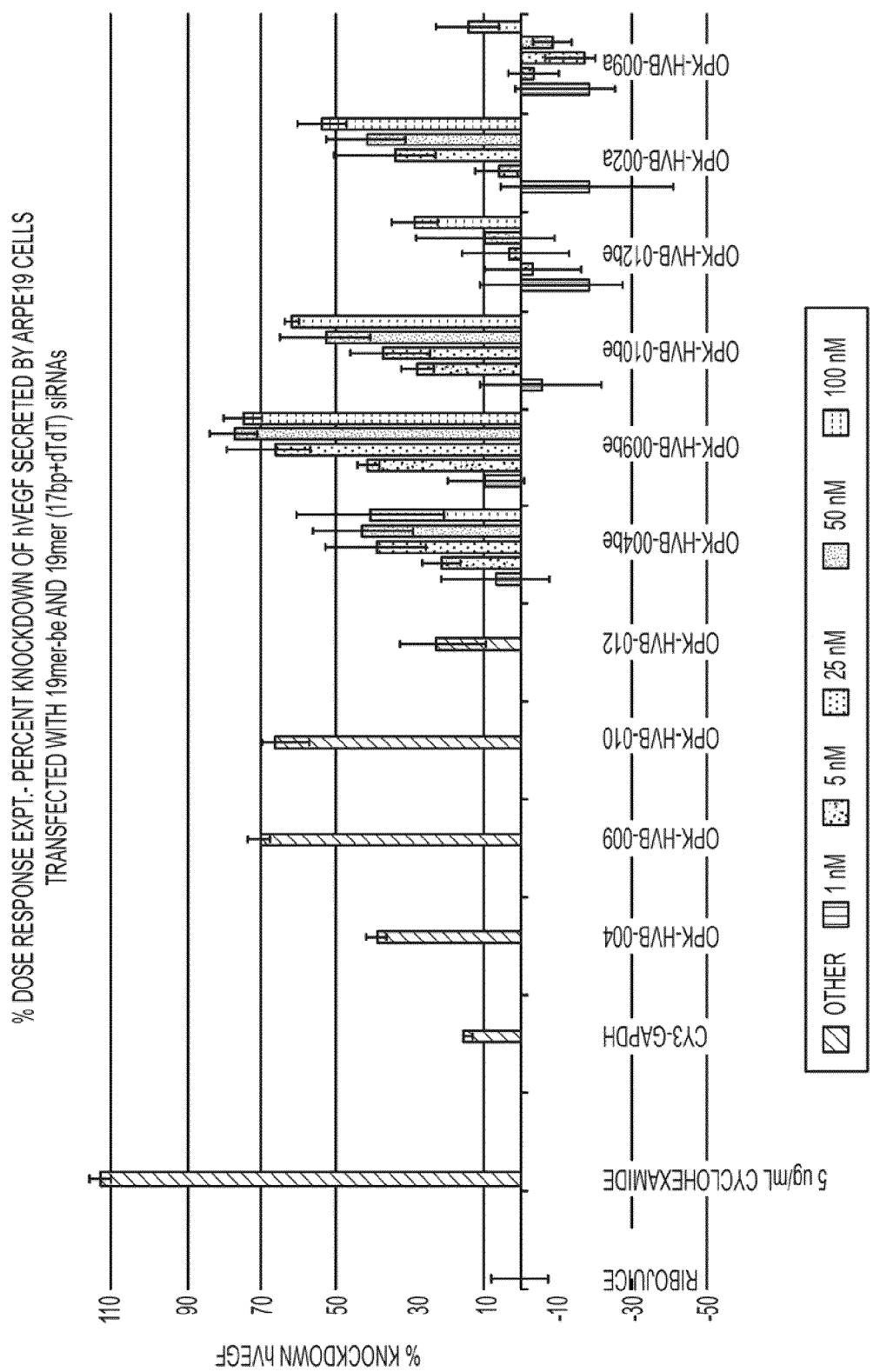
FIG. 38 depicts the effect of siRNAs on VEGF secretion by ARPE19 cells.

Dose Response of siRNAs 19 mers comprising a blunt end or an overhang 19 mer (17 bp+dTdT over) were transfected into ARPE19 cells at various doses as shown in FIG. 38. A dose response curve was generated by measuring VEGF secretion as described in Examples 12, 13 and 16. The dose response seen indicates that the response to the siRNAs is specific to the siRNA and not generated by a non-specific siRNA response. The results can be seen in FIG. 38. Blunt end siRNAs tested in NIH3T3 cells showed a specific dose response. (See FIG. 39).

Example 20

Effect of siRNAs on VEGF mRNA Expression

Figure 40A:
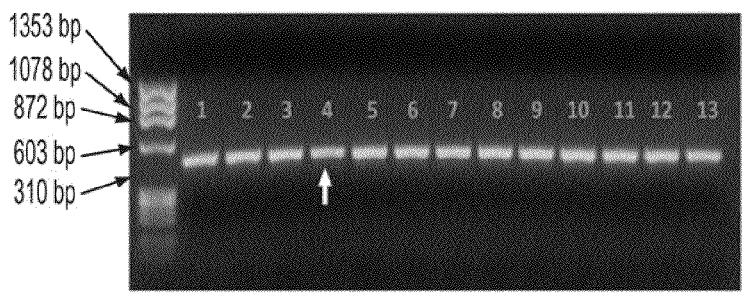
FIG. 40 depicts the effect of siRNAs on VEGF mRNA message in ARPE19 cells
Figure 40B:
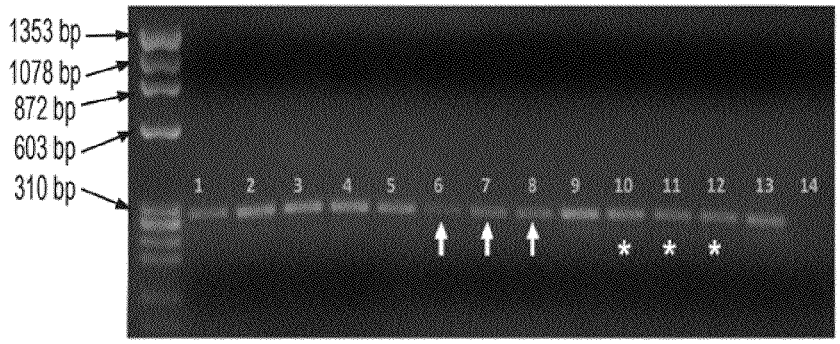
Figure 40C:
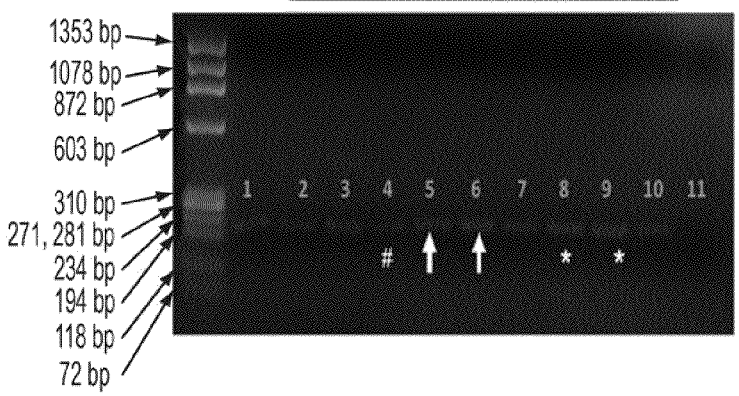
Figure 41:
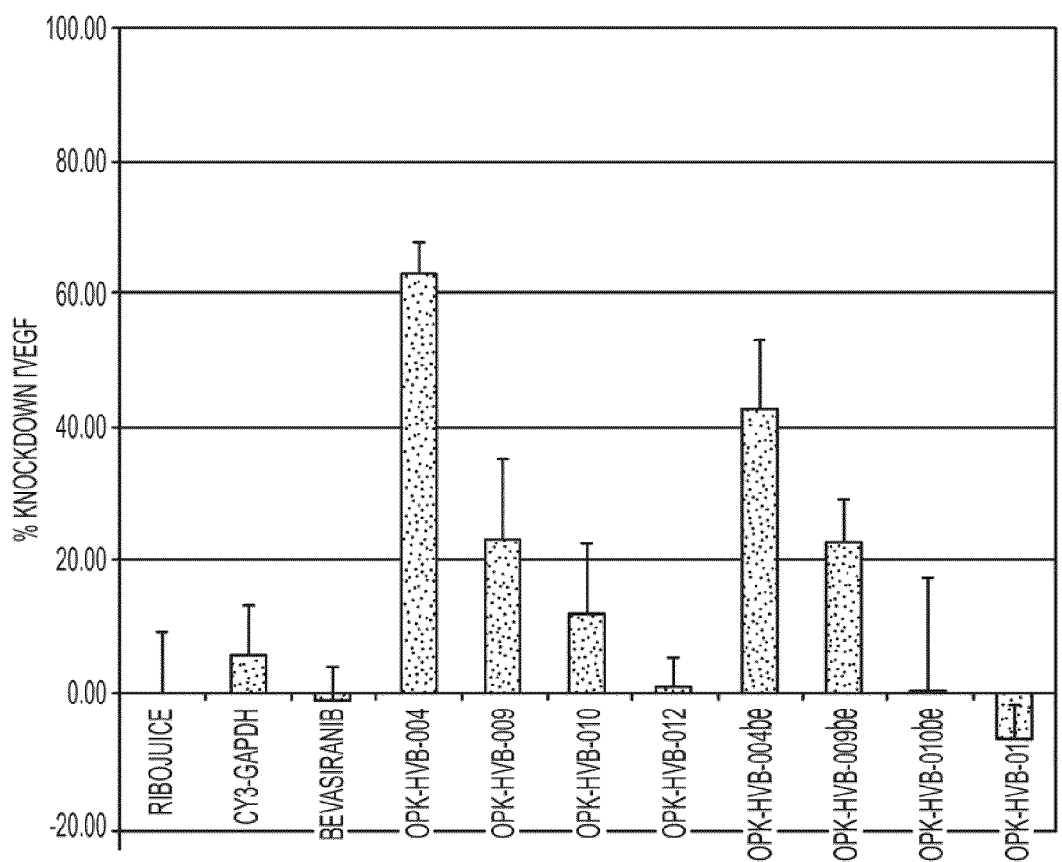
FIG. 41 depicts the effect of siRNAs on VEGF expression in C6 cells.

ARPE19 cells were transfected with siRNAs (final concentration siRNA=25 nM). Cells were treated with 10 ng/mL TGFβII to upregulate production of hVEGF. RNA was isolated from cells and reverse transcription PCR was performed to amplify GAPDH (FIG. 40A; 472 bp fragment), VEGF$_{165}$ (FIG. 40B; 284 bp fragment) and VEGF$_{165b}$ (FIG. 40C; 199 bp fragment). The Cy3-GAPDH siRNA (FIG. 40A, Lane 4) silenced GAPDH message whereas the other treatments had no effect. OPK-HVB-004, OPK-HVB-009 and OPK-HVB-010 (FIG. 40B, Lanes 6, 7 and 8) and OPK-HVB-004be, OPK-HVB-009be and OPK-HVB-010be (FIG. 40B, Lanes 10, 11 and 12) silenced VEGF$_{165}$ message. Bevasiranib (FIG. 40C, Lane 4) silenced VEGF$_{165b}$ whereas OPK-HVB-004, OPK-HVB-009, OPK-HVB-004be and OPK-HVB-009be (FIG. 13C, Lanes 5, 6, 8 and 9) preserved levels of VEGF$_{165b}$ (See FIG. 40).

Example 21

Efficacy of siRNAs in Rat C6 Cells

Rat C6 cells were transfected with siRNAs (final concentration siRNA=25 nM). Cells were treated with 10 ng/mL TGFβII to upregulate production of rat VEGF. Levels of total secreted VEGF were measured in media via ELISA. Percent knockdown reflects the level of VEGF produced by the cells relative to cells treated with RiboJuice™ OPK-HVB-004 and OPK-HVB-004be were the most effective in reducing levels of rat VEGF.

The invention claimed is:

1. A method of treating age-related macular degeneration in a subject comprising: administering to a subject an effective amount of a short interfering ribonucleic acid (siRNA) comprising a sense RNA strand and an antisense RNA strand, wherein the sense and the antisense RNA strands form an RNA duplex, wherein the sense RNA strand consists of a nucleotide sequence of SEQ ID NO: 119, and the antisense strand consists of a nucleotide sequence of SEQ ID NO: 120, such that angiogenesis associated with the angiogenic disease is inhibited.

2. The method of claim 1, wherein the siRNA is administered in combination with a pharmaceutical agent for treating the age-related macular degeneration, which pharmaceutical agent is different from the short interfering ribonucleic acid (siRNA).

3. The method of claim 1, wherein the pharmaceutical composition is administered to a subject in combination with another therapeutic method designed to treat the age-related macular degeneration.

4. A method of inhibiting expression of human vascular endothelial growth factor (VEGF) comprising: administering to a subject an effective amount of a short interfering ribonucleic acid (siRNA) comprising a sense RNA strand and an antisense RNA strand, wherein the sense and the antisense RNA strands form an RNA duplex, wherein the sense RNA strand consists of a nucleotide sequence of SEQ ID NO: 119, and the antisense strand consists of a nucleotide sequence of SEQ ID NO: 120.

5. The method of claim 4, wherein the effective amount comprises from about 1 nM to about 100 nM of the short interfering ribonucleic acid (siRNA).

6. The method of claim 4, wherein the pharmaceutical composition further comprises a delivery reagent.

7. The method of claim 4, wherein the delivery agent is selected from the group consisting of lipofectin, lipofectamine, cellfectin, polycations, and liposomes.

8. The method of claim 7, wherein the delivery agent is a liposome.

9. The method of claim 8, wherein the liposome comprises a ligand which targets the liposome to cells at or near the site of angiogenesis.

10. The method of claim 9, wherein the ligand binds to receptors on tumor cells or vascular endothelial cells.

11. The method of claim 9, wherein the ligand comprises a monoclonal antibody.

12. The method of claim 8, wherein the liposome is modified with an opsonization-inhibition moiety.

13. The method of claim 12, wherein the opsonization-inhibiting moiety comprises a PEG, PPG, or derivatives thereof.

14. The method of claim 4, wherein the short interfering ribonucleic acid (siRNA) is expressed from a recombinant plasmid.

15. The method of claim 4, wherein the short interfering ribonucleic acid (siRNA) is expressed from a recombinant viral vector.

16. The method of claim 15, wherein the recombinant viral vector comprises an adenoviral vector, an adeno-associated viral vector, a lentiviral vector, a retroviral vector, or a herpes virus vector.

17. The method of claim 16, wherein the recombinant viral vector is pseudotyped with surface proteins from vesicular stomatitis virus, rabies virus, Ebola virus, or Mokola virus.

18. The method of claim 15, wherein the recombinant viral vector comprises an adeno-associated viral vector.

19. A method of degrading human vascular endothelial growth factor (VEGF) mRNA comprising: administering to a subject an effective amount of a short interfering ribonucleic acid (siRNA) comprising a sense RNA strand and an antisense RNA strand, wherein the sense and the antisense RNA strands form an RNA duplex, wherein the sense RNA strand consists of a nucleotide sequence that consists of SEQ ID NO: 119, and the antisense strand consists of a nucleotide sequence that consists of SEQ ID NO: 120.

* * * * *

SEQUENCE LISTING

```
<160> NUMBER OF SEQ ID NOS: 138

<210> SEQ ID NO 1
<211> LENGTH: 2250
<212> TYPE: DNA
<213> ORGANISM: Mus musculus

<400> SEQUENCE: 1
tgagccaggc tggcaggaag gagcctccct cagggtttcg ggaaccagac ctctcaccgg    60
aaagaccgat taaccatgtc accaccacgc catcatcgtc accgttgaca gaacagtcct   120
taatccagaa agcctgacat gaaggaagag gagactcttc gaggagcact ttgggtccgg   180
agggcgagac tccggcagac gcattccgg gcaggtgacc aagcacggtc cctcgtggga    240
ctggattcgc cattttctta tatctgctgc taaatcgcca agcccggaag attagggttg   300
tttctgggat tcctgtagac acacccaccc acatacacac atatatatat attatatata   360
taaataaata tatatgtttt atatataaaa tatatatata ttctttttt taaattaact    420 ctgctaatgt tattggtgtc ttcactggat atgtttgact gctgtggact tgtgttggga   480
ggaggatgtc ctcactcgga tgccgacatg ggagacaatg ggatgaaagg cttcagtgtg   540
gtctgagaga ggccgaagtc cttttgcctg ccggggagca agcaaggcca gggcacgggg   600
gcacattggc tcacttccag aaacacgaca aacccattcc tggccctgag tcaagaggac   660
agagagacag atgatgacac agaaagagat aaagatgccg gttccaacca gaagtttggg   720
gagcctcagg acatggcatg cttgtggat ccccatgata gtctacaaaa gcaccccgcc   780
cctctgggca ctgcctggaa gaatcgggag cctggccagc cttcagctcg ctcctccact   840
tctgaggggc ctaggaggcc tcccacaggt gtcccggcaa gagaagacac ggtggtggaa   900
gaagaggcct ggtaatggcc cctcctcctg ggacccttc gtcctctcct tacccacct    960 cctgggtaca gcccaggagg accttgtgtg atcagaccat tgaaaccact aattctgtcc  1020
ccaggagact tggctctgtg tgtgagtggc ttacccttcc tcatcttccc ttcccaaggc  1080
acagagcaat ggggcaggac ccgcaagccc ctcacggagg cagagaaaag agaaagtgtt  1140
ttatatacgg tacttattta atagcccttt ttaattagaa attaaaacag ttaatttaat  1200
taaagagtag ggttttttc agtattcttg gttaatattt aattcaact atttatgaga   1260 tgtatctctc gctctctctt atttgtactt atgtgtgtgt gtgtgtgtgt gtgtgtgt    1320 gtgtgtgtgt gtatgaaatc tgtgtttcca atctctctct cccagatcgg tgacagtcac  1380
tagcttgtcc tgagaagata tttaattttg ctaacactca gctctgccct cccttgtccc  1440
caccacacat tcctttgaaa taaggtttca atatacattt acatactata tatatatttg  1500
gcaacttgtg tttgtatata aatatatata tatatatatg tttatgtata tatgtgattc  1560
```

```
tgataaaata gacattgcta ttctgttttt tatatgtaaa acaaaacaa gaaaaataga      1620 gaattctaca tactaaatct ctctccttt ttaattttaa tatttgttat catttattta      1680
ttggtgctac tgtttatccg taataattgt gggggaaaaa gatattaaca tcacgtctt      1740 gtctctagag cagttttccg agatattccg tagtacatat ttatttttaa acagcaacaa     1800
agaaatacag atatatctta aaaaaaaagc attttgtatt aaagaattga attctgatct     1860
caaagctctc cctggtctct ccttctctcc tgggccctcc tgtctcgctt ccctcctcc      1920 tttggggtac atagttttg tcttaggttt gagaagcagt ccctggagta aatatgggg      1980 tgacccatcc attcctgggc ggagggaga tggctccttt gccaagggtc ctcacactac       2040
gtggtactct gttccttgtc agacaaggat gggggcatgt ctccaggtgc taactggaga     2100
tcggagagag ctgttggctg cagctggcca ggatttgggc atgccgggga catgggaggc     2160
tgtgagccca gcatgcagtt tacttctggg tgctaaatgg aagagtccag taaaaagagt     2220
cttgcccatg ggattccatt ccgctttgtg                                     2250

<210> SEQ ID NO 2
<211> LENGTH: 444
<212> TYPE: DNA
<213> ORGANISM: Homo sapiens

<400> SEQUENCE: 2
atgaactttc tgctgtcttg ggtgcattgg agccttgcct tgctgctcta cctccaccat       60
gccaagtggt cccaggctgc acccatggca gaaggaggag gcagaatca tcacgaagtg      120 gtgaagttca tggatgtcta tcagcgcagc tactgccatc caatcgagac cctggtggac      180
atcttccagg agtaccctga tgagatcgag tacatcttca agccatcctg tgtgcccctg     240
atgcgatgcg ggggctgctg caatgacgag gcctggagt gtgtgcccac tgaggagtcc      300
aacatcacca tgcagattat gcggatcaaa cctcaccaag gccagcacat aggagagatg     360
agcttcctac agcacaacaa atgtgaatgc agaccaaaga aagatagagc aagacaagaa     420
aaatgtgaca agccgaggcg gtga                                           444

<210> SEQ ID NO 3
<211> LENGTH: 576
<212> TYPE: DNA
<213> ORGANISM: Homo sapiens

<400> SEQUENCE: 3
atgaactttc tgctgtcttg ggtgcattgg agccttgcct tgctgctcta cctccaccat       60
gccaagtggt cccaggctgc acccatggca gaaggaggag gcagaatca tcacgaagtg      120 gtgaagttca tggatgtcta tcagcgcagc tactgccatc caatcgagac cctggtggac      180
atcttccagg agtaccctga tgagatcgag tacatcttca agccatcctg tgtgcccctg     240
atgcgatgcg ggggctgctg caatgacgag gcctggagt gtgtgcccac tgaggagtcc      300
aacatcacca tgcagattat gcggatcaaa cctcaccaag gccagcacat aggagagatg     360
agcttcctac agcacaacaa atgtgaatgc agaccaaaga aagatagagc aagacaagaa     420
aatccctgtg ggccttgctc agagcggaga aagcatttgt ttgtacaaga tccgcagacg     480
tgtaaatgtt cctgcaaaaa cacagactcg cgttgcaagg cgaggcagct tgagttaaac     540
gaacgtactt gcagatgtga caagccgagg cggtga                              576

<210> SEQ ID NO 4
<211> LENGTH: 648
<212> TYPE: DNA
```

<213> ORGANISM: Homo sapiens

<400> SEQUENCE: 4

| | | | | | |
|---|---|---|---|---|---|
| atgaactttc | tgctgtcttg | ggtgcattgg | agccttgcct | tgctgctcta | cctccaccat | 60 |
| gccaagtggt | cccaggctgc | acccatggca | gaaggaggag | ggcagaatca | tcacgaagtg | 120 |
| gtgaagttca | tggatgtcta | tcagcgcagc | tactgccatc | caatcgagac | cctggtggac | 180 |
| atcttccagg | agtaccctga | tgagatcgag | tacatcttca | agccatcctg | tgtgccctg | 240 |
| atgcgatgcg | ggggctgctg | caatgacgag | ggcctggagt | gtgtgcccac | tgaggagtcc | 300 |
| aacatcacca | tgcagattat | gcggatcaaa | cctcaccaag | gccagcacat | aggagagatg | 360 |
| agcttcctac | agcacaacaa | atgtgaatgc | agaccaaaga | agatagagc | aagacaagaa | 420 |
| aaaaaatcag | ttcgaggaaa | gggaaggggg | caaaaacgaa | agcgcaagaa | atcccggtat | 480 |
| aagtcctgga | gcgttccctg | tgggccttgc | tcagagcgga | gaaagcattt | gtttgtacaa | 540 |
| gatccgcaga | cgtgtaaatg | ttcctgcaaa | aacacagact | cgcgttgcaa | ggcgaggcag | 600 |
| cttgagttaa | cgaacgtac | ttgcagatgt | gacaagccga | ggcggtga | | 648 |

<210> SEQ ID NO 5
<211> LENGTH: 670
<212> TYPE: DNA
<213> ORGANISM: Homo sapiens

<400> SEQUENCE: 5

| | | | | | |
|---|---|---|---|---|---|
| gccttgctgc | tctacctcca | ccatgccaag | tggtcccagg | ctgcacccat | ggcagaagga | 60 |
| ggagggcaga | atcatcacga | agtggtgaag | ttcatggatg | tctatcagcg | cagctactgc | 120 |
| catccaatcg | agaccctggt | ggacatcttc | caggagtacc | ctgatgagat | cgagtacatc | 180 |
| ttcaagccat | cctgtgtgcc | cctgatgcga | tgcgggggct | gctgcaatga | cgagggcctg | 240 |
| gagtgtgtgc | ccactgagga | gtccaacatc | accatgcaga | ttatgcggat | caaacctcac | 300 |
| caaggccagc | acataggaga | gatgagcttc | ctacagcaca | acaaatgtga | atgcagacca | 360 |
| aagaaggata | gagcaagaca | agaaaaaaaa | tcagttcgag | gaaagggaaa | ggggcaaaaa | 420 |
| cgaaagcgca | agaaatcccg | gtataagtcc | tggagcgttt | acgttggtgc | cgctgctgt | 480 |
| ctaatgccct | ggagcctccc | tggccccat | ccctgtgggc | cttgctcaga | gcggagaaag | 540 |
| catttgtttg | tacaagatcc | gcagacgtgt | aaatgttcct | gcaaaaacac | agactcgcgt | 600 |
| tgcaaggcga | ggcagcttga | gttaaacgaa | cgtacttgca | gatgtgacaa | gccgaggcgg | 660 |
| tgatgaatga | | | | | | 670 |

<210> SEQ ID NO 6
<211> LENGTH: 1137
<212> TYPE: DNA
<213> ORGANISM: Homo sapiens

<400> SEQUENCE: 6

| | | | | | |
|---|---|---|---|---|---|
| atgctcattg | tccagactgg | ggtcagatca | gcaaacaaag | ggcctctgat | ggtgattgtt | 60 |
| gaatattgca | atatggaaa | tctatccaac | tacctcaaga | gcaaatatga | cttattttt | 120 |
| ctcgacaagg | atgtggcatc | acacatggag | cgtaagaaag | aaaaaatgga | gccaggcctg | 180 |
| gaacaaggca | gaaaccaaa | actagatagc | atcaccagca | gcgagagctt | tgggagctcc | 240 |
| aagtttcagg | aagataaaaa | tctgagtgat | gttgaggaag | aggaggattc | tgatggtttc | 300 |
| taccaggagc | ccatcactat | ggaagatctg | atttcttaca | gttttcaagt | ggccagaggc | 360 |
| atgaagtttc | tgtcttccag | aaagtgcatt | cattgggacc | tggcagcaag | aaacattctt | 420 |

| ttatctgaga acaatgtggt gaagatttgt gattttggcc ttgcccagga tatttacaag | 480 |
| aacgccgatt atgtgagaaa aggaggtggg tctccatacc caggagtgca aatggatgag | 540 |
| cacttctgca gttgcctgag ggaaggcatg aggatgagag ctgctgagta ctccactcct | 600 |
| gaaatctatc agatcatgct ggactgcagg cacaaagacc caaagaaag gccaagattt | 660 |
| gcagaacttg tggaaaaact agaaatagt gggtttacat actcaactcc tgccttctct | 720 |
| gaggacttct tcaaggaagg tatttcagct cccaagttta gttcaggaag ctctgatgat | 780 |
| gtcagatacg taaatgcttt caagttcatg agcctggaaa gaatcaaaac ctttgaagaa | 840 |
| cttttgccaa atgccacctc catgtttgat gactaccagg gggacagcag cgctctgctg | 900 |
| gcctctccca tgctgaagcg cttcaccagg actgacagca acccaaggc ctcgctcaag | 960 |
| attgacttga gactaactag caaaagtaag aagtcggggc tttctgatgt cagcaggccc | 1020 |
| agtttctgcc attccaacag tgggcacatc agcaaaggca agggcaggtt cacctacgac | 1080 |
| aacgccgagc tggaaaggaa gacggcgtgc tgctccccgc ccctctggga gttgtag | 1137 |

```
<210> SEQ ID NO 7
<211> LENGTH: 5830
<212> TYPE: DNA
<213> ORGANISM: Homo sapiens

<400> SEQUENCE: 7
```

| actgagtccc gggaccccgg gagagcggtc agtgtgtggt cgctgcgttt cctctgcctg | 60 |
| cgccgggcat cacttgcgcg ccgcagaaag tccgtctggc agcctggata tcctctccta | 120 |
| ccggcacccg cagacgcccc tgcagccgcc ggtcggcgcc cgggctccct agccctgtgc | 180 |
| gctcaactgt cctgcgctgc ggggtgccgc gagttccacc tccgcgcctc cttctctaga | 240 |
| caggcgctgg gagaaagaac cggctcccga gttctgggca tttcgcccgg ctcgaggtgc | 300 |
| aggatgcaga gcaaggtgct gctggccgtc gccctgtggc tctgcgtgga gacccgggcc | 360 |
| gcctctgtgg gtttgcctag tgtttctctt gatctgccca ggctcagcat acaaaaagac | 420 |
| atacttacaa ttaaggctaa tacaactctt caaattactt gcaggggaca gagggacttg | 480 |
| gactggcttt ggcccaataa tcagagtggc agtgagcaaa gggtggaggt gactgagtgc | 540 |
| agcgatggcc tcttctgtaa gacactcaca attccaaaag tgatcggaaa tgacactgga | 600 |
| gcctacaagt gcttctaccg ggaaactgac ttggcctcgg tcatttatgt ctatgttcaa | 660 |
| gattacagat ctccatttat tgcttctgtt agtgaccaac atggagtcgt gtacattact | 720 |
| gagaacaaaa acaaaactgt ggtgattcca tgtctcgggt ccatttcaaa tctcaacgtg | 780 |
| tcactttgtg caagataccc agaaaagaga tttgttcctg atggtaacag aatttcctgg | 840 |
| gacagcaaga agggctttac tattcccagc tacatgatca gctatgctgg catggtcttc | 900 |
| tgtgaagcaa aaattaatga tgaaagttac cagtctatta tgtacatagt tgtcgttgta | 960 |
| gggtatagga tttatgatgt ggttctgagt ccgtctcatg gaattgaact atctgttgga | 1020 |
| gaaaagcttg tcttaaattg tacagcaaga actgaactaa atgtggggat tgacttcaac | 1080 |
| tgggaatacc cttcttcgaa gcatcagcat aagaaacttg taaaccgaga cctaaaaacc | 1140 |
| cagtctggga gtgagatgaa gaaattttg agcaccttaa ctatagatgg tgtaaccgg | 1200 |
| agtgaccaag gattgtacac ctgtgcagca tccagtgggc tgatgaccaa gaagaacagc | 1260 |
| acatttgtca gggtccatga aaaacctttt gttgcttttg gaagtggcat ggaatctctg | 1320 |
| gtggaagcca cggtggggga gcgtgtcaga atccctgcga gtaccttgg ttacccaccc | 1380 |
| ccagaaataa aatggtataa aaatggaata ccccttgagt ccaatcacac aattaaagcg | 1440 |

```
gggcatgtac tgacgattat ggaagtgagt gaaagagaca caggaaatta cactgtcatc   1500
cttaccaatc ccatttcaaa ggagaagcag agccatgtgg tctctctggt tgtgtatgtc   1560 ccacccccaga ttggtgagaa atctctaatc tctcctgtgg attcctacca gtacggcacc  1620
actcaaacgc tgacatgtac ggtctatgcc attcctcccc cgcatcacat ccactggtat   1680
tggcagttgg aggaagagtg cgccaacgag cccagccaag ctgtctcagt gacaaaccca   1740
tacccttgtg aagaatggag aagtgtggag gacttccagg gaggaaataa aattgaagtt   1800
aataaaaatc aatttgctct aattgaagga aaaaacaaaa ctgtaagtac ccttgttatc   1860
caagcggcaa atgtgtcagc tttgtacaaa tgtgaagcgg tcaacaaagt cgggagagga   1920
gagagggtga tctccttcca cgtgaccagg ggtcctgaaa ttactttgca acctgacatg   1980
cagcccactg agcaggagag cgtgtctttg tggtgcactg cagacagatc tacgtttgag   2040
aacctcacat ggtacaagct tggcccacag cctctgccaa tccatgtggg agagttgccc   2100
acacctgttt gcaagaactt ggatactctt tggaaattga atgccaccat gttctctaat   2160
agcacaaatg acattttgat catggagctt aagaatgcat ccttgcagga ccaaggagac   2220
tatgtctgcc ttgctcaaga caggaagacc aagaaaagac attgcgtggt caggcagctc   2280
acagtcctag agcgtgtggc acccacgatc acaggaaacc tggagaatca gacgacaagt   2340
attggggaaa gcatcgaagt ctcatgcacg gcatctggga atccccctcc acagatcatg   2400
tggtttaaag ataatgagac ccttgtagaa gactcaggca ttgtattgaa ggatgggaac   2460
cggaacctca ctatccgcag agtgaggaag gaggacgaag gcctctacac ctgccaggca   2520
tgcagtgttc ttggctgtgc aaaagtggag gcattttca taatagaagg tgcccaggaa   2580
aagacgaact tggaaatcat tattctagta ggcacggcgg tgattgccat gttcttctgg   2640
ctacttcttg tcatcatcct acggaccgtt aagcgggcca atggagggga actgaagaca   2700
ggctacttgt ccatcgtcat ggatccagat gaactcccat tggatgaaca ttgtgaacga   2760
ctgccttatg atgccagcaa atgggaattc cccagagacc ggctgaagct aggtaagcct   2820
cttggccgtg gtgcctttgg ccaagtgatt gaagcagatg cctttggaat tgacaagaca   2880
gcaacttgca ggacagtagc agtcaaaatg ttgaaagaag gagcaacaca cagtgagcat   2940
cgagctctca tgtctgaact caagatcctc attcatattg gtcaccatct caatgtggtc   3000
aaccttctag gtgcctgtac caagccagga gggccactca tggtgattgt ggaattctgc   3060
aaatttggaa acctgtccac ttacctgagg agcaagagaa atgaatttgt ccccctacaag  3120 accaaagggg cacgattccg tcaagggaaa gactacgttg gagcaatccc tgtggatctg   3180
aaacggcgct tggacagcat caccagtagc cagagctcag ccagctctgg atttgtggag   3240
gagaagtccc tcagtgatgt agaagaagag gaagctcctg aagatctgta taaggacttc   3300
ctgaccttgg agcatctcat ctgttacagc ttccaagtgg ctaagggcat ggagttcttg   3360
gcatcgcgaa agtgtatcca cagggacctg gcggcacgaa atatcctctt atcggagaag   3420
aacgtggtta aaatctgtga ctttggcttg gcccgggata tttataaaga tccagattat   3480
gtcagaaaag gagatgctcg cctcccttg aaatggatgg ccccagaaac aatttttgac   3540
agagtgtaca caatccagag tgacgtctgg tcttttggtg ttttgctgtg ggaaatattt   3600
tccttaggct cttctccata tcctgggta aagattgatg aagaattttg taggcgattg   3660
aaagaaggaa ctagaatgag ggcccctgat tatactacac cagaaatgta ccagaccatg   3720
ctggactgct ggcacgggga gcccagtcag agacccacgt tttcagagtt ggtggaacat   3780
ttgggaaatc tcttgcaagc taatgctcag caggatggca agactacat tgttcttccg   3840
```

```
atatcagaga ctttgagcat ggaagaggat tctggactct ctctgcctac ctcacctgtt    3900
tcctgtatgg aggaggagga agtatgtgac cccaaattcc attatgacaa cacagcagga    3960
atcagtcagt atctgcagaa cagtaagcga aagagccggc ctgtgagtgt aaaaacattt    4020
gaagatatcc cgttagaaga accagaagta aaagtaatcc cagatgacaa ccagacggac    4080
agtggtatgg ttcttgcctc agaagagctg aaaactttgg aagacagaac caaattatct    4140
ccatcttttg gtggaatggt gcccagcaaa gcagggagt ctgtggcatc tgaaggctca    4200
aaccagacaa gcggctacca gtccggatat cactccgatg acacagacac caccgtgtac    4260
tccagtgagg aagcagaact tttaaagctg atagagattg gagtgcaaac cggtagcaca    4320
gcccagattc tccagcctga ctcggggacc acactgagct ctcctcctgt ttaaaaggaa    4380
gcatccacac cccaactccc ggacatcaca tgagaggtct gctcagattt tgaagtgttg    4440
ttctttccac cagcaggaag tagccgcatt tgattttcat ttcgacaaca gaaaaaggac    4500
ctcggactgc agggagccag tcttctaggc atatcctgga agaggcttgt gacccaagaa    4560
tgtgtctgtg tcttctccca gtgttgacct gatcctcttt tttcattcat ttaaaaagca    4620
ttatcatgcc cctgctgcgg gtctcaccat gggtttagaa caaagagctt caagcaatgg    4680
ccccatcctc aaagaagtag cagtacctgg ggagctgaca cttctgtaaa actagaagat    4740
aaaccaggca acgtaagtgt tcgaggtgtt gaagatggga aggatttgca gggctgagtc    4800
tatccaagag gctttgttta ggacgtgggt cccaagccaa gccttaagtg tggaattcgg    4860
attgatagaa aggaagacta acgttacctt gctttggaga gtactggagc ctgcaaatgc    4920
attgtgtttg ctctggtgga ggtgggcatg gggtctgttc tgaaatgtaa agggttcaga    4980
cggggtttct ggttttagaa ggttgcgtgt tcttcgagtt gggctaaagt agagttcgtt    5040
gtgctgtttc tgactcctaa tgagagttcc ttccagaccg ttagctgtct ccttgccaag    5100
ccccaggaag aaaatgatgc agctctggct ccttgtctcc caggctgatc ctttattcag    5160
aataccacaa agaaaggaca ttcagctcaa ggctccctgc cgtgttgaag agttctgact    5220
gcacaaacca gcttctggtt tcttctggaa tgaataccct catatctgtc ctgatgtgat    5280
atgtctgaga ctgaatgcgg gaggttcaat gtgaagctgt gtgtggtgtc aaagtttcag    5340
gaaggatttt accctttgt tcttccccct gtccccaacc cactctcacc ccgcaaccca    5400
tcagtatttt agttatttgg cctctactcc agtaaacctg attgggtttg ttcactctct    5460
gaatgattat tagccagact tcaaaattat tttatagccc aaattataac atctattgta    5520
ttatttagac ttttaacata tagagctatt tctactgatt tttgcccttg ttctgtcctt    5580
tttttcaaaa aagaaaatgt gttttttgtt tggtaccata gtgtgaaatg ctgggaacaa    5640
tgactataag acatgctatg gcacatatat ttatagtctg tttatgtaga aacaaatgta    5700
atatattaaa gccttatata taatgaactt tgtactattc acattttgta tcagtattat    5760
gtagcataac aaaggtcata atgctttcag caattgatgt cattttatta aagaacattg    5820
aaaaacttga                                                           5830
```

<210> SEQ ID NO 8
<211> LENGTH: 19
<212> TYPE: DNA
<213> ORGANISM: Homo sapiens

<400> SEQUENCE: 8
tcatcacgaa gtggtgaag                                                    19

<210> SEQ ID NO 9

```
<211> LENGTH: 21
<212> TYPE: RNA
<213> ORGANISM: Homo sapiens

<400> SEQUENCE: 9
ucaucacgaa guggugaagu u                                              21

<210> SEQ ID NO 10
<211> LENGTH: 21
<212> TYPE: RNA
<213> ORGANISM: Homo sapiens

<400> SEQUENCE: 10
uuaguagugc uucaccacuu c                                              21

<210> SEQ ID NO 11
<211> LENGTH: 21
<212> TYPE: DNA
<213> ORGANISM: Artificial Sequence
<220> FEATURE:
<223> OTHER INFORMATION: DNA/RNA hybrid

<400> SEQUENCE: 11
ucaucacgaa guggugaagt t                                              21

<210> SEQ ID NO 12
<211> LENGTH: 21
<212> TYPE: DNA
<213> ORGANISM: Artificial Sequence
<220> FEATURE:
<223> OTHER INFORMATION: DNA/RNA hybrid

<400> SEQUENCE: 12
ttaguagugc uucaccacuu c                                              21

<210> SEQ ID NO 13
<211> LENGTH: 21
<212> TYPE: DNA
<213> ORGANISM: Homo sapiens

<400> SEQUENCE: 13
aacgtacttg cagatgtgac a                                              21

<210> SEQ ID NO 14
<211> LENGTH: 19
<212> TYPE: DNA
<213> ORGANISM: Homo sapiens

<400> SEQUENCE: 14
gttcatggat gtctatcag                                                 19

<210> SEQ ID NO 15
<211> LENGTH: 19
<212> TYPE: DNA
<213> ORGANISM: Homo sapiens

<400> SEQUENCE: 15
tcgagaccct ggtggacat                                                 19

<210> SEQ ID NO 16
<211> LENGTH: 19
<212> TYPE: DNA
<213> ORGANISM: Homo sapiens

<400> SEQUENCE: 16
```

-continued tgacgagggc ctggagtgt                                           19

<210> SEQ ID NO 17
<211> LENGTH: 19
<212> TYPE: DNA
<213> ORGANISM: Homo sapiens

<400> SEQUENCE: 17
tgacgagggc ctggagtgt                                           19

<210> SEQ ID NO 18
<211> LENGTH: 19
<212> TYPE: DNA
<213> ORGANISM: Homo sapiens

<400> SEQUENCE: 18
catcaccatg cagattatg                                           19

<210> SEQ ID NO 19
<211> LENGTH: 19
<212> TYPE: DNA
<213> ORGANISM: Homo sapiens

<400> SEQUENCE: 19
acctcaccaa ggccagcac                                           19

<210> SEQ ID NO 20
<211> LENGTH: 19
<212> TYPE: DNA
<213> ORGANISM: Homo sapiens

<400> SEQUENCE: 20
ggccagcaca taggagaga                                           19

<210> SEQ ID NO 21
<211> LENGTH: 19
<212> TYPE: DNA
<213> ORGANISM: Homo sapiens

<400> SEQUENCE: 21
caaatgtgaa tgcagacca                                           19

<210> SEQ ID NO 22
<211> LENGTH: 19
<212> TYPE: DNA
<213> ORGANISM: Homo sapiens

<400> SEQUENCE: 22
atgtgaatgc agaccaaag                                           19

<210> SEQ ID NO 23
<211> LENGTH: 19
<212> TYPE: DNA
<213> ORGANISM: Homo sapiens

<400> SEQUENCE: 23
tgcagaccaa agaaagata                                           19

<210> SEQ ID NO 24
<211> LENGTH: 19
<212> TYPE: DNA
<213> ORGANISM: Homo sapiens

<400> SEQUENCE: 24
agaaagatag agcaagaca					19

<210> SEQ ID NO 25
<211> LENGTH: 19
<212> TYPE: DNA
<213> ORGANISM: Homo sapiens

<400> SEQUENCE: 25
gaaagataga gcaagacaa					19

<210> SEQ ID NO 26
<211> LENGTH: 19
<212> TYPE: DNA
<213> ORGANISM: Homo sapiens

<400> SEQUENCE: 26
gatagagcaa gacaagaaa					19

<210> SEQ ID NO 27
<211> LENGTH: 19
<212> TYPE: DNA
<213> ORGANISM: Homo sapiens

<400> SEQUENCE: 27
gacaagaaaa tccctgtgg					19

<210> SEQ ID NO 28
<211> LENGTH: 19
<212> TYPE: DNA
<213> ORGANISM: Homo sapiens

<400> SEQUENCE: 28
gaaaatccct gtgggcctt					19

<210> SEQ ID NO 29
<211> LENGTH: 19
<212> TYPE: DNA
<213> ORGANISM: Homo sapiens

<400> SEQUENCE: 29
aatccctgtg ggccttgct					19

<210> SEQ ID NO 30
<211> LENGTH: 19
<212> TYPE: DNA
<213> ORGANISM: Homo sapiens

<400> SEQUENCE: 30
tccctgtggg ccttgctca					19

<210> SEQ ID NO 31
<211> LENGTH: 19
<212> TYPE: DNA
<213> ORGANISM: Homo sapiens

<400> SEQUENCE: 31
gcatttgttt gtacaagat					19

<210> SEQ ID NO 32
<211> LENGTH: 19
<212> TYPE: DNA
<213> ORGANISM: Homo sapiens

<400> SEQUENCE: 32

| | |
|---|---|
| gatccgcaga cgtgtaaat | 19 |

<210> SEQ ID NO 33
<211> LENGTH: 19
<212> TYPE: DNA
<213> ORGANISM: Homo sapiens

<400> SEQUENCE: 33

| | |
|---|---|
| atgttcctgc aaaaacaca | 19 |

<210> SEQ ID NO 34
<211> LENGTH: 19
<212> TYPE: DNA
<213> ORGANISM: Homo sapiens

<400> SEQUENCE: 34

| | |
|---|---|
| tgttcctgca aaaacacag | 19 |

<210> SEQ ID NO 35
<211> LENGTH: 19
<212> TYPE: DNA
<213> ORGANISM: Homo sapiens

<400> SEQUENCE: 35

| | |
|---|---|
| aaacacagac tcgcgttgc | 19 |

<210> SEQ ID NO 36
<211> LENGTH: 19
<212> TYPE: DNA
<213> ORGANISM: Homo sapiens

<400> SEQUENCE: 36

| | |
|---|---|
| aacacagact cgcgttgca | 19 |

<210> SEQ ID NO 37
<211> LENGTH: 19
<212> TYPE: DNA
<213> ORGANISM: Homo sapiens

<400> SEQUENCE: 37

| | |
|---|---|
| acacagactc gcgttgcaa | 19 |

<210> SEQ ID NO 38
<211> LENGTH: 19
<212> TYPE: DNA
<213> ORGANISM: Homo sapiens

<400> SEQUENCE: 38

| | |
|---|---|
| cacagactcg cgttgcaag | 19 |

<210> SEQ ID NO 39
<211> LENGTH: 19
<212> TYPE: DNA
<213> ORGANISM: Homo sapiens

<400> SEQUENCE: 39

| | |
|---|---|
| ggcgaggcag cttgagtta | 19 |

<210> SEQ ID NO 40
<211> LENGTH: 19
<212> TYPE: DNA
<213> ORGANISM: Homo sapiens

<400> SEQUENCE: 40

| | |
|---|---|
| acgaacgtac ttgcagatg | 19 |

<210> SEQ ID NO 41
<211> LENGTH: 19
<212> TYPE: DNA
<213> ORGANISM: Homo sapiens

<400> SEQUENCE: 41

| | |
|---|---|
| cgaacgtact tgcagatgt | 19 |

<210> SEQ ID NO 42
<211> LENGTH: 19
<212> TYPE: DNA
<213> ORGANISM: Homo sapiens

<400> SEQUENCE: 42

| | |
|---|---|
| cgtacttgca gatgtgaca | 19 |

<210> SEQ ID NO 43
<211> LENGTH: 19
<212> TYPE: DNA
<213> ORGANISM: Homo sapiens

<400> SEQUENCE: 43

| | |
|---|---|
| gtggtcccag gctgcaccc | 19 |

<210> SEQ ID NO 44
<211> LENGTH: 19
<212> TYPE: DNA
<213> ORGANISM: Homo sapiens

<400> SEQUENCE: 44

| | |
|---|---|
| ggaggagggc agaatcatc | 19 |

<210> SEQ ID NO 45
<211> LENGTH: 19
<212> TYPE: DNA
<213> ORGANISM: Homo sapiens

<400> SEQUENCE: 45

| | |
|---|---|
| gtggtgaagt tcatggatg | 19 |

<210> SEQ ID NO 46
<211> LENGTH: 21
<212> TYPE: DNA
<213> ORGANISM: Homo sapiens

<400> SEQUENCE: 46

| | |
|---|---|
| aatcatcacg aagtggtgaa g | 21 |

<210> SEQ ID NO 47
<211> LENGTH: 21
<212> TYPE: DNA
<213> ORGANISM: Homo sapiens

<400> SEQUENCE: 47

| | |
|---|---|
| aagttcatgg atgtctatca g | 21 |

<210> SEQ ID NO 48
<211> LENGTH: 21
<212> TYPE: DNA
<213> ORGANISM: Homo sapiens

<400> SEQUENCE: 48
aatcgagacc ctggtggaca t                                     21

<210> SEQ ID NO 49
<211> LENGTH: 21
<212> TYPE: DNA
<213> ORGANISM: Homo sapiens

<400> SEQUENCE: 49
aatgacgagg gcctggagtg t                                     21

<210> SEQ ID NO 50
<211> LENGTH: 21
<212> TYPE: DNA
<213> ORGANISM: Homo sapiens

<400> SEQUENCE: 50
aacatcacca tgcagattat g                                     21

<210> SEQ ID NO 51
<211> LENGTH: 21
<212> TYPE: DNA
<213> ORGANISM: Homo sapiens

<400> SEQUENCE: 51
aaacctcacc aaggccagca c                                     21

<210> SEQ ID NO 52
<211> LENGTH: 21
<212> TYPE: DNA
<213> ORGANISM: Homo sapiens

<400> SEQUENCE: 52
aaggccagca cataggagag a                                     21

<210> SEQ ID NO 53
<211> LENGTH: 21
<212> TYPE: DNA
<213> ORGANISM: Homo sapiens

<400> SEQUENCE: 53
aacaaatgtg aatgcagacc a                                     21

<210> SEQ ID NO 54
<211> LENGTH: 21
<212> TYPE: DNA
<213> ORGANISM: Homo sapiens

<400> SEQUENCE: 54
aaatgtgaat gcagaccaaa g                                     21

<210> SEQ ID NO 55
<211> LENGTH: 21
<212> TYPE: DNA
<213> ORGANISM: Homo sapiens

<400> SEQUENCE: 55
aatgcagacc aaagaaagat a                                     21

<210> SEQ ID NO 56
<211> LENGTH: 21
<212> TYPE: DNA
<213> ORGANISM: Homo sapiens

<400> SEQUENCE: 56

-continued aaagaaagat agagcaagac a    21

<210> SEQ ID NO 57
<211> LENGTH: 21
<212> TYPE: DNA
<213> ORGANISM: Homo sapiens

<400> SEQUENCE: 57
aagaaagata gagcaagaca a    21

<210> SEQ ID NO 58
<211> LENGTH: 23
<212> TYPE: DNA
<213> ORGANISM: Homo sapiens

<400> SEQUENCE: 58
aagatagagc aagacaagaa aat    23

<210> SEQ ID NO 59
<211> LENGTH: 23
<212> TYPE: DNA
<213> ORGANISM: Homo sapiens

<400> SEQUENCE: 59
aagacaagaa aatccctgtg ggc    23

<210> SEQ ID NO 60
<211> LENGTH: 23
<212> TYPE: DNA
<213> ORGANISM: Homo sapiens

<400> SEQUENCE: 60
aagaaaatcc ctgtgggcct tgc    23

<210> SEQ ID NO 61
<211> LENGTH: 23
<212> TYPE: DNA
<213> ORGANISM: Homo sapiens

<400> SEQUENCE: 61
aatccctgtg ggccttgctc aga    23

<210> SEQ ID NO 62
<211> LENGTH: 23
<212> TYPE: DNA
<213> ORGANISM: Homo sapiens

<400> SEQUENCE: 62
aagcatttgt ttgtacaaga tcc    23

<210> SEQ ID NO 63
<211> LENGTH: 23
<212> TYPE: DNA
<213> ORGANISM: Homo sapiens

<400> SEQUENCE: 63
aagatccgca gacgtgtaaa tgt    23

<210> SEQ ID NO 64
<211> LENGTH: 23
<212> TYPE: DNA
<213> ORGANISM: Homo sapiens

<400> SEQUENCE: 64
aaatgttcct gcaaaaacac aga    23

<210> SEQ ID NO 65
<211> LENGTH: 23
<212> TYPE: DNA
<213> ORGANISM: Homo sapiens

<400> SEQUENCE: 65
aatgttcctg caaaaacaca gac    23

<210> SEQ ID NO 66
<211> LENGTH: 23
<212> TYPE: DNA
<213> ORGANISM: Homo sapiens

<400> SEQUENCE: 66
aaaaacacag actcgcgttg caa    23

<210> SEQ ID NO 67
<211> LENGTH: 23
<212> TYPE: DNA
<213> ORGANISM: Homo sapiens

<400> SEQUENCE: 67
aaaacacaga ctcgcgttgc aag    23

<210> SEQ ID NO 68
<211> LENGTH: 23
<212> TYPE: DNA
<213> ORGANISM: Homo sapiens

<400> SEQUENCE: 68
aaacacagac tcgcgttgca agg    23

<210> SEQ ID NO 69
<211> LENGTH: 23
<212> TYPE: DNA
<213> ORGANISM: Homo sapiens

<400> SEQUENCE: 69
aacacagact cgcgttgcaa ggc    23

<210> SEQ ID NO 70
<211> LENGTH: 23
<212> TYPE: DNA
<213> ORGANISM: Homo sapiens

<400> SEQUENCE: 70
aaggcgaggc agcttgagtt aaa    23

<210> SEQ ID NO 71
<211> LENGTH: 23
<212> TYPE: DNA
<213> ORGANISM: Homo sapiens

<400> SEQUENCE: 71
aaacgaacgt acttgcagat gtg    23

<210> SEQ ID NO 72
<211> LENGTH: 23
<212> TYPE: DNA
<213> ORGANISM: Homo sapiens

<400> SEQUENCE: 72

```
aacgaacgta cttgcagatg tga                                          23

<210> SEQ ID NO 73
<211> LENGTH: 23
<212> TYPE: DNA
<213> ORGANISM: Homo sapiens

<400> SEQUENCE: 73
aagtggtccc aggctgcacc cat                                          23

<210> SEQ ID NO 74
<211> LENGTH: 23
<212> TYPE: DNA
<213> ORGANISM: Homo sapiens

<400> SEQUENCE: 74
aaggaggagg gcagaatcat cac                                          23

<210> SEQ ID NO 75
<211> LENGTH: 23
<212> TYPE: DNA
<213> ORGANISM: Homo sapiens

<400> SEQUENCE: 75
aagtggtgaa gttcatggat gtc                                          23

<210> SEQ ID NO 76
<211> LENGTH: 23
<212> TYPE: DNA
<213> ORGANISM: Homo sapiens

<400> SEQUENCE: 76
aaaatccctg tgggccttgc tca                                          23

<210> SEQ ID NO 77
<211> LENGTH: 21
<212> TYPE: DNA
<213> ORGANISM: Artificial Sequence
<220> FEATURE:
<223> OTHER INFORMATION: DNA/RNA hybrid

<400> SEQUENCE: 77
accucaccaa ggccagcact t                                            21

<210> SEQ ID NO 78
<211> LENGTH: 21
<212> TYPE: DNA
<213> ORGANISM: Artificial Sequence
<220> FEATURE:
<223> OTHER INFORMATION: DNA/RNA hybrid

<400> SEQUENCE: 78
gugcuggccu uggugaggut t                                            21

<210> SEQ ID NO 79
<211> LENGTH: 18
<212> TYPE: DNA
<213> ORGANISM: Homo sapiens

<400> SEQUENCE: 79
ggctacgtcc agcgcacc                                                18

<210> SEQ ID NO 80
<211> LENGTH: 21
<212> TYPE: RNA
```

```
<213> ORGANISM: Homo sapiens

<400> SEQUENCE: 80
aaaccucacc aaagccagca c                                      21

<210> SEQ ID NO 81
<211> LENGTH: 21
<212> TYPE: DNA
<213> ORGANISM: Homo sapiens

<400> SEQUENCE: 81
aaggaggagg gcagaatcat c                                      21

<210> SEQ ID NO 82
<211> LENGTH: 21
<212> TYPE: DNA
<213> ORGANISM: Homo sapiens

<400> SEQUENCE: 82
aatgtgaatg cagaccaaag a                                      21

<210> SEQ ID NO 83
<211> LENGTH: 21
<212> TYPE: DNA
<213> ORGANISM: Homo sapiens

<400> SEQUENCE: 83
aaagcatttg tttgtacaag a                                      21

<210> SEQ ID NO 84
<211> LENGTH: 21
<212> TYPE: DNA
<213> ORGANISM: Homo sapiens

<400> SEQUENCE: 84
aagatccgca gacgtgtaaa t                                      21

<210> SEQ ID NO 85
<211> LENGTH: 21
<212> TYPE: DNA
<213> ORGANISM: Homo sapiens

<400> SEQUENCE: 85
aaacacacac tcgcgttgca a                                      21

<210> SEQ ID NO 86
<211> LENGTH: 19
<212> TYPE: DNA
<213> ORGANISM: Homo sapiens

<400> SEQUENCE: 86
aacgtacttg cagatgtga                                         19

<210> SEQ ID NO 87
<211> LENGTH: 19
<212> TYPE: DNA
<213> ORGANISM: Homo sapiens

<400> SEQUENCE: 87
acgtacttgc agatgtgac                                         19

<210> SEQ ID NO 88
<211> LENGTH: 19
<212> TYPE: DNA
```

<213> ORGANISM: Homo sapiens

<400> SEQUENCE: 88
gtacttgcag atgtgacaa                                          19

<210> SEQ ID NO 89
<211> LENGTH: 19
<212> TYPE: DNA
<213> ORGANISM: Homo sapiens

<400> SEQUENCE: 89
tacttgcaga tgtgacaag                                          19

<210> SEQ ID NO 90
<211> LENGTH: 19
<212> TYPE: DNA
<213> ORGANISM: Homo sapiens

<400> SEQUENCE: 90
acttgcagat gtgacaagc                                          19

<210> SEQ ID NO 91
<211> LENGTH: 19
<212> TYPE: DNA
<213> ORGANISM: Homo sapiens

<400> SEQUENCE: 91
cttgcagatg tgacaagcc                                          19

<210> SEQ ID NO 92
<211> LENGTH: 19
<212> TYPE: DNA
<213> ORGANISM: Homo sapiens

<400> SEQUENCE: 92
ttgcagatgt gacaagccg                                          19

<210> SEQ ID NO 93
<211> LENGTH: 19
<212> TYPE: DNA
<213> ORGANISM: Homo sapiens

<400> SEQUENCE: 93
tgcagatgtg acaagccga                                          19

<210> SEQ ID NO 94
<211> LENGTH: 19
<212> TYPE: DNA
<213> ORGANISM: Homo sapiens

<400> SEQUENCE: 94
gcagatgtga caagccgag                                          19

<210> SEQ ID NO 95
<211> LENGTH: 19
<212> TYPE: DNA
<213> ORGANISM: Homo sapiens

<400> SEQUENCE: 95
cagatgtgac aagccgagg                                          19

<210> SEQ ID NO 96
<211> LENGTH: 19
<212> TYPE: DNA

<213> ORGANISM: Homo sapiens

<400> SEQUENCE: 96
agatgtgaca agccgaggc    19

<210> SEQ ID NO 97
<211> LENGTH: 19
<212> TYPE: DNA
<213> ORGANISM: Homo sapiens

<400> SEQUENCE: 97
gatgtgacaa gccgaggcg    19

<210> SEQ ID NO 98
<211> LENGTH: 19
<212> TYPE: DNA
<213> ORGANISM: Homo sapiens

<400> SEQUENCE: 98
atgtgacaag ccgaggcgg    19

<210> SEQ ID NO 99
<211> LENGTH: 19
<212> TYPE: DNA
<213> ORGANISM: Homo sapiens

<400> SEQUENCE: 99
gtacttgcag atgtgacaa    19

<210> SEQ ID NO 100
<211> LENGTH: 19
<212> TYPE: DNA
<213> ORGANISM: Homo sapiens

<400> SEQUENCE: 100
tgcagatgtg acaagccga    19

<210> SEQ ID NO 101
<211> LENGTH: 19
<212> TYPE: DNA
<213> ORGANISM: Homo sapiens

<400> SEQUENCE: 101
gcagatgtga caagccgag    19

<210> SEQ ID NO 102
<211> LENGTH: 19
<212> TYPE: DNA
<213> ORGANISM: Homo sapiens

<400> SEQUENCE: 102
agatgtgaca agccgaggc    19

<210> SEQ ID NO 103
<211> LENGTH: 17
<212> TYPE: DNA
<213> ORGANISM: Homo sapiens

<400> SEQUENCE: 103
aacgtacttg cagatgt    17

<210> SEQ ID NO 104
<211> LENGTH: 17
<212> TYPE: DNA

<213> ORGANISM: Homo sapiens

<400> SEQUENCE: 104
acgtacttgc agatgtg                                                      17

<210> SEQ ID NO 105
<211> LENGTH: 17
<212> TYPE: DNA
<213> ORGANISM: Homo sapiens

<400> SEQUENCE: 105
cgtacttgca gatgtga                                                      17

<210> SEQ ID NO 106
<211> LENGTH: 17
<212> TYPE: DNA
<213> ORGANISM: Homo sapiens

<400> SEQUENCE: 106
gtacttgcag atgtgac                                                      17

<210> SEQ ID NO 107
<211> LENGTH: 17
<212> TYPE: DNA
<213> ORGANISM: Homo sapiens

<400> SEQUENCE: 107
tacttgcaga tgtgaca                                                      17

<210> SEQ ID NO 108
<211> LENGTH: 17
<212> TYPE: DNA
<213> ORGANISM: Homo sapiens

<400> SEQUENCE: 108
acttgcagat gtgacaa                                                      17

<210> SEQ ID NO 109
<211> LENGTH: 17
<212> TYPE: DNA
<213> ORGANISM: Homo sapiens

<400> SEQUENCE: 109
cttgcagatg tgacaag                                                      17

<210> SEQ ID NO 110
<211> LENGTH: 17
<212> TYPE: DNA
<213> ORGANISM: Homo sapiens

<400> SEQUENCE: 110
ttgcagatgt gacaagc                                                      17

<210> SEQ ID NO 111
<211> LENGTH: 17
<212> TYPE: DNA
<213> ORGANISM: Homo sapiens

<400> SEQUENCE: 111
tgcagatgtg acaagcc                                                      17

<210> SEQ ID NO 112
<211> LENGTH: 17
<212> TYPE: DNA

<213> ORGANISM: Homo sapiens

<400> SEQUENCE: 112
gcagatgtga caagccg                                                          17

<210> SEQ ID NO 113
<211> LENGTH: 17
<212> TYPE: DNA
<213> ORGANISM: Homo sapiens

<400> SEQUENCE: 113
cagatgtgac aagccga                                                          17

<210> SEQ ID NO 114
<211> LENGTH: 17
<212> TYPE: DNA
<213> ORGANISM: Homo sapiens

<400> SEQUENCE: 114
agatgtgaca agccgag                                                          17

<210> SEQ ID NO 115
<211> LENGTH: 17
<212> TYPE: DNA
<213> ORGANISM: Homo sapiens

<400> SEQUENCE: 115
gatgtgacaa gccgagg                                                          17

<210> SEQ ID NO 116
<211> LENGTH: 17
<212> TYPE: DNA
<213> ORGANISM: Homo sapiens

<400> SEQUENCE: 116
atgtgacaag ccgaggc                                                          17

<210> SEQ ID NO 117
<211> LENGTH: 17
<212> TYPE: DNA
<213> ORGANISM: Homo sapiens

<400> SEQUENCE: 117
tgtgacaagc cgaggcg                                                          17

<210> SEQ ID NO 118
<211> LENGTH: 17
<212> TYPE: DNA
<213> ORGANISM: Homo sapiens

<400> SEQUENCE: 118
gtgacaagcc gaggcgg                                                          17

<210> SEQ ID NO 119
<211> LENGTH: 20
<212> TYPE: DNA
<213> ORGANISM: Homo sapiens

<400> SEQUENCE: 119
ggcttgtcac attttctttg                                                       20

<210> SEQ ID NO 120
<211> LENGTH: 20
<212> TYPE: DNA

<213> ORGANISM: Homo sapiens

<400> SEQUENCE: 120
cccacaggga ttttcttgtc                                           20

<210> SEQ ID NO 121
<211> LENGTH: 20
<212> TYPE: DNA
<213> ORGANISM: Homo sapiens

<400> SEQUENCE: 121
ctttcccttt cctcgaactg                                           20

<210> SEQ ID NO 122
<211> LENGTH: 20
<212> TYPE: DNA
<213> ORGANISM: Homo sapiens

<400> SEQUENCE: 122
gctactgcca tccaatcgag                                           20

<210> SEQ ID NO 123
<211> LENGTH: 20
<212> TYPE: DNA
<213> ORGANISM: Homo sapiens

<400> SEQUENCE: 123
gtctttcctg gtgagagatc                                           20

<210> SEQ ID NO 124
<211> LENGTH: 20
<212> TYPE: DNA
<213> ORGANISM: Homo sapiens

<400> SEQUENCE: 124
ctgtcttggg tgcattggag                                           20

<210> SEQ ID NO 125
<211> LENGTH: 20
<212> TYPE: DNA
<213> ORGANISM: Homo sapiens

<400> SEQUENCE: 125
gaggcaggga tgatgttctg                                           20

<210> SEQ ID NO 126
<211> LENGTH: 20
<212> TYPE: DNA
<213> ORGANISM: Homo sapiens

<400> SEQUENCE: 126
catggcaaat tccatggcac                                           20

<210> SEQ ID NO 127
<211> LENGTH: 83
<212> TYPE: DNA
<213> ORGANISM: Homo sapiens

<400> SEQUENCE: 127
aaggcgaggc agcttgagtt aaacgaacgt acttgatctc tcaccaggaa agactgatac    60
agaacgatcg atacagaaac cac                                       83

<210> SEQ ID NO 128

```
<211> LENGTH: 36
<212> TYPE: DNA
<213> ORGANISM: artificial sequence
<220> FEATURE:
<223> OTHER INFORMATION: primer

<400> SEQUENCE: 128
gaacgtactt gcagatgtga caagccaagg cggtga                              36

<210> SEQ ID NO 129
<211> LENGTH: 36
<212> TYPE: DNA
<213> ORGANISM: artificial sequence
<220> FEATURE:
<223> OTHER INFORMATION: primer

<400> SEQUENCE: 129
gaacgtactt gcagatgtga caagccaagg cggtga                              36

<210> SEQ ID NO 130
<211> LENGTH: 6
<212> TYPE: PRT
<213> ORGANISM: Artificial sequence
<220> FEATURE:
<223> OTHER INFORMATION: peptide

<400> SEQUENCE: 130

Cys Asp Lys Pro Arg Arg
1               5

<210> SEQ ID NO 131
<211> LENGTH: 20
<212> TYPE: DNA
<213> ORGANISM: Artificial sequence
<220> FEATURE:
<223> OTHER INFORMATION: primer

<400> SEQUENCE: 131
ggcttgtcac atttttcttg                                                20

<210> SEQ ID NO 132
<211> LENGTH: 20
<212> TYPE: DNA
<213> ORGANISM: Artificial sequence
<220> FEATURE:
<223> OTHER INFORMATION: primer

<400> SEQUENCE: 132
cccacaggga ttttcttgtc                                                20

<210> SEQ ID NO 133
<211> LENGTH: 20
<212> TYPE: DNA
<213> ORGANISM: Artificial sequence
<220> FEATURE:
<223> OTHER INFORMATION: primer

<400> SEQUENCE: 133
ctttcccttt cctcgaactg                                                20

<210> SEQ ID NO 134
<211> LENGTH: 20
<212> TYPE: DNA
<213> ORGANISM: Artificial sequence
<220> FEATURE:
<223> OTHER INFORMATION: primer

<400> SEQUENCE: 134
```

```
gctactgcca tccaatcgag                                              20

<210> SEQ ID NO 135
<211> LENGTH: 20
<212> TYPE: DNA
<213> ORGANISM: Artificial sequence
<220> FEATURE:
<223> OTHER INFORMATION: primer

<400> SEQUENCE: 135
gtctttcctg gtgagagatc                                              20

<210> SEQ ID NO 136
<211> LENGTH: 20
<212> TYPE: DNA
<213> ORGANISM: Artificial sequence
<220> FEATURE:
<223> OTHER INFORMATION: primer

<400> SEQUENCE: 136
ctgtcttggg tgcattggag                                              20

<210> SEQ ID NO 137
<211> LENGTH: 20
<212> TYPE: DNA
<213> ORGANISM: Artificial sequence
<220> FEATURE:
<223> OTHER INFORMATION: primer

<400> SEQUENCE: 137
gaggcaggga tgatgttctg                                              20

<210> SEQ ID NO 138
<211> LENGTH: 20
<212> TYPE: DNA
<213> ORGANISM: Artificial sequence
<220> FEATURE:
<223> OTHER INFORMATION: primer

<400> SEQUENCE: 138
catggcaaat tccatggcac                                              20
```